（12) United States Patent
Mathas et al.

(10) Patent No.: US 9,115,404 B2
(45) Date of Patent: Aug. 25, 2015

(54) POLYNUCLEOTIDES FOR MEDICAL USE

(75) Inventors: Stephan Mathas, Berlin-Buch (DE);
Björn Lamprecht, Berlin-Buch (DE);
Bernd Dörken, Berlin-Buch (DE);
Constanze Bonifer, Berlin-Buch (DE)

(73) Assignee: MAX-DELBRÜCK-CENTRUM FÜR MOLEKULARE MEDIZIN BERLIN-BUCH, Berlin (DE)

( * ) Notice: Subject to any disclaimer, the term of this patent is extended or adjusted under 35 U.S.C. 154(b) by 344 days.

(21) Appl. No.: 13/379,084

(22) PCT Filed: Jun. 21, 2010

(86) PCT No.: PCT/EP2010/003714
§ 371 (c)(1),
(2), (4) Date: Jul. 18, 2012

(87) PCT Pub. No.: WO2010/145839
PCT Pub. Date: Dec. 23, 2010

(65) Prior Publication Data
US 2012/0277281 A1   Nov. 1, 2012

(30) Foreign Application Priority Data

Jun. 19, 2009  (EP) .................................... 09008082
Apr. 30, 2010  (EP) .................................... 10004587

(51) Int. Cl.
*C07H 21/02*   (2006.01)
*C07H 21/04*   (2006.01)
*C12Q 1/68*    (2006.01)
*A61K 31/70*   (2006.01)

(52) U.S. Cl.
CPC ........ *C12Q 1/6886* (2013.01); *C12Q 2600/154* (2013.01); *C12Q 2600/156* (2013.01)

(58) Field of Classification Search
None
See application file for complete search history.

(56) References Cited

U.S. PATENT DOCUMENTS 7,429,451 B2   9/2008   Nakagawara et al.

FOREIGN PATENT DOCUMENTS

WO        2010145839 A3    12/2010

OTHER PUBLICATIONS

Lamprecht et al. Nature Medicine vol. 16(5):571-579+online methods page, May 2010.*
Miyagishi et al (Nature Biotechnology vol. 19:497-500, 2002).*
Adam Bagg, MD, "Lineage Ambiguity, Infidelity, and Promiscuity in Immunophenotypically Complex Acute Leukemias, Genetic and Morphologic Correlates," American Journal of Clinical Pathology (AJCP), Oct. 2007, pp. 545-548, vol. 128, No. 4.

C. Bonifer et al., "The Transcriptional Regulation of the Colony-Stimulating Factor 1 Receptor (csf1r) Gene During Hematopoiesis," Frontiers in Bioscience, Jan. 2008, pp. 549-560, vol. 13.
G.V. Borzillo et al., "Macrophage Lineage Switching of Murine Early Pre-B Lymphoid Cells Expressing Transduced fms Genes," Molecular and Cellular Biology, Jun. 1990, pp. 2703-2714, vol. 10, No. 6.
C.J. Burns et al., "Discovery of 2-(alpha-Methylbenzylamino) Pyrazines as Potent Type II Inhibitors of FMS," Bioorganic & Medicinal Chemistry Letters, Feb. 2009, pp. 1206-1209, vol. 19, No. 4.
B.J. Chyla et al., "Deletion of Mtg16, a Target of t(16;21), Alters Hematopoietic Progenitor Cell Proliferation and Lineage Allocation," Molecular and Cellular Biology, Oct. 2008, pp. 6234-6247, vol. 28, No. 20.
C. Cobaleda et al., "Conversion of Mature B Cells into T Cells by Dedifferentiation to Uncommitted Progenitors," Nature, Sep. 2007, pp. 473-477, vol. 449, No. 7161.
X.-M. Dai et al., "Targeted Disruption of the Mouse Colony-Stimulating Factor 1 Receptor Gene Results in Osteopetrosis, Mononuclear Phagocyte Deficiency, Increased Primitive Progenitor Cell Frequencies, and Reproductive Defects," Blood, Jan. 2002, pp. 111-120, vol. 99, No. 1.
M. Delhase et al., "Positive and Negative Regulation of IkappaB Kinase Activity Through IKKbeta Subunit Phosphorylation," Science, Apr. 1999, pp. 309-313, vol. 284, No. 5412.
J.R. Downing et al., "Peptide Antisera to Human Colony-Stimulating Factor 1 Receptor Detect Ligand-Induced Conformational Changes and a Binding Site for Phosphatidylinositol 3-Kinase," Molecular and Cellular Biology, May 1991, pp. 2489-2495, vol. 11, No. 5.
R. Druker et al., "Retrotransposon-Derived Elements in the Mammalian Genome: a Potential Source of Disease," Journal of Inherited Metabolic Disease, May 2004, pp. 319-330, vol. 27, No. 3.
A. Eden et al., "Chromosomal Instability and Tumors Promoted by DNA Hypomethylation," Science, Apr. 2003, p. 455, vol. 300, No. 5618.
A. Ehlers et al., "Histone Acetylation and DNA Demethylation of B Cells Result in a Hodgkin-Like Phenotype," Leukemia, Apr. 2008, pp. 835-841, vol. 22, No. 4.
Melanie Ehrlich, "DNA Methylation in Cancer: Too Much, But Also Too Little," Oncogene, Aug. 2002, pp. 5400-5413, vol. 21, No. 35.
Manel Esteller, "CpG Island Hypermethylation and Tumor Suppressor Genes: a Booming Present, a Brighter Future," Oncogene, Aug. 2002, pp. 5427-5440, vol. 21, No. 35.
T. Fan et al., "DNA Hypomethylation Caused by Lsh Deletion Promotes Erythroleukemia Development," Epigenetics, May-Jun. 2008, pp. 134-142, vol. 3, No. 3.
G.J. Faulkner et al., "The Regulated Retrotransposon Transcriptome of Mammalian Cells," Nature Genetics, May 2009, pp. 563-571, vol. 41, No. 5.
A.L. Feldman et al., "Clonally Related Follicular Lymphomas and Histiocytic/Dendritic Cell Sarcomas: Evidence for Transdifferentiation of the Follicular Lymphoma Clone," Blood, Jun. 2008, pp. 5433-5439, vol. 111, No. 12.

(Continued)

*Primary Examiner* — Sean McGarry
(74) *Attorney, Agent, or Firm* — Ryan, Mason & Lewis, LLP

(57) ABSTRACT

The invention pertains to a RNA molecule transcribed form a long terminal repeat (LTR) sequence, comprising
a sequence encoding a gene, such as CSF1R, and
a sequence that is at least in part found in the LTR,
in particular for detecting cancer in a subject.

11 Claims, 39 Drawing Sheets

(56) References Cited

OTHER PUBLICATIONS

Figure 1A:
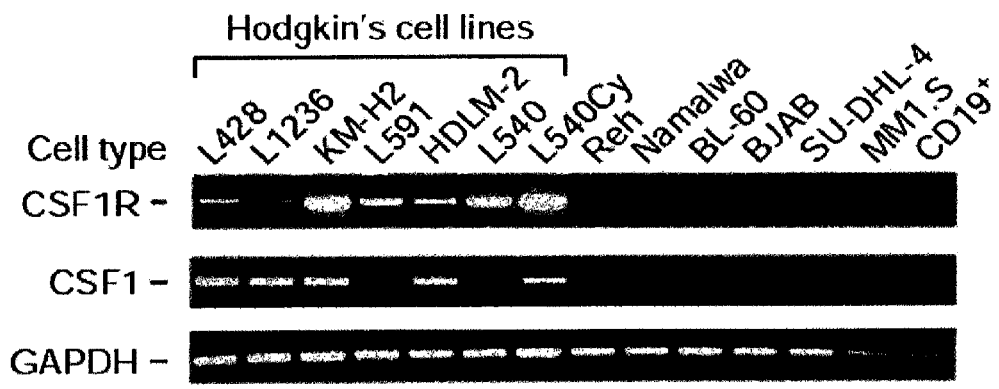
Figure 1B:
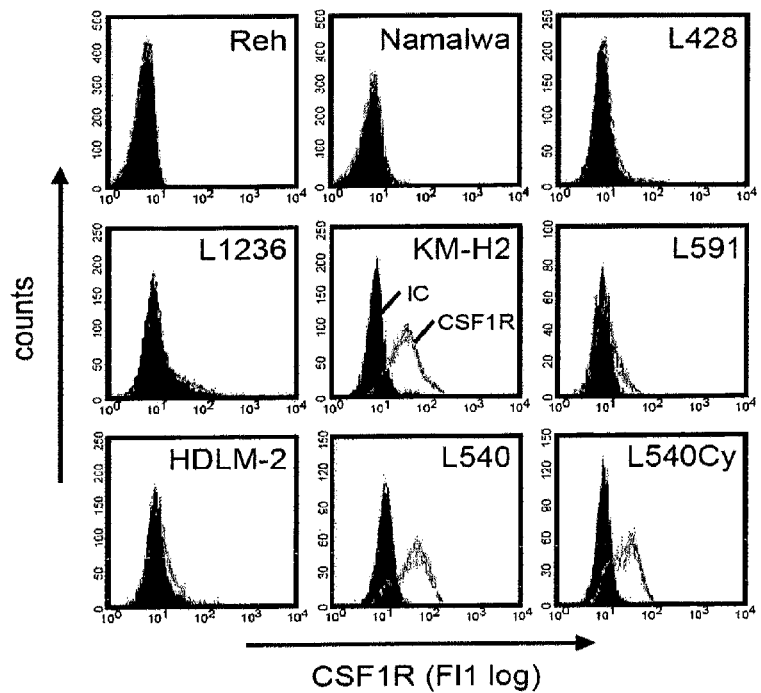
Figure 1C:
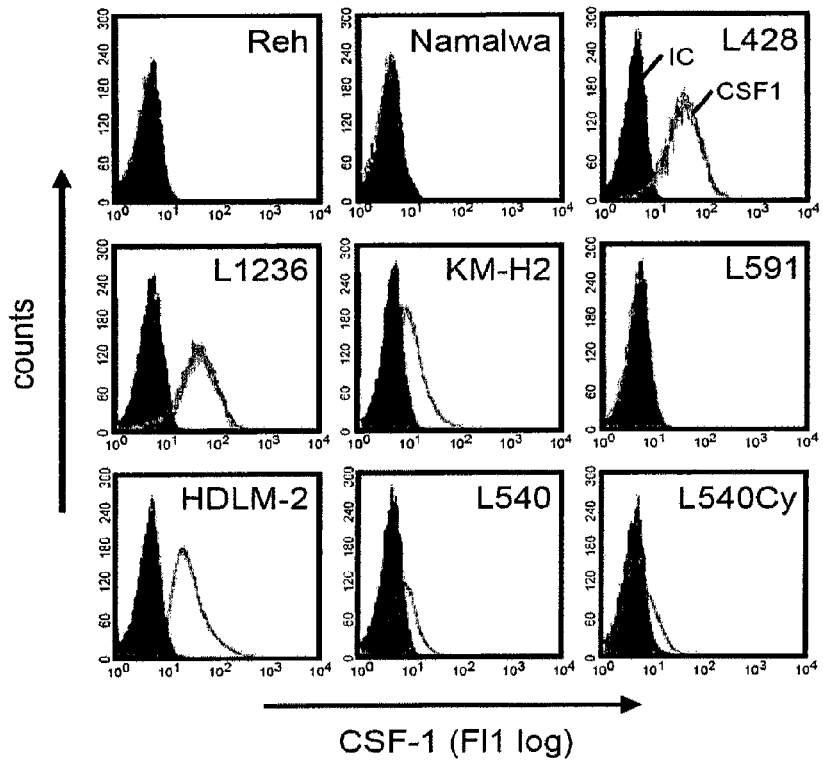
Figure 1D:
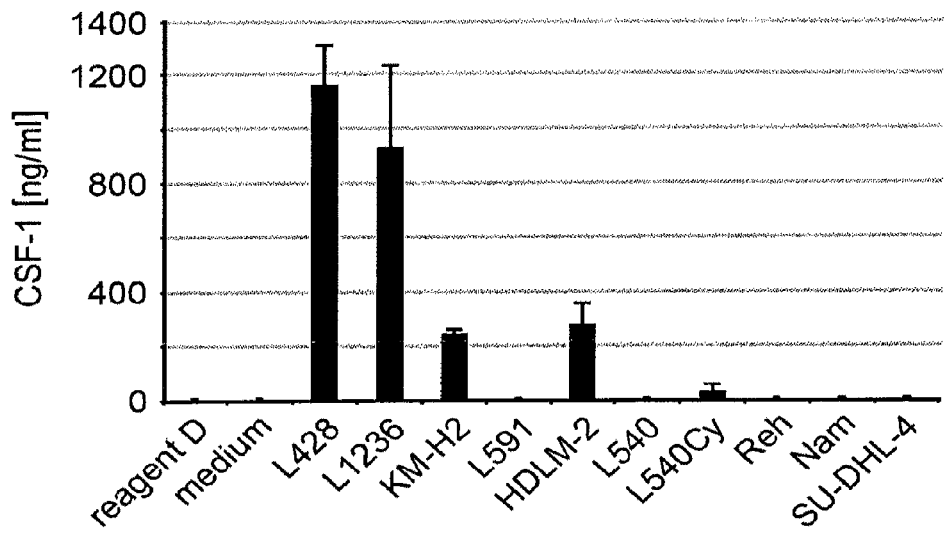

G.A. Follows et al., "Differential Transcription Factor Occupancy But Evolutionarily Conserved Chromatin Features at the Human and Mouse M-CSF (CSF-1) Receptor Loci," Nucleic Acids Research, Oct. 2003, pp. 5805-5816, vol. 31, No. 20.

T. Gamou et al., "The Partner Gene of AML1 in t(16;21) Myeloid Malignancies is a Novel Member of the MTG8 (ETO) Family," Blood, Jun. 1998, pp. 4028-4037, vol. 91, No. 11.

N. Goardon et al., "ETO2 Coordinates Cellular Proliferation and Differentiation During Erythropoiesis," The EMBO Journal, Jan. 2006, pp. 357-366, vol. 25, No. 2.

M. Hinz et al., "Nuclear Factor kappaB-Dependent Gene Expression Profiling of Hodgkin's Disease Tumor Cells, Pathogenetic Significance, and Link to Constitutive Signal Transducer and Activator of Transcription 5a Activity," The Journal of Experimental Medicine, Sep. 2002, pp. 605-617, vol. 196, No. 5.

U.E. Höpken et al., "Up-Regulation of the Chemokine Receptor CCR7 in Classical But Not in Lymphocyte-Predominant Hodgkin Disease Correlates with Distinct Dissemination of Neoplastic Cells in Lymphoid Organs," Blood, Feb. 2002, pp. 1109-1116, vol. 99, No. 4.

G. Howard et al., "Activation and Transposition of Endogenous Retroviral Elements in Hypomethylation Induced Tumors in Mice," Oncogene, Jan. 2008, pp. 404-408, vol. 27, No. 3.

J. Huang et al., "Lsh, an Epigenetic Guardian of Repetitive Elements," Nucleic Acids Research, Sep. 2004, pp. 5019-5028, vol. 32, No. 17.

B.A. Hug et al., "ETO Interacting Proteins," Oncogene, May 2004, pp. 4270-4274, vol. 23, No. 24.

T. Ikawa et al., "Long-Term Cultured E2A-Deficient Hematopoietic Progenitor Cells are Pluripotent," Immunity, Mar. 2004, pp. 349-360, vol. 20, No. 3.

K.M. Irvine et al., "A CSF-1 Receptor Kinase Inhibitor Targets Effector Functions and Inhibits Pro-Inflammatory Cytokine Production from Murine Macrophage Populations," The FASEB Journal, Sep. 2006, pp. 1921-1923, vol. 20, No. 11.

M. Janz et al., "Reprogramming of B Lymphoid Cells in Human Lymphoma Pathogenesis," Cell Cycle, May 2006, pp. 1057-1061, vol. 5, No. 10.

P. Jern et al., "Effects of Retroviruses on Host Genome Function," The Annual Review of Genetics, Dec. 2008, pp. 709-732, vol. 42.

P.A. Jones et al., "The Fundamental Role of Epigenetic Events in Cancer," Nature Reviews. Genetics, Jun. 2002, pp. 415-428, vol. 3, No. 6.

S. Joos et al., "Classical Hodgkin Lymphoma is Characterized by Recurrent Copy Number Gains of the Short Arm of Chromosome 2," Blood, Feb. 2002, pp. 1381-1387, vol. 99, No. 4.

F. Jundt et al., "Loss of PU.1 Expression is Associated with Defective Immunoglobulin Transcription in Hodgkin and Reed-Sternberg Cells of Classical Hodgkin Disease," Blood, Apr. 2002, pp. 3060-3062, vol. 99, No. 8.

M. Kochetkova et al., "CBFA2T3 (MTG16) is a Putative Breast Tumor Suppressor Gene from the Breast Cancer Loss of Heterozygosity Region at 16q24.3," Cancer Research, Aug. 2002, pp. 4599-4604, vol. 62, No. 16.

R. Kumar et al., "CBFA2T3-ZNF652 Corepressor Complex Regulates Transcription of the E-Box Gene HEB," The Journal of Biological Chemistry, Jul. 2008, pp. 19026-19038, vol. 283, No. 27.

Ralf Küppers, "The Biology of Hodgkin's Lymphoma," Nature Reviews. Cancer, Jan. 2009, pp. 15-27, vol. 9, No. 1.

R. Küppers et al., "Identification of Hodgkin and Reed-Sternberg Cell-Specific Genes by Gene Expression Profiling," The Journal of Clinical Investigation, Feb. 2003, pp. 529-537, vol. 111, No. 4.

S.H. Lee et al., "Functional Interactions Between an Atypical NF-kappaB Site from the Rat CYP2B1 Promoter and the Transcriptional Repressor RBP-Jkappa/CBF1," Nucleic Acids Research, May 2000, pp. 2091-2098, vol. 28, No. 10.

O. Legrand et al., "Adult Biphenotypic Acute Leukaemia: an Entity With Poor Prognosis Which is Related to Unfavourable Cytogenetics and P-Glycoprotein Over-Expression," British Journal of Haematology, Jan. 1998, pp. 147-155, vol. 100, No. 1.

X. Li et al., "IKKalpha, IKKbeta, and NEMO/IKKgamma are Each Required for the NF-kappa B Mediated Inflammatory Response Program," The Journal of Biological Chemistry, Nov. 2002, pp. 45129-45140, vol. 277, No. 47.

R.A.F. MacLeod et al., "Karyotypic Dissection of Hodgkin's Disease Cell Lines Reveals Ectopic Subtelomeres and Ribosomal DNA at Sites of Multiple Jumping Translocations and Genomic Amplification," Leukemia, Oct. 2000, pp. 1803-1814, vol. 14, No. 10.

I.A. Maksakova et al., "Keeping Active Endogenous Retroviral-Like Elements in Check: the Epigenetic Perspecitve," Cellular and Molecular Life Sciences (CMLS), Nov. 2008, pp. 3329-3347, vol. 65, No. 21.

J.I. Martin-Subero et al., "Recurrent Involvement of the REL and BCL11A Loci in Classical Hodgkin Lymphoma," Blood, Feb. 2002, pp. 1474-1477, vol. 99, No. 4.

S. Mathas et al., "Aberrantly Expressed c-Jun and JunB are a Hallmark of Hodgkin Lymphoma Cells, Stimulate Proliferation and Synergize with NF-kappaB," The EMBO Journal, Aug. 2002, pp. 4104-4113, vol. 21, No. 15.

S. Mathas et al., "Intrinsic Inhibition of Transcription Factor E2A by HLH Proteins ABF-1 and Id2 Mediates Reprogramming of Neoplastic B Cells in Hodgkin Lymphoma," Nature Immunology, Feb. 2006, pp. 207-215, vol. 7, No. 2.

S.L. Nutt et al., "The Transcriptional Regulation of B Cell Lineage Commitment," Immunity, Jun. 2007, pp. 715-725, vol. 26, No. 6.

K. Ohshima et al., "Chromosome 16q Deletion and Loss of E-Cadherin Expression in Hodgkin and Reed-Sternberg Cells," International Journal of Cancer, Jun. 2001, pp. 678-682, vol. 92, No. 5.

F.J. Pixley et al., "CSF-1 Regulation of the Wandering Macrophage: Complexity in Action," Trends in Cell Biology, Nov. 2004, pp. 628-638, vol. 14, No. 11.

G. Prindull et al., "Environmental Guidance of Normal and Tumor Cell Plasticity: Epithelial Mesenchymal Transitions as a Paradigm," Blood, Apr. 2004, pp. 2892-2899, vol. 103, No. 8.

M.F. Roussel et al., "Transforming Potential of the c-fms Proto-Oncogene (CSF-1 Receptor)," Nature, Feb. 1987, pp. 549-552, vol. 325, No. 6104.

Y. Wang et al., "Role of IGF-I Signaling in Regulating Osteoclastogenesis," Journal of Bone and Mineral Research, Sep. 2006, pp. 1350-1358, vol. 21, No. 9.

N. Heisterkamp et al., "Isolation of v-fms and Its Human Cellular Homolog," Virology, 1983, pp. 248-258, vol. 126.

Arian F.A. Smit, "Identification of a New, Abundant Superfamily of Mammalian LTR-Transposons," Nucleic Acids Research, Apr. 1993, pp. 1863-1872, vol. 21, No. 8.

A. Souabni et al., "Oncogenic Role of Pax5 in the T-Lymphoid Lineage Upon Ectopic Expression From the Immunoglobulin Heavy-Chain Locus," Blood, Jan. 2007, pp. 281-289, vol. 109, No. 1.

H. Tagoh et al., "The Mechanism of Repression of the Myeloid-Specific c-fms Gene by Pax5 During B Lineage Restriction," The EMBO Journal, Mar. 2006, pp. 1070-1080, vol. 25, No. 5.

A. Ushmorov et al., "Epigenetic Processes Play a Major Role in B-Cell-Specific Gene Silencing in Classical Hodgkin Lymphoma," Blood, Mar. 2006, pp. 2493-2500, vol. 107, No. 6.

J. Visvader et al., "Differential Transcription of Exon 1 of the Human c-fms Gene in Placental Trophoblasts and Monocytes," Mollecular and Cellular Biology, Mar. 1989, pp. 1336-1341, vol. 9, No. 3.

K. Walter et al., "Stem Cell-Specific Epigenetic Priming and B Cell-Specific Transcriptional Activation at the Mouse Cd19 Locus," Blood, Sep. 2008, pp. 1673-1682, vol. 112, No. 5.

S. Aharinejad et al., "Colony-Stimulating Factor-1 Blockade by Antisense Oligonucleotides and Small Interfering RNAs Suppresses Growth of Human Mammary Tumor Xenografts in Mice," Cancer Research, Aug. 2004, pp. 5378-5384, vol. 64, No. 15.

M.J. Borowitz et al., "Acute Leukaemias of Ambiguous Lineage," in WHO Classification of Tumours of Haematopoietic and Lymphoid Tissues, Chapter 7, 2008, pp. 149-155.

A. Moreau et al., "Immunohistochemical Detection of Cells Positive for Colony-Stimulating Factor 1 in Lymph Nodes from Reactive Lymphadenitis, and Hodgkin's Disease," Leukemia, Feb. 1992, pp. 126-130, vol. 6, No. 2.

\* cited by examiner

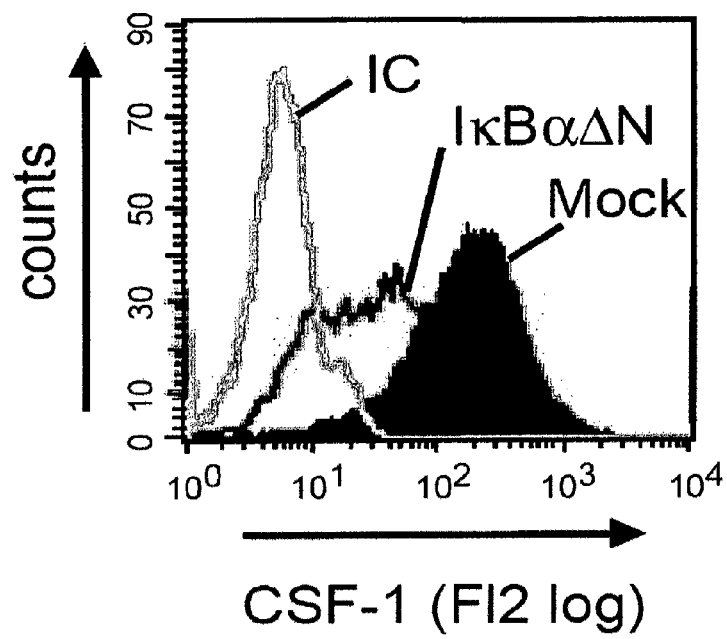
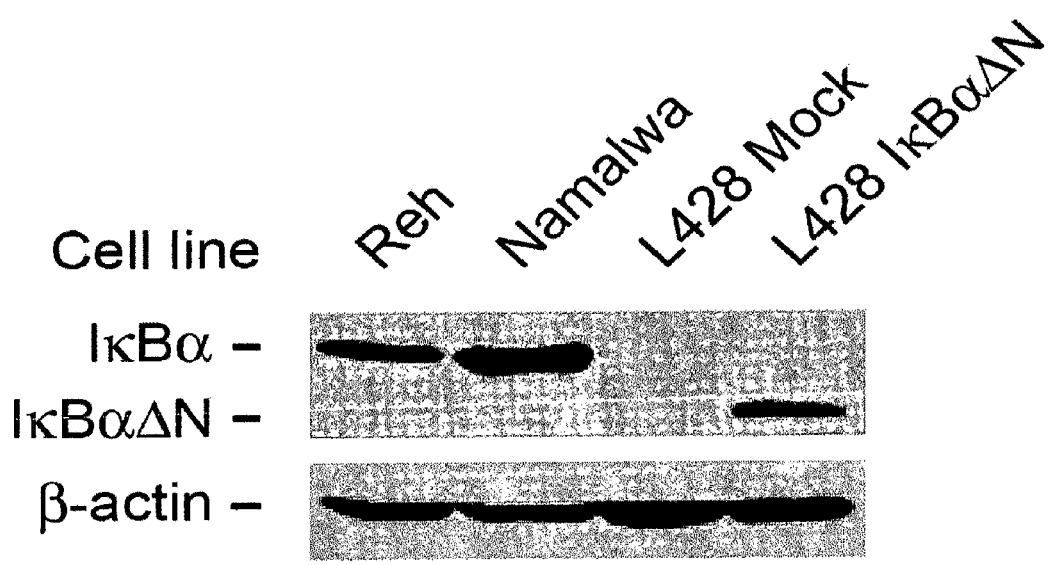
Fig. 2

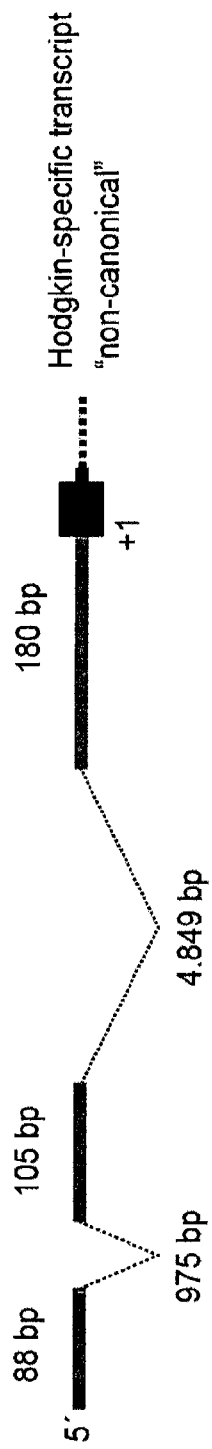
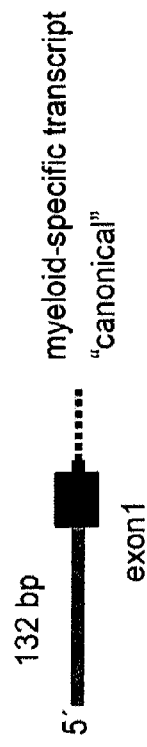
Fig. 4c
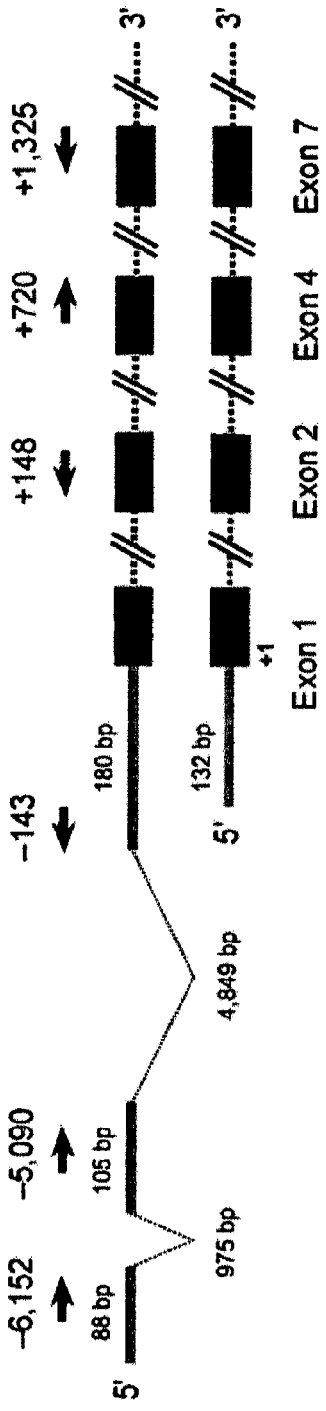
Fig. 5a

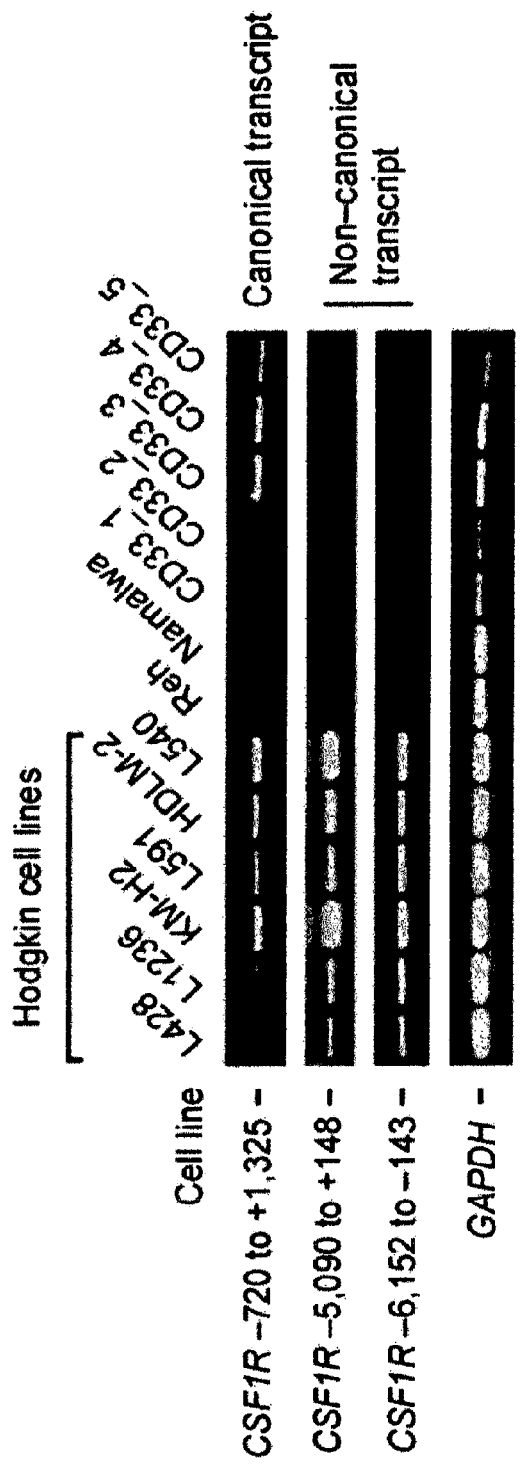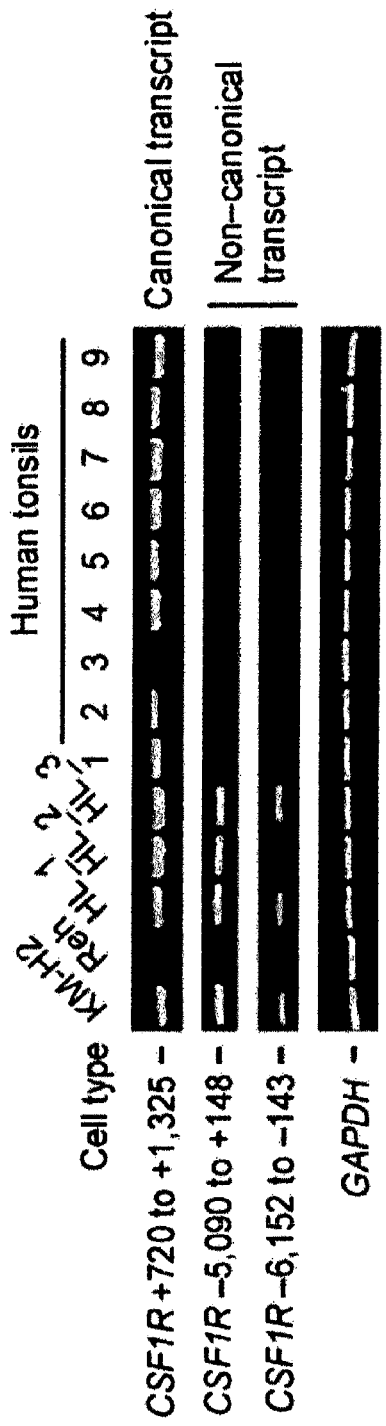

HL *CSF1R* -6 kB promoter   SEQ ID NO 94 chr5:149,452,780
|
TTTTCATAGTGCAGTAGTTCCCCCTTATTGGCAATTTCAGTTACTTGTGATCAATCCATGTC
⮕ -382

E-Box    GATA
CAAAAATATGAAGGTACTTTGAGAGAGAGAGAGAGACTACATTCACGTGGCTTTTATCACAG

TGTAGTGTTATAATTGTCTTATTGTATTATTAGTTATTATTGTTGATCTCTTACTTTGCCTA
 GATA     GATA                     GATA            SP1
ACTGATAAACTTTATCATAGGTATGTAGGTGATATGGTTGCGTGTGTGCCCACCCAATTCT

E-Box      SP1            GATA    AP-1
CGAGGTTGAATTGTAAAAATTCCCACATGTCAAGGGTGGGGCAGGTCGAGATAATTGAATCA
⮕ -142

TGGGGGAGTTTTTGCGCATACTGTTCTCCGTGGTAGTGATTAGTCGTCACGAGATCTGATCGT
⮕ -85
TATA     NF-κB         HL-specific START site (-6197)
TTTATAAATGGGAGTTCGGCTGCATATAGTCTTTTGCGTGGGTGATGTTGCATGTCATTCT
                                 ⬅+14
                                                        AP-1
CGTCCTGCTTTTGCGCTTGCACTATGCATTGCTGAGGGGTGCTCAGGCATGCTCAGTCTGAGTCA

ATTAAACGTGCCTTTCCTTTACAAATCACGGCAGTCTTGCGTATGCTTTATTAGCACTATGAG

AACACAGTAATACAGTAGGTATAGGAAAAAAACATGGCATATACAGGGTTTAGTACTATCTG
                                                                      |
                                                   chr5:149,452,161

▨ LTR region (*THE1B*)

Fig. 6b

**Hodgkin-specific transcript (non-canonical *CSF1R* transcript)**     SEQ ID NO 3

CTCTTTTGCCTGCCATCATGTTGGATGTGATTCTGCTCCTCCTTTGCCTTCCACTATGA
TTCTGAGGCCTCCTCAGCCATGCTGAAC*TG*TTTACCTGTTCTGGATGTTTCATATAGAT
GGAGTCGTATGACATTTTGCTACTGGCTTCATTGACTTAACACAGTGTTTTCAAGGTTC
ATCCACAGTGTAGCA*GCT*AAAAGGGGAAGAAGAGGATCAGCCCAAGGAGGAGGAAGA
GGAAAACAAGACAAACAGCCAGTGCAGAGGAGAGGAACGTGTGTCCAGTGTCCCGAT
CCCTGCGGAGCTAGTAGCTGAGAGCTCTGTGCCCTGGGCACCTTGCAGCCCTGCACC
TGCCTGCCACTTCCCCACCGAGGCC<u>ATG</u>GGCCCAGGAGTTCTGCTGCTCCTGCTGGT
GGCCACAGCTTGGCATG

**myeloid-specific transcript (canonical *CSF1R* transcript)**     SEQ ID NO 11

AAGACAAACAGCCAGTGCAGAGGAGAGGAACGTGTGTCCAGTGTCCCGATCCCTGCG
GAGCTAGTAGCTGAGAGCTCTGTGCCCTGGGCACCTTGCAGCCCTGCACCTGCCTGC
CACTTCCCCACCGAGGCC<u>ATG</u>GGCCCAGGAGTTCTGCTGCTCCTGCTGGTGGCCACA
GCTTGGCATG

Fig. 11

```
THE1B family
                    GATA                   Sp1              -142
THE1B consensus  TGATATGGTTTGGCTGTGT--CCCCACCCAAATCTCATCTTGAATTGTAGCTCCCATAATTC
CSF1R   THE1B    TGATATGGTTTGGCTGTGT--CCCCACCCAATTCTCACCTTGAATTGTA------ATAATTC
703     THE1B    TGATATGGTTTGGCTCTGAGTCCCCTGCCAAATCTCATTTC-----GTAGCTCCCATAATTC
707     THE1B    TGATATGCTTTGGCTGTGT--CTCCACCCAAATCTTATCTTGAATTGTAGCTTTCGTAATTC
709     THE1B     GATATGGTTTGGCTGTGT--CTCCAACCAAATCTCATCTTGAATTGTAGCTCCCATAATTC
712     THE1B    TGATATAGTTTAGCTGTGT--CCCCACCCATATCTCATCGTGAATT---------------
715     THE1B               TGTCCCCACCCAAAGCTCATCTGGAATTGTAGCTCCCACAATTC
716     THE1B     ATATGGTTTGGCCCTGTGTCTCCACCCAAATCTCACTTTGAATTGTA------ATAATCC
THE1A family
702     THE1A     GATATGGTTTGGCTGTGT--CCCCATTCAAATTTCAAC-TGAATTGTATCGCCCAGAATTC
713     THE1A    TGATATGGTTTGGCTGTGT--CCTCACCAAAATCTCAACTTGAATTGTATCTCCCAGAATTC THE1B family
        E-box     Sp1          GATA    AP-1     Sp1
THE1B    CCACGTGTCGTGGGAGGGACCCGGTGGGAGGTAATTGAATCATGGGGCGGGTC----TTTCCCGTGCTGTTCT
CSF1R    CCACATGTCAAGGGTGGGGCCAGGT-GGAGATAATTGAATCATGGGGCAGTT-----TTCCCCATACTGTTCT
703      TCGTGTGTTGTGGGAGGGACCTGGTGGGAGATGATTGAATCATGGGGGCAGGTC----TTTCCAGTGCTGTTCT
707      CCACGTGTTGTGGGAGGGACCTGGTGGGAGATACCTGAATCGAATCGTTGGGGGAGTTTCCCCAATACTGTTCT
709      CTAGCGGTGTT-----------GTGGGAGATCATTGAATCATGGGGCGGTTTC------CCACATACTGTTCT
712      CCATGTCTTGTGGGAGGGACTCTGTGGGAGG-AATTGAATCATGGGGCAGGTC----TTTTGTGTGCTGTTCT
715      CCACATGTTGTGGGAGGGACCCGGTGGGAGGTAATTGAATCATGGGCGTGTC-----TTTTCTGTGCTGTTCT
716      CCACGTGTCCAGGGCAGGGTCAGGCA-GAGTTAATGGAATCATGAGG-GTGGTT----TCCCCCATGCTGTTCT
THE1A family
702      CCACATGTTATGGGAGGGACCCAGGGGGAGGTAATTGAATCATGGGGGCCAGTC----TTTCCCATGCTATTC-
713      CCATGTGTTGTGGGAGGGACCCGG-GGGAGGTAGCTTAATCATGGGGGCTGGTC----TTTCCTGTGTTCTTCT THE1B family
          GATA                         TATA    NF- B            Start
THE1B    CGTGATAGTGAATAAGTCTCACGAGATCTGATGGTTTTATAAAGGGGAGTTCCCCTGCACAWG
CSF1R    CGTGGTAGTGATTAAGTCTCACGAGATCTGATGGTTTTATAAATGGGAGTTCCCCTGCATATAC
703      TGCGACAGTGAATGGGTCTCGCGAGATCTGATGGTTTAAAAACGGGGTTCTCTACACAAGCTC
707      TG---TAGTGAATGAGTCTTATGAGATCTGATGGTTTTATAATGGGTTTCCCCTTTCACTTAGCT
709      CGTGGTGGTGCATAAGTCTCACGAGATCTGATGGTTTTATAAG-GGGTTTCCCTTTTGCTTGGCTTTC
712      CATGATAGTGAATAAGTCTCATAAGATCTGGTGGTTTTATAAGGGGGAGTTTCCCTGCACAAGCTCTCT
715      CGTGATAGTGAATAAGTCTCATGAGATCTGATGGTTTTATAaggggagttttcctgcacaagatctctct
716      TGTGGTAGTGAATAAGTCTCATGAGAGCTGATGGTTTTATAAATTGGAGTCCCCTTGCACAAGCTCTCTTG
THE1A family
702      CGTGATATTGAATAAGTCTCACAAGATCTGGTGGGTTTATCAGGGGTTTCTGCTTTTGCTTCTTCCTCAGTTT
713
CATGATAGTGAATAAGTCTCACGAATAAGTCTCACGAGATCTGATGGGTTTATCTGGGGTTTCTGTTTTTGCTTCTTCC
(realign 713)..GAATAAGTCTCACGAGATCTGATGGGTTTATCTGGGGTTTCTGTTTTTGCTTCTTCC conserved  TAGTGAATAAGTCTCACGAGATCTGATGGTTTTATAA
```

THE1B consensus (SEQ ID NO 95)
CSF1R THE1B (SEQ ID NO 96)
703 THE1B (SEQ ID NO 97)
707 THE1B (SEQ ID NO 98)
709 THE1B (SEQ ID NO 99)
712 THE1B (SEQ ID NO 100)
715 THE1B (SEQ ID NO 101)
716 THE1B (SEQ ID NO 102)
702 THE1B (SEQ ID NO 103)
713 THE1B (SEQ ID NO 104)

Fig. 17

Alignment of the *CSF1R*-LTR with the consensus *THE1B*-family repeat sequence

*THE1B*-LTR (SEQ ID NO 106)
*CSF1R*-LTR (SEQ ID NO 105)

```
            GATA                Sp1              -142
CSF1R   1   TGATATGGTTTGGCTGTGTCCCCACCCAATTCTCACCTTGAATTGTA------ATAATTCCCA   57
            ||||||||||||||||||||||||||||| ||||| |||||||||||       |||||||||
THE1B   1   TGATATGGTTTGGCTGTGTCCCCACCCAAATCTCATCTTGAATTGTAGCTCCCATAATTCCCA   63

E-box       Sp1                 GATA    AP-1
CSF1R   58  CATGTCAAGGGTGGGGCCAGGTGG-AGATAATTGAATCATGGGGGCAGTT-TTCCCCATACTG  118
            | ||||   ||| ||| || ||||| || ||||||||||||||||||||| | || ||| | |||
THE1B   64  CGTGTCCTGGGAGGGACCCGGTGGGAGGTAATTGAATCATGGGGCGGGTCTTTCCCGTGCTG  126

TATA    NF-kB
CSF1R   119 TTCTCGTGGTAGTGATTAAGTCTCACGAGATCTGATGGTTTTATAAATGGGAGTTCCCCTGCA  181
            |||||||| ||||||| ||||||||||||||||||||||||||||||| |||||||||||||||
THE1B   127 TTCTCGTGATAGTGAATAAGTCTCACGAGATCTGATGGTTTTATAAAGGGGAGTTCCCCTGCA  189

Start of transcription
CSF1R   182 TATACTCTTTTGCCTGCCATCATGTTGGATGTGATTCTGCTCCTCCTTTGCCTTCCACTATGA  244
            |   ||||  ||||||||||  |||||  || |||  |  |||||||||||  ||||||| | ||||
THE1B   190 CAWGCTCTCTTGCCTGCCGCCATGTAAGACGTGMCTTTGCTCCTCCTTCGCCTTCCGCCATGA  252

CSF1R   245 TTCTGAGGCCTCCTCAGCCATGCTGAACTGTGAGTCAATTAAACCTCCTTTCCTTTAGAAATC  307
            ||  |||||||||  ||||||||  |||||||||||  ||||||||||  |||||||||| ||||
THE1B   253 TTGTGAGGCCTCCCCAGCCATGTGGAACTGTGAGTCCATTAAACCT-CTTTCCTTTATAAATT  314

CSF1R   308 ACCCAGTCTTGGGTATGTCTTTATTAGCAGTATGAGAACAGACTAATACA  357
            |||||||||  |||||||||||||||||||||| |||||||||||||||||
THE1B   315 ACCCAGTCTCGGGTATGTCTTTATTAGCAGCGTGAGAACAGACTAATACA  364
```

Fig. 18a

| Hg19 coordinates | size | CG content |
|---|---|---|
| chr8:97,439,412–97,439,775 | 364 | 0 |
| chr20:45,693,515–45,693,877 | 363 | 3 |
| chr17:44,096,396–44,096,758 | 363 | 4 |
| chr16:67,403,468–67,403,828 | 361 | 3 |
| chr22:25,985,686–25,986,049 | 364 | 3 |
| chr4:160,641,739–160,642,102 | 364 | 3 |
| chr8:41,683,169–41,683,531 | 363 | 4 |
| chr12:129,263,009–129,263,371 | 363 | 5 |
| chr15:59,818,708–59,819,071 | 364 | 5 |
| chr13:95,503,474–95,503,835 | 362 | 1 |

Fig. 18b

Start of transcription

```
THE1B   181
TCCCCTGCACAWGCTCTCTTGCCTGCCGCCATGTAAGACGTGMCTTTGCTCCTCCTTCGC   240
             ||||||||| |  ||||  |||||||||  |||||  ||  |||   |
|||||||||||  ||
CSF1R   173
TCCCCTGCATATACTCTTTTGCCTGCCATCATGTTGGATGTGATTCTGCTCCTCCTTTGC   232

GATTGTGAGGCCTCCCCAGCCATG       THE1B primer_1
                  CCATGATTGTGAGGCCTCCC           THE1B primer_2
THE1B   241   CTTCCGCCATGATTGTGAGGCCTCCCCAGCCATGTGGAACT/gtgagtCCATTAAA
295
              |||||  | ||||||| ||||||||||| ||||||||  |||||/|||||||  ||||||
CSF1R   233   CTTCCACTATGATTCTGAGGCCTCCTCAGCCATGCTGAACT/gtgagtCAATTAAA
287
                  CTATGATTCTGAGGCCTCCT                CSF1R primer_1
                    GATTCTGAGGCCTCCTCAGCCATG          CSF1R primer_2
```

THE1B 181 (SEQ ID NO 108)
CSF1R 173 (SEQ ID NO 107)
THE1B primer_1 (SEQ ID NO 109)
THE1B primer_2 (SEQ ID NO 110)
CSF1R primer_1 (SEQ ID NO 111)
CSF1R primer_2 (SEQ ID NO 112)

Fig. 18c

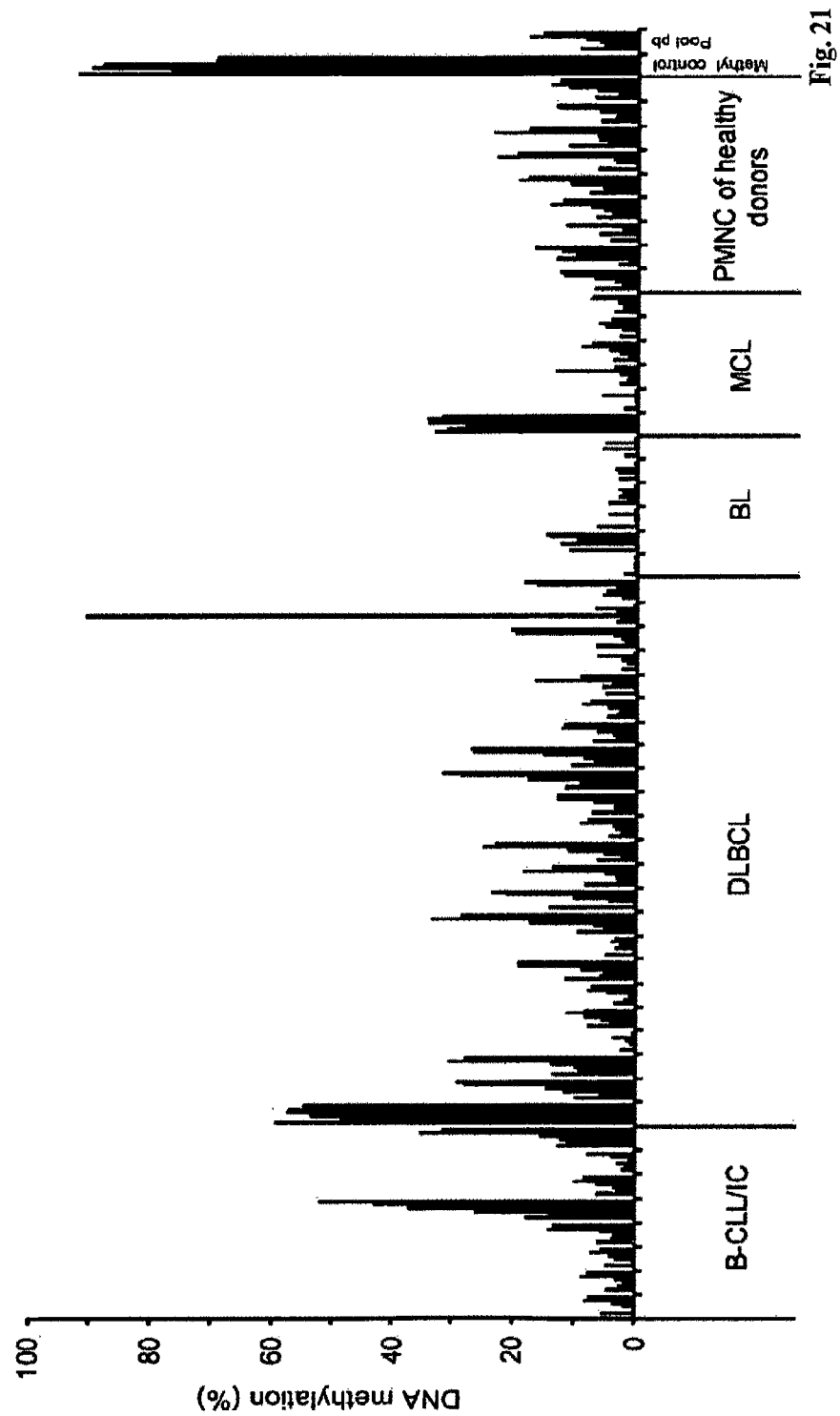

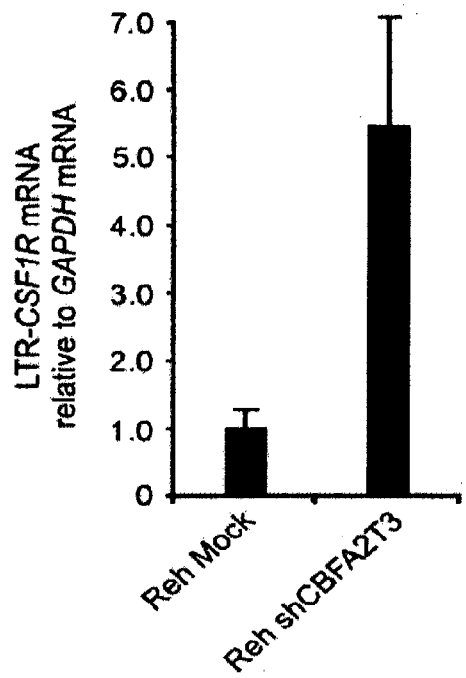
Fig. 22a
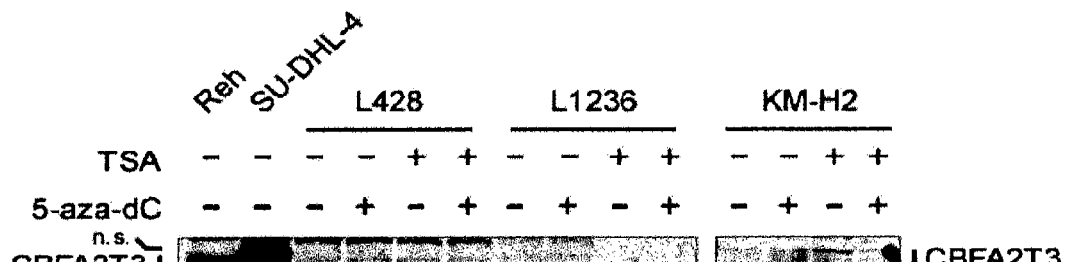
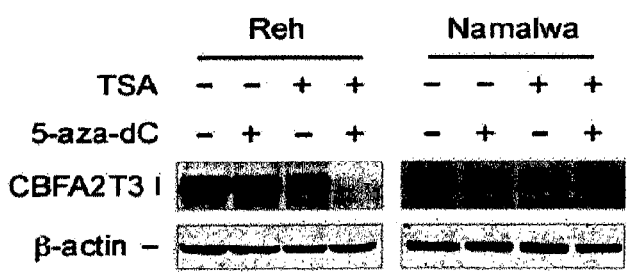
Fig. 22b

Sequence and alignment of Clone 1 (A1) SEQ ID NO 5

CCATGATTGTGAGGCCTCCCTACCCACGTGGAACT/TTACAAGCGGTAATACAAAGAGACA
GGATTATATGATCTCCAAGGTCCCATCCAGCCCATTTAACACG/GCATTGTGGCTCTGGAG
ACCTGGAAGCACTGCTAACTGTTCTCTCGATTTTCTGACGCTCGGCCACATCAACCTGTC
ATACTAGTTGTGAGGAGAAGTCAAGGACAGTGACACAGCCAGCCAGTCTGAGGCATTTTC
CATCATCCTGAAGGAGTTGCCCTATCCTGCTTTTCACTGGAGGGGGCATGGATGG/GGGCT
CCTGACACACTGACCTCTGTCAGTTCCTTCAGCACACCAGGCTAATCCCCAGTCTTGCGC
CTTTGGACCAGAGGTTTTCTTTGCTCAGAATACTGTTTCAACAGATCTTTGCATAGCTGG
CTCTCGCTATTTGACTAAAATGTCAATCCTCAGAGAGGTACTCCTTAAATATCCAATCTT
AAGTAGCATCCCTTTCTCCCAGGATCCTGTTTTCAGAACTCTGTTTTCTTTTTAAAACA
CTTGTTATCTGAAAGGATGTTGTCTGCTTGCTTGTTTGTTCATTTCTTTATTGTCTATTC
CATCTCACCCCTTCTCAGGATGTAAGCTGTTTAAAGGCAAGGACCTTATCTGTGTTACAT
GCTGTATTCCCAGGGCTCAGACAGAGCATGACCTATCGTATGTACTAAATAAATATCTCC
TCATACTGTAAAAAAAAAAAAAAAAAAAAAAAAA

Alignment on chromosome 2:
Exon 1:  192,866,495-192,866,529    (35 bp)
Exon 2:  192,897,297-192,897,364    (68 bp)
Exon 3:  192,899,420-192,899,611    (192 bp)
Exon 4:  192,901,411-192,901,847    (437 bp)

Sequence and alignment of Clone 2 (A3) SEQ ID NO 6

CCATGATTGTGAGGCCTCCCCAGCCATATGGAAAT/ATAATGCAGCAACAAGCTGCCATCTT
GAAAGTGGAGACCAGGACCTTCACAAGACATTGAACCCGACAGCACCTTGATCTTCAACTTC
CCAAGTTCCAAAG/AAAGTTCCTTCAACCTCTGATCACTCAAATAATCCTTGTTCATCTCTG
AAGACCAATTTCAACTTTCAG/GCCTGACTGCACCATCTCCAGCTCTCTGCTTCGGGTTGCT
GACCTCTATGTCCATACCAGCCAGGGTCCCTTTCCCTTTGACTCCTGGTTGGTAAGGCAATG
ATGGAGTATTAGGAGACAGAAGATGAATGAGGTCAAGGCATTTATTTCCATAGTTCTTTTCT
GTGGGGTTGCTAAGGTTGGCTCTCTCAACCACAACTATAATTTCACAGGGAGTACCTTATGA
CCAGTTAATAAAGGAAGAAAAATTGCAAGCTTAGATTAAATAAGAATTCACCGATATGCTAG
CAACTGCTAGCAGTTGCTTCTTTATAACCCTACTGATGCATGGTCCTGCAAGTCAGTGAGTG
AAAGGAAATCGTTCCATCAGGCAGAAATTTAGAGGGGAAATTTGACTGAGCACTGTGTGAAG
GGAGAGATGGCTTGAGGTAGGAACCTGAACTAAACCATGAGCAGTAGCTAACAGGTTCGCCA
GCTGGTAAGGGAACTGCAAAGAACATGATTGGAAAGTTGATGATCAGGAGATCTCATGGAGG
AGTACATTAACAGTCCTCTCGCAACAGGCCCCATGTTCATTAATCAATTAAAAATGTTTGAG
TAAAAAAAAAAAAAAAAAAA

Alignment on chromosome 2:
Exon 1:  155,062,125-155,062,159    (35 bp)
Exon 2:  155,057,018-155,057,118    (101 bp)
Exon 3:  154,990,804-154,990,872    (69 bp)
Exon 4:  154,986,280-154,986,879    (600 bp)

Fig. 24a

Sequence and alignment of Clone 3 (AA3) SEQ ID NO 7

GATTTGAGGCCTCCTCAGCCATGCAGAACT/GTCATTTCAAAGCCTTAGAAACTGGCCTCAA
CAGTAACTGCAGGAAGCATACTTGTCAGATCTGAGCAATAAAAATACACCCTGACTGCTGAG
CCTGGAGCACGGGAGAGCCTACAGCTAACCAGGGAAGACATG/CTTTAGATAAAGTCCTTCC
AACATCTTGCAACCTGGATAACAGCCAAGTCCTATTCATCCCTCTCAACCTGGCTCTTCCAT
GCCCTCCTGCAAGGCCTTCCCCAGCCCTTCTCTGTGGATGCCCCTCCTCCGTTTTGAAGCAG
ACTGGATACCAGCCCCACCCCGCCGCCATGCTTCTTTTATCCTTGCAG/CTTCACTCCTGAG
GCTGGCGAGACCACAAACCCACCAGGAGAAATGAACTCCAGACGGGAAGAATGAACAACTCC
TGATGCACCACCTTAAGAGCTGTAACACGCACCGCCAAGGTTTGCAGATTCACTCCTGAAGC
CAGCGAGACCACGAACCCACCAGAAGGAAGAAACTCTGAACACGTCCAACATCAGAAGGAA
CAAACTCTGGATACGCCATCTTTAAGAACTGTAACACTCACCACGAGGGTCCACGACTTCAT
TCTTGAAGTCAGTGAGACCAAGAACCCACCAATTCTGGACACAATTTCATTTGGTGAGCAGT
CCAGATTACATGTGTGTACACTGTAATGATCAGCTAAGGACTGACTGCCTTTAGCTCCTTCA
CCCGTTCTCACCTCTGAGGTTCAGTAATAAATGGCTCCTACCAACTAACTGAAGTATCAAAA
AAAAAAAAAA

Alignment on chromosome 7:
Exon 1: 130,708,095-130,708,125      (31 bp)
Exon 2: 130,715,937-130,716,071      (135 bp)
Exon 3: 130,727,473-130,727,663      (191 bp)
Exon 4: 130,744,673-130,745,116      (444 bp)

Sequence and alignment of Clone 4 (AA2) SEQ ID NO 8

GATTCTGAGGCCTCCTCAGCCATGTGGAACT/TTTTTTCTAGCTTGTGTTGTGTTTTTAATG
GGAGAGTTGGTCAGCGTCTGCTGGAACAGAGCTACGCCTATGGAACCGTAGACTTGTTCGTG
CTTTATT/GCAATACTTTAAAGACACAAAGTCTCAACAACCATCTTCCGCTTGACGAGACAG
ATCACTCTAATTTGAGCAGAAGCTACTATGTCCTGCCCTTTGAACGCGGCGGCCCGGACAGC
TGACAAGGACACACTGTGTATTTCCATTCCAATTCTGGGAGTGCTCTGAGGCCTCTGGGGGA
GAAGGACCCATGAAATATTCAAAACATAAGTGAATAAAATATCTAGGTGCTAGATATGGGCC
AGGAAGAGCCCTCGGCCCTGCAAAAAAAAAAAAAAAAAAAAAAA

Alignment on chromosome 21:
Exon 1: 47,013,592-47,013,622        (31 bp)
Exon 2: 47,015,477-47,015,575        (99 bp)
Exon 3: 47,016,305-47,016,568        (264 bp)

Fig. 24b

```
                        SEQUENCE LISTING

<160> NUMBER OF SEQ ID NOS: 112

<210> SEQ ID NO 1
<211> LENGTH: 422
<212> TYPE: RNA
<213> ORGANISM: Homo sapiens

<400> SEQUENCE: 1
cucuuuugcc ugccaucaug uuggauguga uucugcuccu ccuuugccuu ccacuaugau      60
ucugaggccu ccucagccau gcugaacugu uuaccuguuc uggauguuuc auauagaugg     120
agucguauga cauuuugcua cuggcuucau ugacuuaaca caguguuuuc aagguucauc     180
cacaguguag cagcuaaaag gggaagaaga ggaucagccc aaggaggagg aagaggaaaa     240
caagacaaac agccagugca gaggagagga acguguguce aguguccega ucccugcgga     300 gcuaguagcu gagagcucug ugcccugggc accuugcagc ccugcaccug ccugccacuu     360
ccccaccgag gccauggggcc caggaguucu gcugcuccug cuguggccaa cagcuuggca     420
ug                                                                    422

<210> SEQ ID NO 2
<211> LENGTH: 422
<212> TYPE: RNA
<213> ORGANISM: Homo sapiens

<400> SEQUENCE: 2
caugccaagc uguggccacc agcaggagca gcagaacucc ugggcccaug gccucggugg      60
ggaaguggca ggcaggugca gggcugcaag gugcccaggg cacagagcuc ucagcuacua     120
gcuccgcagg gaucgggaca cuggacacac guuccucucc ucugcacugg cuguuugucu     180
uguuuuccuc uuccuccucc uugggcugau ccucuucuuc cccuuuuagc ugcuacacug     240
uggaugaacc uugaaaacac uguguuaagu caaugaagcc aguagcaaaa ugucaucgag     300
cuccaucuau augaaacauc cagaacaggu aaacaguuca gcauggcuga ggaggccuca     360
gaaucauagu ggaaggcaaa ggaggagcag aaucacaucc aacaugaugg caggcaaaag     420
```

```
ag                                                                         422

<210> SEQ ID NO 3
<211> LENGTH: 422
<212> TYPE: DNA
<213> ORGANISM: Homo sapiens

<400> SEQUENCE: 3
ctcttttgcc tgccatcatg ttggatgtga ttctgctcct cctttgcctt ccactatgat      60
tctgaggcct cctcagccat gctgaactgt ttacctgttc tggatgtttc atatagatgg     120
agtcgtatga cattttgcta ctggcttcat tgacttaaca cagtgttttc aaggttcatc     180
cacagtgtag cagctaaaag gggaagaaga ggatcagccc aaggaggagg aagaggaaaa     240
caagacaaac agccagtgca gaggagagga acgtgtgtcc agtgtcccga tccctgcgga     300
gctagtagct gagagctctg tgccctgggc accttgcagc cctgcacctg cctgccactt     360
ccccaccgag gccatgggcc caggagttct gctgctcctg ctggtggcca gcttggca      420 tg                                                                       422

<210> SEQ ID NO 4
<211> LENGTH: 422
<212> TYPE: DNA
<213> ORGANISM: Homo sapiens

<400> SEQUENCE: 4
catgccaagc tgtggccacc agcaggagca gcagaactcc tgggcccatg gcctcggtgg      60
ggaagtggca ggcaggtgca gggctgcaag gtgcccaggg cacagagctc tcagctacta     120
gctccgcagg gatcgggaca ctggacacac gttcctctcc tctgcactgg ctgtttgtct     180
tgttttcctc ttcctcctcc ttgggctgat cctcttcttc ccctttagc tgctacactg      240 tggatgaacc ttgaaaacac tgtgttaagt caatgaagcc agtagcaaaa tgtcatacga     300
ctccatctat atgaaacatc cagaacaggt aaacagttca gcatggctga ggaggcctca     360
gaatcatagt ggaaggcaaa ggaggagcag aatcacatcc aacatgatgg caggcaaaag     420
ag                                                                       422

<210> SEQ ID NO 5
<211> LENGTH: 753
<212> TYPE: DNA
<213> ORGANISM: Homo sapiens

<400> SEQUENCE: 5
ccatgattgt gaggcctccc tacccacgtg gaactttaca agcggtaata caaagagaca      60
ggattatatg atctccaagg tcccatccag cccatttaac acggcattgt ggctctggag     120
acctggaagc actgctaact gttctctcga ttttctgacg ctcggccaca tcaacctgtc     180
atactagttg tgaggagaag tcaaggacag tgacacagcc agccagtctg aggcattttc     240
catcatcctg aaggagttgc cctatcctgc ttttcactgg aggggcatg gatgggggct      300 cctgacacac tgacctctgt cagttccttc agcacaccag gctaatcccc agtcttgcgc     360 cttttggacca gaggttttct ttgctcagaa tactgtttca acagatcttt gcatagctgg    420
ctctcgctat ttgactaaaa tgtcaatcct cagagaggta ctccttaaat atccaatctt     480
aagtagcatc cctttctccc aggatcctgt ttttcagaac tctgttttct ttttaaaaca     540
cttgttatct gaaaggatgt tgtctgcttg cttgtttgtt catttcttta ttgtctattc     600
```

```
catctcaccc cttctcagga tgtaagctgt ttaaaggcaa ggaccttatc tgtgttacat    660
gctgtattcc cagggctcag acagagcatg acctatcgta tgtactaaat aaatatctcc    720
tcatactgta aaaaaaaaaa aaaaaaaaaa aaa                                 753

<210> SEQ ID NO 6
<211> LENGTH: 823
<212> TYPE: DNA
<213> ORGANISM: Homo sapiens

<400> SEQUENCE: 6
ccatgattgt gaggcctccc cagccatatg gaaatataat gcagcaacaa gctgccatct     60
tgaaagtgga gaccaggacc ttcacaagac attgaacccg acagcacctt gatcttcaac    120
ttcccaagtt ccaaagaaag ttccttcaac ctctgatcac tcaaataatc cttgttcatc    180
tctgaagacc aatttcaact tcaggcctg actgcaccat ctccagctct ctgcttcggg     240
ttgctgacct ctatgtccat accagccagg gtcccttttcc ctttgactcc tggttggtaa    300
ggcaatgatg gagtattagg agacagaaga tgaatgaggt caaggcattt atttccatag    360
ttcttttctg tggggttgct aaggttggct ctctcaacca caactataat ttcacaggga    420
gtaccttatg accagttaat aaaggaagaa aaattgcaag cttagattaa ataagaattc    480
accgatatgc tagcaactgc tagcagttgc ttctttataa ccctactgat gcatggtcct    540
gcaagtcagt gagtgaaagg aaatcgttcc atcaggcaga aatttagagg ggaaatttga    600
ctgagcactg tgtgaaggga gagatggctt gaggtaggaa cctgaactaa accatgagca    660
gtagctaaca ggttcgccag ctggtaaggg aactgcaaag aacatgattg gaaagttgat    720
gatcaggaga tctcatggag gagtacatta acagtcctct cgcaacaggc cccatgttca    780
ttaatcaatt aaaaatgttt gagtaaaaaa aaaaaaaaaa aaa                      823

<210> SEQ ID NO 7
<211> LENGTH: 814
<212> TYPE: DNA
<213> ORGANISM: Homo sapiens

<400> SEQUENCE: 7
gatttgaggc ctcctcagcc atgcagaact gtcatttcaa agccttagaa actggcctca     60
acagtaactg caggaagcat acttgtcaga tctgagcaat aaaaatacac cctgactgct    120
gagcctggag cacgggagag cctacagcta accagggaag acatgcttta gataaagtcc    180
ttccaacatc ttgcaacctg gataacagcc aagtcctatt catccctctc aacctggctc    240
ttccatgccc tcctgcaagg ccttccccag cccttctctg tggatgcccc tcctccgttt    300
tgaagcagac tggataccag ccccaccccg ccgccatgct tcttttatcc ttgcagcttc    360
actcctgagg ctggcgagac cacaaaccca ccaggagaaa tgaactccag acgggaagaa    420
tgaacaactc ctgatgcacc accttaagag ctgtaacacg caccgccaag gtttgcagat    480
tcactcctga agccagcgag accacgaacc caccagaagg aagaaactct gaacacgtcc    540
gaacatcaga aggaacaaac tctggatacg ccatctttaa gaactgtaac actcaccacg    600
agggtccacg acttcattct tgaagtcagt gagaccaaga acccaccaat tctggacaca    660
atttcatttg gtgagcagtc cagattacat gtgtgtacac tgtaatgatc agctaaggac    720
tgactgcctt tagctccttc acccgttctc acctctgagg ttcagtaata aatggctcct    780
accaactaac tgaagtatca aaaaaaaaaa aaaa                                814
```

<210> SEQ ID NO 8
<211> LENGTH: 414
<212> TYPE: DNA
<213> ORGANISM: Homo sapiens

<400> SEQUENCE: 8

```
gattctgagg cctcctcagc catgtggaac ttttttttcta gcttgtgttg tgtttttaat      60
gggagagttg gtcagcgtct gctggaacag agctacgcct atggaaccgt agacttgttc     120
gtgctttatt gcaatacttt aaagacacaa agtctcaaca accatcttcc gcttgacgag     180
acagatcact ctaatttgag cagaagctac tatgtcctgc cctttgaacg cggcggcccg     240
gacagctgac aaggacacac tgtgtatttc cattccaatt ctgggagtgc tctgaggcct     300
ctgggggaga aggacccatg aaatattcaa acataagtg aataaaatat ctaggtgcta      360
gatatgggcc aggaagagcc ctcggccctg caaaaaaaaa aaaaaaaaaa aaaa            414
```

<210> SEQ ID NO 9
<211> LENGTH: 422
<212> TYPE: DNA
<213> ORGANISM: Homo sapiens

<400> SEQUENCE: 9

```
gagaaaacgg acggtagtac aacctacact aagacgagga ggaaacggaa ggtgatacta      60
agactccgga gggagtcggta cgacttgaca aatggacaag acctacaaag tatatctacc   120
tcagcatact gtaaaacgat gaccgaagta actgaattgt gtcacaaaag ttccaagtag    180
gtgtcacatc gtcgattttc cccttcttct cctagtcggg ttcctcctcc ttctcctttt    240
gttctgtttg tcggtcacgt ctcctctcct tgcacacagg tcacagggct agggacgcct   300
cgatcatcga ctctcgagac acgggacccg tggaacgtcg ggacgtggac ggacggtgaa   360
ggggtggctc cggtacccgg gtcctcaaga cgacgaggac gaccaccggt gtcgaaccgt   420
ac                                                                     422
```

<210> SEQ ID NO 10
<211> LENGTH: 422
<212> TYPE: DNA
<213> ORGANISM: Homo sapiens

<400> SEQUENCE: 10

```
gtacggttcg acaccggtgg tcgtcctcgt cgtcttgagg acccgggtac cggagccacc      60
ccttcaccgt ccgtccacgt cccgacgttc cacgggtccc gtgtctcgag agtcgatgat    120
cgaggcgtcc ctagccctgt gacctgtgtg caaggagagg agacgtgacc gacaaacaga    180
acaaaaggag aaggaggagg aacccgacta ggagaagaag gggaaaatcg acgatgtgac    240
acctacttgg aacttttgtg acacaattca gttacttcgg tcatcgtttt acagtatgct   300
gaggtagata tactttgtag gtcttgtcca tttgtcaagt cgtaccgact cctccggagt    360
cttagtatca ccttccgttt cctcctcgtc ttagtgtagg ttgtactacc gtccgttttc    420
tc                                                                     422
```

<210> SEQ ID NO 11
<211> LENGTH: 181
<212> TYPE: DNA
<213> ORGANISM: Homo sapiens

<400> SEQUENCE: 11

```
aagacaaaca gccagtgcag aggagaggaa cgtgtgtcca gtgtcccgat ccctgcggag      60
```

```
ctagtagctg agagctctgt gccctgggca ccttgcagcc ctgcacctgc ctgccacttc    120
cccaccgagg ccatgggccc aggagttctg ctgctcctgc tggtggccac agcttggcat    180
g                                                                    181
```

<210> SEQ ID NO 12
<211> LENGTH: 19
<212> TYPE: DNA
<213> ORGANISM: Homo sapiens

<400> SEQUENCE: 12

```
gaagtgatcg accacaagc                                                  19
```

<210> SEQ ID NO 13
<211> LENGTH: 18
<212> TYPE: DNA
<213> ORGANISM: Homo sapiens

<400> SEQUENCE: 13

```
gacacgcgac ttgtacca                                                   18
```

<210> SEQ ID NO 14
<211> LENGTH: 11
<212> TYPE: DNA
<213> ORGANISM: Homo sapiens

<400> SEQUENCE: 14

```
gggagttccc c                                                          11
```

<210> SEQ ID NO 15
<211> LENGTH: 11
<212> TYPE: DNA
<213> ORGANISM: Homo sapiens

<400> SEQUENCE: 15

```
ggcctttaac c                                                          11
```

<210> SEQ ID NO 16
<211> LENGTH: 20
<212> TYPE: DNA
<213> ORGANISM: Homo sapiens

<400> SEQUENCE: 16

```
gcgtgctcaa tagtttatgt                                                 20
```

<210> SEQ ID NO 17
<211> LENGTH: 20
<212> TYPE: DNA
<213> ORGANISM: Homo sapiens

<400> SEQUENCE: 17

```
ttaagtcaat gaagccagta                                                 20
```

<210> SEQ ID NO 18
<211> LENGTH: 20
<212> TYPE: DNA
<213> ORGANISM: Homo sapiens

<400> SEQUENCE: 18

```
tgaccccaga tgtagaggat                                                 20
```

<210> SEQ ID NO 19
<211> LENGTH: 18

```
<212> TYPE: DNA
<213> ORGANISM: Homo sapiens

<400> SEQUENCE: 19
ggcaccagat tcgtgtct                                                   18

<210> SEQ ID NO 20
<211> LENGTH: 21
<212> TYPE: DNA
<213> ORGANISM: Homo sapiens

<400> SEQUENCE: 20
ctgggcaaca gagtgaaact g                                               21

<210> SEQ ID NO 21
<211> LENGTH: 21
<212> TYPE: DNA
<213> ORGANISM: Homo sapiens

<400> SEQUENCE: 21
ccctgatgtc ctggcttaca a                                               21

<210> SEQ ID NO 22
<211> LENGTH: 21
<212> TYPE: DNA
<213> ORGANISM: Homo sapiens

<400> SEQUENCE: 22
agaagaggat cagcccaagg a                                               21

<210> SEQ ID NO 23
<211> LENGTH: 19
<212> TYPE: DNA
<213> ORGANISM: Homo sapiens

<400> SEQUENCE: 23
agggatcggg acactggac                                                  19

<210> SEQ ID NO 24
<211> LENGTH: 20
<212> TYPE: DNA
<213> ORGANISM: Homo sapiens

<400> SEQUENCE: 24
tgtgtccagt gtcccgatcc                                                 20

<210> SEQ ID NO 25
<211> LENGTH: 19
<212> TYPE: DNA
<213> ORGANISM: Homo sapiens

<400> SEQUENCE: 25
aagtggcagg caggtgcag                                                  19

<210> SEQ ID NO 26
<211> LENGTH: 18
<212> TYPE: DNA
<213> ORGANISM: Homo sapiens

<400> SEQUENCE: 26
atgggcccag gagttctg                                                   18

<210> SEQ ID NO 27
```

```
<211> LENGTH: 20
<212> TYPE: DNA
<213> ORGANISM: Homo sapiens

<400> SEQUENCE: 27
tccatcacac cccaacaaag                                                    20

<210> SEQ ID NO 28
<211> LENGTH: 21
<212> TYPE: DNA
<213> ORGANISM: Homo sapiens

<400> SEQUENCE: 28
cccagtgata gagcccagtg t                                                  21

<210> SEQ ID NO 29
<211> LENGTH: 18
<212> TYPE: DNA
<213> ORGANISM: Homo sapiens

<400> SEQUENCE: 29
cattccacgc tgccattg                                                      18

<210> SEQ ID NO 30
<211> LENGTH: 21
<212> TYPE: DNA
<213> ORGANISM: Homo sapiens

<400> SEQUENCE: 30
ttttgctact ggcttcattg a                                                  21

<210> SEQ ID NO 31
<211> LENGTH: 20
<212> TYPE: DNA
<213> ORGANISM: Homo sapiens

<400> SEQUENCE: 31
gccttccact atgattctga                                                    20

<210> SEQ ID NO 32
<211> LENGTH: 18
<212> TYPE: DNA
<213> ORGANISM: Homo sapiens

<400> SEQUENCE: 32
cctcctcctt gggctgat                                                      18

<210> SEQ ID NO 33
<211> LENGTH: 19
<212> TYPE: DNA
<213> ORGANISM: Homo sapiens

<400> SEQUENCE: 33
aacactaagc tcgcaatcc                                                     19

<210> SEQ ID NO 34
<211> LENGTH: 20
<212> TYPE: DNA
<213> ORGANISM: Homo sapiens

<400> SEQUENCE: 34
tcacacctat cagtgtggcc                                                    20
```

```
<210> SEQ ID NO 35
<211> LENGTH: 21
<212> TYPE: DNA
<213> ORGANISM: Homo sapiens

<400> SEQUENCE: 35
tgctgttgtt ggtctgtctc c                                           21

<210> SEQ ID NO 36
<211> LENGTH: 21
<212> TYPE: DNA
<213> ORGANISM: Homo sapiens

<400> SEQUENCE: 36
agctgttgtt gcagttcttg c                                           21

<210> SEQ ID NO 37
<211> LENGTH: 17
<212> TYPE: DNA
<213> ORGANISM: Homo sapiens

<400> SEQUENCE: 37
atgctggcgc tgagtac                                                17

<210> SEQ ID NO 38
<211> LENGTH: 18
<212> TYPE: DNA
<213> ORGANISM: Homo sapiens

<400> SEQUENCE: 38
tgagtccttc cacgatac                                               18

<210> SEQ ID NO 39
<211> LENGTH: 22
<212> TYPE: DNA
<213> ORGANISM: Homo sapiens

<400> SEQUENCE: 39
caggagccaa gagtgaagaa ca                                          22

<210> SEQ ID NO 40
<211> LENGTH: 22
<212> TYPE: DNA
<213> ORGANISM: Homo sapiens

<400> SEQUENCE: 40
agctggaaaa cccaacttct gt                                          22

<210> SEQ ID NO 41
<211> LENGTH: 18
<212> TYPE: DNA
<213> ORGANISM: Homo sapiens

<400> SEQUENCE: 41
cgagcacctc agcaaacg                                               18

<210> SEQ ID NO 42
<211> LENGTH: 20
<212> TYPE: DNA
<213> ORGANISM: Homo sapiens

<400> SEQUENCE: 42
gggcccttct ttgtgtcctc                                             20
```

```
<210> SEQ ID NO 43
<211> LENGTH: 31
<212> TYPE: DNA
<213> ORGANISM: Homo sapiens

<400> SEQUENCE: 43
gtgagttttt gtggagggat agatggttgg a                              31

<210> SEQ ID NO 44
<211> LENGTH: 37
<212> TYPE: DNA
<213> ORGANISM: Homo sapiens

<400> SEQUENCE: 44 ccccaccctaa actaaaacca caaacctaac aactacc                       37

<210> SEQ ID NO 45
<211> LENGTH: 22
<212> TYPE: DNA
<213> ORGANISM: Homo sapiens

<400> SEQUENCE: 45
cccacaaaat aataaaaaa ta                                         22

<210> SEQ ID NO 46
<211> LENGTH: 15
<212> TYPE: DNA
<213> ORGANISM: Homo sapiens

<400> SEQUENCE: 46
ccccccacca accta                                                15

<210> SEQ ID NO 47
<211> LENGTH: 40
<212> TYPE: DNA
<213> ORGANISM: Homo sapiens

<400> SEQUENCE: 47
tttgtaggta gttgttaggt ttgtggtttt agttagggtg                     40

<210> SEQ ID NO 48
<211> LENGTH: 28
<212> TYPE: DNA
<213> ORGANISM: Homo sapiens

<400> SEQUENCE: 48
caaacccaac cctccccct tcaaatct                                   28

<210> SEQ ID NO 49
<211> LENGTH: 19
<212> TYPE: DNA
<213> ORGANISM: Homo sapiens

<400> SEQUENCE: 49
taggaggttt ttagggtag                                            19

<210> SEQ ID NO 50
<211> LENGTH: 29
<212> TYPE: DNA
<213> ORGANISM: omo sapiens

<400> SEQUENCE: 50
tgggaggagg aagttgttgg aaggttaaa                                 29
```

<210> SEQ ID NO 51
<211> LENGTH: 39
<212> TYPE: DNA
<213> ORGANISM: Homo sapiens

<400> SEQUENCE: 51
cctaaaaaac ccaaaccctc cccaccacca actaaatat                              39

<210> SEQ ID NO 52
<211> LENGTH: 21
<212> TYPE: DNA
<213> ORGANISM: Homo sapiens

<400> SEQUENCE: 52
aaaaaaatct ccctacaacc t                                                 21

<210> SEQ ID NO 53
<211> LENGTH: 23
<212> TYPE: DNA
<213> ORGANISM: Homo sapiens

<400> SEQUENCE: 53
aggtggtggg gtgggggtag aga                                               23

<210> SEQ ID NO 54
<211> LENGTH: 24
<212> TYPE: DNA
<213> ORGANISM: Homo sapiens

<400> SEQUENCE: 54
ctcaccaacc cacctacccc aact                                              24

<210> SEQ ID NO 55
<211> LENGTH: 15
<212> TYPE: DNA
<213> ORGANISM: Homo sapiens

<400> SEQUENCE: 55
gggtgggggt agaga                                                        15

<210> SEQ ID NO 56
<211> LENGTH: 21
<212> TYPE: DNA
<213> ORGANISM: Homo sapiens

<400> SEQUENCE: 56
ctactagctc cgcagggatc g                                                 21

<210> SEQ ID NO 57
<211> LENGTH: 23
<212> TYPE: DNA
<213> ORGANISM: Homo sapiens

<400> SEQUENCE: 57
acacgttcct ctcctctgca ctg                                               23

<210> SEQ ID NO 58
<211> LENGTH: 28
<212> TYPE: DNA
<213> ORGANISM: Homo sapiens

<400> SEQUENCE: 58

```
ctctcctctg cactggctgt ttgtcttg                                    28

<210> SEQ ID NO 59
<211> LENGTH: 19
<212> TYPE: DNA
<213> ORGANISM: Homo sapiens

<400> SEQUENCE: 59
atctgttacc tgggtcact                                              19

<210> SEQ ID NO 60
<211> LENGTH: 23
<212> TYPE: DNA
<213> ORGANISM: Homo sapiens

<400> SEQUENCE: 60
agatcactat gggccagcgg aag                                         23

<210> SEQ ID NO 61
<211> LENGTH: 28
<212> TYPE: DNA
<213> ORGANISM: Homo sapiens

<400> SEQUENCE: 61
atgggccagc ggaagcgaag ttaaacag                                    28

<210> SEQ ID NO 62
<211> LENGTH: 29
<212> TYPE: DNA
<213> ORGANISM: Homo sapiens

<400> SEQUENCE: 62
gctctcttgc ctgccgccat gtaagacgt                                   29

<210> SEQ ID NO 63
<211> LENGTH: 29
<212> TYPE: DNA
<213> ORGANISM: Homo sapiens

<400> SEQUENCE: 63
tttctttgcc tgctgtcatt catgtaaga                                   29

<210> SEQ ID NO 64
<211> LENGTH: 29
<212> TYPE: DNA
<213> ORGANISM: Homo sapiens

<400> SEQUENCE: 64 attctcccttt gtctgtcgcc atgtaagac                                  29

<210> SEQ ID NO 65
<211> LENGTH: 29
<212> TYPE: DNA
<213> ORGANISM: Homo sapiens

<400> SEQUENCE: 65
tttctttgcc tgccaccatc cacataaga                                   29

<210> SEQ ID NO 66
<211> LENGTH: 29
<212> TYPE: DNA
<213> ORGANISM: Homo sapiens

<400> SEQUENCE: 66
```

-continued

```
ctcattttct cttgccacag ccatgaaag                                              29

<210> SEQ ID NO 67
<211> LENGTH: 29
<212> TYPE: DNA
<213> ORGANISM: Homo sapiens

<400> SEQUENCE: 67 aaggggagt tttcctgcac aagatctct                                               29

<210> SEQ ID NO 68
<211> LENGTH: 29
<212> TYPE: DNA
<213> ORGANISM: Homo sapiens

<400> SEQUENCE: 68
tctcttgctg ccgccgtgta agaaggacc                                              29

<210> SEQ ID NO 69
<211> LENGTH: 29
<212> TYPE: DNA
<213> ORGANISM: Homo sapiens

<400> SEQUENCE: 69
tctcttaact gctgccatgt aagacacgc                                              29

<210> SEQ ID NO 70
<211> LENGTH: 20
<212> TYPE: DNA
<213> ORGANISM: Homo sapiens

<400> SEQUENCE: 70
ccatgattgt gaggcctccc                                                        20

<210> SEQ ID NO 71
<211> LENGTH: 41
<212> TYPE: DNA
<213> ORGANISM: Homo sapiens

<400> SEQUENCE: 71
ccatgattgt gaggcctccc tacccacgtg gaactgtgag t                                41

<210> SEQ ID NO 72
<211> LENGTH: 35
<212> TYPE: DNA
<213> ORGANISM: Homo sapiens

<400> SEQUENCE: 72
tacagttaca agcggtaata caaagagaca ggatt                                       35

<210> SEQ ID NO 73
<211> LENGTH: 41
<212> TYPE: DNA
<213> ORGANISM: Homo sapiens

<400> SEQUENCE: 73
ccatgattgt gaggcctccc cagccatatg gaaatgtaag t                                41

<210> SEQ ID NO 74
<211> LENGTH: 35
<212> TYPE: DNA
<213> ORGANISM: Homo sapiens
```

<400> SEQUENCE: 74
tccagataat gcagcaacaa gctgccatct tgaaa        35

<210> SEQ ID NO 75
<211> LENGTH: 29
<212> TYPE: DNA
<213> ORGANISM: Homo sapiens

<400> SEQUENCE: 75
gcttgccacc atgtaagatg tgactttgc        29

<210> SEQ ID NO 76
<211> LENGTH: 37
<212> TYPE: DNA
<213> ORGANISM: Homo sapiens

<400> SEQUENCE: 76
gttcctgagg cctccccagc catgcagaac tgtgagt        37

<210> SEQ ID NO 77
<211> LENGTH: 37
<212> TYPE: DNA
<213> ORGANISM: Homo sapiens

<400> SEQUENCE: 77
tgaaggtcat ttcaaagcct tagaaactgg cctcaac        37

<210> SEQ ID NO 78
<211> LENGTH: 37
<212> TYPE: DNA
<213> ORGANISM: Homo sapiens

<400> SEQUENCE: 78
gattctgagg cctccccagc catgtggaac tgtaagt        37

<210> SEQ ID NO 79
<211> LENGTH: 37
<212> TYPE: DNA
<213> ORGANISM: Homo sapiens

<400> SEQUENCE: 79
gatagttttt tctagcttgt gttgtgtttt taatggg        37

<210> SEQ ID NO 80
<211> LENGTH: 20
<212> TYPE: DNA
<213> ORGANISM: Homo sapiens

<400> SEQUENCE: 80
ctctgctcct cctgttcgac        20

<210> SEQ ID NO 81
<211> LENGTH: 20
<212> TYPE: DNA
<213> ORGANISM: Homo sapiens

<400> SEQUENCE: 81
ttaaaagcag ccctggtgac        20

<210> SEQ ID NO 82
<211> LENGTH: 20
<212> TYPE: DNA

```
<400> SEQUENCE: 82
taggtggaga taattgaatt                                              20

<210> SEQ ID NO 83
<211> LENGTH: 23
<212> TYPE: DNA
<213> ORGANISM: Homo sapiens

<400> SEQUENCE: 83
cacatataca tttacaacaa tct                                          23

<210> SEQ ID NO 84
<211> LENGTH: 17
<212> TYPE: DNA
<213> ORGANISM: Homo sapiens

<400> SEQUENCE: 84
tataaaacca tcaaatc                                                 17

<210> SEQ ID NO 85
<211> LENGTH: 19
<212> TYPE: DNA
<213> ORGANISM: Homo sapiens

<400> SEQUENCE: 85
catggctggg gaggcctca                                               19

<210> SEQ ID NO 86
<211> LENGTH: 18
<212> TYPE: DNA
<213> ORGANISM: Homo sppiens

<400> SEQUENCE: 86
catggctgag aggcctca                                                18

<210> SEQ ID NO 87
<211> LENGTH: 24
<212> TYPE: DNA
<213> ORGANISM: Homo sapiens

<400> SEQUENCE: 87
aattcagatc tcccgggtca ccgc                                         24

<210> SEQ ID NO 88
<211> LENGTH: 27
<212> TYPE: DNA
<213> ORGANISM: Homo sapiens

<400> SEQUENCE: 88
gcggtgaccc gggagatctg aattccc                                      27

<210> SEQ ID NO 89
<211> LENGTH: 25
<212> TYPE: DNA
<213> ORGANISM: Homo sapiens

<400> SEQUENCE: 89
gcggtgaccc gggagatctg aattc                                        25

<210> SEQ ID NO 90
<211> LENGTH: 20
<212> TYPE: DNA
```

<213> ORGANISM: Homo sapiens

<400> SEQUENCE: 90
gggaggcctc acaatcatgg                                               20

<210> SEQ ID NO 91
<211> LENGTH: 20
<212> TYPE: DNA
<213> ORGANISM: Homo sapiens

<400> SEQUENCE: 91
aggaggcctc agaatcatag                                               20

<210> SEQ ID NO 92
<211> LENGTH: 20
<212> TYPE: DNA
<213> ORGANISM: Homo sapiens

<400> SEQUENCE: 92
aggtgtggtg ccagattttc                                               20

<210> SEQ ID NO 93
<211> LENGTH: 24
<212> TYPE: DNA
<213> ORGANISM: Homo sapiens

<400> SEQUENCE: 93
tttgaatgat gagccttcgt gccc                                          24

<210> SEQ ID NO 94
<211> LENGTH: 621
<212> TYPE: DNA
<213> ORGANISM: Homo sapiens

<400> SEQUENCE: 94
ttttcatagt gcagtagttc ccccttattg gcaatttcag ttacttgtga tcaatccatg   60
tccaaaaata tgaaggtact ttgagagaga gagagagact acattcacgt ggcttttatc  120
acagtgtagt gttataattg tcttattgta ttattagtta ttattgttga tctcttactt  180
tgcctaactg ataaacttta tcataggtat gtaggtgata tggtttggct gtgtccccac  240
ccaattctca ccttgaattg taataattcc cacatgtcaa gggtgggcc aggtggagat   300
aattgaatca tgggggcagt tttccccata ctgttcctcg tggtagtgat taagtctcac  360
gagatctgat ggttttataa atgggagttc ccctgcatat actcttttgc ctgccatcat  420
gttggatgtg attctgctcc tcctttgcct tccactatga ttctgaggcc tcctcagcca  480
tgctgaactg tgagtcaatt aaacctcctt tcctttagaa atcacccagt cttgggtatg  540
tctttattag cagtatgaga acagactaat acagtaggta taggaaaaaa acatggcata  600
tacagggttt agtactatct g                                            621

<210> SEQ ID NO 95
<211> LENGTH: 193
<212> TYPE: DNA
<213> ORGANISM: Homo sapiens

<400> SEQUENCE: 95
tgatatggtt tggctgtgtc cccacccaaa tctcatcttg aattgtagct cccataattc    60
ccacgtgtcg tgggagggac ccggtgggag gtaattgaat catgggggcg ggtctttccc   120
gtgctgttct cgtgatagtg aataagtctc acgagatctg atggttttat aaaggggagt   180

| | |
|---|---|
| tcccctgcac awg | 193 |

<210> SEQ ID NO 96
<211> LENGTH: 186
<212> TYPE: DNA
<213> ORGANISM: Homo sapiens

<400> SEQUENCE: 96

| | |
|---|---|
| tgatatggtt tggctgtgtc cccacccaat tctcaccttg aattgtaata attcccacat | 60 |
| gtcaagggtg gggccaggtg gagataattg aatcatgggg gcagttttcc ccatactgtt | 120 |
| ctcgtggtag tgattaagtc tcacgagatc tgatggtttt ataaatggga gttcccctgc | 180 |
| atatac | 186 |

<210> SEQ ID NO 97
<211> LENGTH: 191
<212> TYPE: DNA
<213> ORGANISM: Homo sapiens

<400> SEQUENCE: 97

| | |
|---|---|
| tgatatggtt tggctctgag tcccctgcca aatctcattt cgtagctccc ataattctcg | 60 |
| tgtgttgtgg gagggacctg gtgggagatg attgaatcat gggggcaggt ctttccagtg | 120 |
| ctgttcttgc gacagtgaat gggtctcgcg agatctgatg gttttaaaaa cgggtttctc | 180 |
| tacacaagct c | 191 |

<210> SEQ ID NO 98
<211> LENGTH: 198
<212> TYPE: DNA
<213> ORGANISM: Homo sapiens

<400> SEQUENCE: 98

| | |
|---|---|
| tgatatgctt tggctgtgtc tccacccaaa tcttatcttg aattgtagct ttcgtaattc | 60 |
| ccacgtgttg tgggagggac ctggtgggag atacctgaat cgaatcgttg ggggagtttc | 120 |
| cccaatactg ttcttgcgac agtgaatggg tctcgcgaga tctgatggtt ttaaaaacgg | 180 |
| gtttctctac acaagctc | 198 |

<210> SEQ ID NO 99
<211> LENGTH: 182
<212> TYPE: DNA
<213> ORGANISM: Homo sapiens

<400> SEQUENCE: 99

| | |
|---|---|
| gatatggttt ggctgtgtct ccaaccaaat ctcatcttga attgtagctc ccataattcc | 60 |
| tagcggtgtt gtgggagatc attgaatcat ggggcggttt cccacatact gttctcgtgg | 120 |
| tggtgcataa gtctcacgag atctgatggt tttataaggg gtttcccttt gcttggcttt | 180 |
| tc | 182 |

<210> SEQ ID NO 100
<211> LENGTH: 182
<212> TYPE: DNA
<213> ORGANISM: Homo sapiens

<400> SEQUENCE: 100

| | |
|---|---|
| tgatatagtt tagctgtgtc cccacccata tctcatcgtg aattccatgt cttgtgggag | 60 |
| ggactctgtg ggaggaattg aatcatgggg gcaggtctttt tgtgtgctgt tctcatgata | 120 |

```
gtgaataagt ctcataagat ctggtggttt tataagggg agtttccctg cacaagctct    180
ct                                                                  182
```

<210> SEQ ID NO 101
<211> LENGTH: 184
<212> TYPE: DNA
<213> ORGANISM: Homo sapiens

<400> SEQUENCE: 101

```
tgtccccacc caaagctcat ctggaattgt agctcccaca attcccacat gttgtgggag    60
ggacccggtg ggaggtaatt gaatcatggg gcgtgtcttt tctgtgctgt tctcgtgata   120
gtgaataagt ctcatgagat ctgatggttt tataagggg agttttcctg cacaagatct   180
ctct                                                                184
```

<210> SEQ ID NO 102
<211> LENGTH: 193
<212> TYPE: DNA
<213> ORGANISM: Homo sapiens

<400> SEQUENCE: 102

```
atatggtttg gccctgtgtc tccacccaaa tctcactttg aattgtaata atccccacat    60
gtccagggca gggtcaggca gagttaatgg aatcatgagg gtggtttccc ccatgctgtt   120
cttgtggtag tgaataagtc tcatgagagc tgatggtttt ataaattgga gtccccttgc   180
acaagctctc ttg                                                      193
```

<210> SEQ ID NO 103
<211> LENGTH: 199
<212> TYPE: DNA
<213> ORGANISM: Homo sapiens

<400> SEQUENCE: 103

```
gatatggttt ggctgtgtcc ccattcaaat ttcaactgaa ttgtatcgcc cagaattccc    60
acatgttatg ggagggaccc aggggaggt aattgaatca tggggccag tctttcccat    120 gctattccgt gatattgaat aagtctcaca agatctggtg ggtttatcag gggttctgc   180 ttttgcttct tcctcagtt                                                199
```

<210> SEQ ID NO 104
<211> LENGTH: 208
<212> TYPE: DNA
<213> ORGANISM: Homo sapiens

<400> SEQUENCE: 104

```
tgatatggtt tggctgtgtc ctcaccaaaa tctcaacttg aattgtatct cccagaattc    60
ccatgtgttg tgggagggac ccggggggagg tagcttaatc atggggctg gtctttcctg   120 tgttcttctc atgatagtga ataagtctca cgaataagtc tcacgagatc tgatgggttt   180
atctggggtt tctgttttg cttcttcc                                       208
```

<210> SEQ ID NO 105
<211> LENGTH: 357
<212> TYPE: DNA
<213> ORGANISM: Homo sapiens

<400> SEQUENCE: 105

```
tgatatggtt tggctgtgtc cccacccaat tctcaccttg aattgtaata attcccacat    60
gtcaagggtg gggccaggtg gagataattg aatcatgggg gcagttttcc ccatactgtt   120
```

```
ctcgtggtag tgattaagtc tcacgagatc tgatggtttt ataaatggga gttccctgc     180 atatactctt tgcctgcca tcatgttgga tgtgattctg ctcctccttt gccttccact    240
atgattctga ggcctcctca gccatgctga actgtgagtc aattaaacct cctttccttt   300
agaaatcacc cagtcttggg tatgtcttta ttagcagtat gagaacagac taataca     357
```

<210> SEQ ID NO 106
<211> LENGTH: 362
<212> TYPE: DNA
<213> ORGANISM: Homo sapiens

<400> SEQUENCE: 106

```
tgatatggtt tggctgtgtc cccacccaaa tctcatcttg aattgtagct cccataattc    60
ccacatgtca agggtggggc caggtggaga taattgaatc atgggggcag ttttccccat   120
actgttctcg tgatagtgaa taagtctcac gagatctgat ggttttataa aggggagttc   180
ccctgcacaw gctctcttgc ctgccgccat gtaagacgtg mctttgctcc tccttcgcct   240
tccgccatga ttgtgaggcc tccccagcca tgtggaactg tgagtccatt aaacctcttt   300
cctttataaa ttacccagtc tcgggtatgt ctttattagc agcgtgagaa cagactaata   360
ca                                                                  362
```

<210> SEQ ID NO 107
<211> LENGTH: 115
<212> TYPE: DNA
<213> ORGANISM: Homo sapiens

<400> SEQUENCE: 107

```
tccctgcac awgctctctt gcctgccgcc atgtaagacg tgmctttgct cctccttcgc     60
cttccgccat gattgtgagg cctccccagc catgtggaac tgtgagtcca ttaaa        115
```

<210> SEQ ID NO 108
<211> LENGTH: 115
<212> TYPE: DNA
<213> ORGANISM: Homo sapiens

<400> SEQUENCE: 108

```
tccctgcat atactctttt gcctgccatc atgttggatg tgattctgct cctcctttgc     60
cttccactat gattctgagg cctcctcagc catgctgaac tgtgagtcaa ttaaa        115
```

<210> SEQ ID NO 109
<211> LENGTH: 24
<212> TYPE: DNA
<213> ORGANISM: Homo sapiens

<400> SEQUENCE: 109

```
gattgtgagg cctccccagc catg                                           24
```

<210> SEQ ID NO 110
<211> LENGTH: 20
<212> TYPE: DNA
<213> ORGANISM: Homo sapiens

<400> SEQUENCE: 110

```
ccatgattgt gaggcctccc                                                20
```

<210> SEQ ID NO 111
<211> LENGTH: 20
<212> TYPE: DNA

```
<213> ORGANISM: Homo sapiens

<400> SEQUENCE: 111
ctatgattct gaggcctcct                                              20

<210> SEQ ID NO 112
<211> LENGTH: 24
<212> TYPE: DNA
<213> ORGANISM: Homo sapiens

<400> SEQUENCE: 112
gattctgagg cctcctcagc catg                                         24
```

POLYNUCLEOTIDES FOR MEDICAL USE

RELATED APPLICATIONS

This application claims the benefit of International Patent Application No. PCT/EP2010/003714 filed on Jun. 21, 2010; European Patent Application No. filed on Apr. 30, 2010 and European Patent Application No. 09008082.1 filed on Jun. 19, 2010 the disclosures of which are hereby incorporated by reference in their entireties.

TECHNICAL FIELD

The invention refers to polynucleotides, in particular for medical use. The polynucleotides are in particular RNA and DNA molecules with a sequence that encodes for colony stimulating factor 1 receptor (CSF1R) with an unusual 5' untranslated region, which is generated in diseased cells due to an altered regulatory transcription mechanism of CSF1R. These polynucleotides are present in diseased cells, which aberrantly overexpress CSF1R, i.e. they are not found in their normal counterparts. Therefore, the present invention refers in one embodiment to a method for detecting a disease that involves an overexpression of CSF1R in a subject from a biological sample. Such diseases are cancer, in particular malignant hematological diseases, such as lymphoma (e.g. Hodgkin lymphoma and anaplastic large cell lymphoma), and mammary carcinoma.

INTRODUCTION

Normal cell differentiation terminates at differentiation stages that display a unique and identifiable gene expression program. This process is disturbed in cancer cells, which might lead to the epigenetic silencing of genes detrimental to tumor growth (Esteller, 2002; Jones and Baylin, 2002), but also to the activation of lineage-inappropriate genes (Bagg, 2007; Prindull and Zipori, 2004). As differentiation stages during maturation of hematopoietic lineages are well defined, the hematopoietic system has been particularly informative for investigating such processes. Lineage-inappropriate gene expression is well established in certain hematopoietic malignancies and might be involved in their pathogenesis and progression (Borowitz et al., 2008; Feldman et al., 2008; Legrand et al., 1998).

The most prominent example of reprogramming of the normal gene expression pattern among human lymphomas is classical Hodgkin lymphoma (HL) (Janz et al., 2006; Küppers, 2009). HL is a common lymphoma that usually originates from mature B cells. However, the malignant Hodgkin-/Reed-Sternberg (HRS) cells of HL have almost completely lost the expression of B cell-specific genes (Küppers, 2009; Küppers et al., 2003). This is puzzling at first sight, since mature B cells normally require B cell receptor (BCR) signaling to survive, suggesting that survival of HRS cells is regulated by different means. Indeed, various genes normally suppressed in B cells (in the following referred to as non-B lineage genes) are expressed in HRS cells, resulting in a unique phenotype among human lymphomas (Küppers, 2009; Mathas et al., 2006).

Normal B cell differentiation and B lineage commitment critically depend on the transcription factors E2A, EBF and PAX5 (Nutt and Kee, 2007). Work with mice has shown that these factors not only activate expression of B cell-specific genes, but also repress transcription of non-B lineage genes and thus alternative cellular fates (Nutt and Kee, 2007). The molecular details of how the normal B cell gene expression program is subverted in HRS cells is still poorly understood. Both loss of lineage-specific transcription factors and epigenetic modification of B lineage genes have been implicated in this process (Ehlers et al., 2008; Jundt et al., 2002; Ushmorov et al., 2006). It was shown recently that HRS cells overexpress the helix-loop-helix (HLH) proteins Id2 and ABF-1 which functionally disrupt the activity of the B cell-determining transcription factor E2A (Mathas et al., 2006). Such a functional block could result in a similar cellular plasticity as seen in Pax5-deleted B lymphoid cells, which can develop into other cellular lineages (Nutt and Kee, 2007), and could explain the unusual cellular phenotype of HRS cells. In mice, such plasticity is linked to malignant transformation, since deletion of Pax5 in mature B cells results in the formation of re-differentiated hematopoietic progenitor cell tumors (Cobaleda et al., 2007), and ectopic PAX5 expression in T cells exerts an oncogenic function (Souabni et al., 2007).

The lymphoid-to-myeloid lineage switch in PAX5- and E2A-deficient cells (Ikawa et al., 2004; Nutt and Kee, 2007) may be linked to de-repression of the myeloid-specific gene CSF1R (also called c-fms) (Tagoh et al., 2006). CSF1R is expressed at low level in hematopoietic stem cells (HSCs) and is up-regulated during macrophage differentiation (Bonifer and Hume, 2008), where it is essential for survival and proliferation (Dai et al., 2002). During B lymphopoiesis, expression of CSF1R is progressively silenced, whereby PAX5-mediated repression of its promoter plays a crucial role (Bonifer and Hume, 2008; Tagoh et al., 2006). CSF1R signaling might act in a myeloid-lineage instructive manner to support the lymphoid-to-myeloid switch (Borzillo et al., 1990), however, a direct role of CSF1R re-activation in lymphoid-to-myeloid trans-differentiation has not yet been demonstrated. CSF1R also is amongst the de-repressed non-B lineage genes in HRS cells (Mathas et al., 2006), but neither the cause nor the functional consequences of its expression in these cells are known.

The inventors have found that HRS cell survival depends on CSF1R signaling. Furthermore, it is demonstrated that aberrant CSF1R expression is not activated by its bona fide promoter, but instead expression is driven by an aberrantly activated long terminal repeat (LTR) promoter. This aberrant activation is due to loss of the repressive activity of the MTG/ETO family member CBFA2T3, suggesting a driving role of lost epigenetic silencing of repeat elements in HL pathogenesis.

SUMMARY OF THE INVENTION

The invention provides an RNA molecule transcribed from a long terminal repeat (LTR) sequence, including: a sequence encoding a gene, such as CSF1R, and a sequence that is at least in part found in the LTR, in particular for detecting cancer in a subject. In one embodiment, the RNA molecule includes a sequence that is at least in part found in the LTR is located at a 5' portion of the RNA molecule. In another embodiment the LTR of the RNA molecule includes at least one binding site for a transcription factor chosen from NF-kappa B, SP-1, and AP-1. In another embodiment the LTR sequence includes a sequence from a THE1 family of LTRs, in particular from THE1A, THE1B, THE1C, and THE1D.

The invention also provides a DNA molecule, including a sequence corresponding to an RNA molecule transcribed from a long terminal repeat (LTR) sequence, including: a sequence encoding a gene, such as CSF1R, and a sequence that is at least in part found in the LTR, in particular for detecting cancer in a subject.

The invention also provides a use of an RNA molecule transcribed from a long terminal repeat (LTR) sequence, including: a sequence encoding a gene, such as CSF1R, and a sequence that is at least in part found in the LTR, in particular for detecting cancer in a subject. Also provided is a use of a DNA molecule including a sequence corresponding to an RNA molecule transcribed from a long terminal repeat (LTR) sequence, including: a sequence encoding a gene, such as CSF1R, and a sequence that is at least in part found in the LTR, in particular for diagnosing, monitoring, and/or prognosing cancer in a subject.

The invention also provides a method for diagnosing, monitoring, and/or prognosing cancer based on a biological sample, wherein the cancer involves the expression of an RNA molecule transcribed from a long terminal repeat (LTR) sequence, including: a sequence encoding a gene, such as CSF1R, and a sequence that is at least in part found in the LTR, in particular for detecting cancer in a subject; the method includes:
  detecting the presence or absence of the RNA molecule in the biological sample such as through performing an amplification reaction (e.g. polymerase chain reaction, such as a real time polymerase chain reaction; and ligase chain reaction), or using a microarray, and
  deducing from the presence of the RNA molecule that the subject suffers from cancer. The cancer detected can be a malignant hematological disease, in particular wherein the malignant hematological disease is selected from Hodgkin lymphoma and anaplastic large cell lymphoma.

The invention also provides a vector including an RNA sequence transcribed from a long terminal repeat (LTR) sequence, including: a sequence encoding a gene, such as CSF1R, and a sequence that is at least in part found in the LTR; or a DNA sequence corresponding to an RNA molecule transcribed from a long terminal repeat (LTR) sequence, including: a sequence encoding a gene, such as CSF1R, and a sequence that is at least in part found in the LTR; wherein each of the RNA and DNA sequences includes a sequence of SEQ ID NOs 3 to 8. The sequences of SEQ ID NO 3 to 8 may be operatively linked to an expression control sequence allowing expression in a prokaryotic or a eukaryotic host cell. Also provides is a prokaryotic host cell genetically engineered with a sequence of SEQ ID NO 3 to 8 or with the vector as described above.

The invention also provides a kit for detecting a disease that involves an expression of an RNA sequence transcribed from a long terminal repeat (LTR) sequence, including: a sequence encoding a gene, such as CSF1R, and a sequence that is at least in part found in the LTR; or a DNA sequence corresponding to an RNA molecule transcribed from a long terminal repeat (LTR) sequence, including: a sequence encoding a gene, such as CSF1R, and a sequence that is at least in part found in the LTR; wherein each of the RNA and DNA sequences includes a sequence of SEQ ID NOs 3 to 8; wherein the kit further includes:
  a primer for amplifying a nucleic acid fragment comprising a sequence encoding a portion of the CSF1R gene, such as CSF1R, and
  a sequence that is at least in part found in the LTR.

The invention also provides a method for decreasing in a cell the number of an RNA molecule transcribed from a long terminal repeat (LTR) sequence, that include: a sequence encoding a gene, such as CSF1R, and a sequence that is at least in part found in the LTR, or a DNA molecule, including a sequence corresponding to an RNA molecule transcribed from a long terminal repeat (LTR) sequence, including: a sequence encoding a gene, such as CSF1R, and a sequence that is at least in part found in the LTR;
  Wherein the method includes: introducing into the cell or generating in the cell a means for decreasing the number of molecules in the cell. The means for decreasing the number of RNA or DNA molecules with a sequence of SEQ ID NO. 1 to 8 may be an siRNA or an antisense RNA.

The invention also provides a method for treating a patient suffering from cancer that involves an expression in a cell of molecules of RNA transcribed from a long terminal repeat (LTR) sequence, that include: a sequence encoding a gene, such as CSF1R, and a sequence that is at least in part found in the LTR; or a DNA molecule, including a sequence corresponding to an RNA molecule transcribed from a long terminal repeat (LTR) sequence, including: a sequence encoding a gene, such as CSF1R, and a sequence that is at least in part found in the LTR; wherein the method includes administering to the patient an effective amount of a means for decreasing the number of molecules in the cell. The means for decreasing the number of RNA or DNA molecules with a sequence of SEQ ID NO. 1 to 8 may be an siRNA or an antisense RNA.

The invention also provides a pharmaceutical composition, comprising a means for decreasing in a cell the number of RNA or DNA molecules with a sequence of SEQ ID NO. 1 to 8. The means for decreasing the number of RNA or DNA molecules with a sequence of SEQ ID NO. 1 to 8 may be an siRNA or an antisense RNA.

DESCRIPTION OF THE INVENTION

Generally, the invention refers to polynucleotides as described herein, in particular for medical use. The polynucleotides are in particular RNA and DNA molecules with a sequence that encodes for colony stimulating factor 1 receptor (CSF1R) with an unusual 5' untranslated region, which is generated in diseased cells due to an altered regulatory transcription mechanism of CSF1R. These polynucleotides are present in diseased cells, which aberrantly overexpress CSF1R, i.e. they are not found in their normal counterparts. Therefore, the present invention refers in one aspect to a method for detecting a disease that involves an overexpression of CSF1R in a subject from a biological sample. Such diseases are in particular cancer, e.g. malignant hematological diseases, such as lymphoma (e.g. Hodgkin lymphoma and anaplastic large cell lymphoma), and mamma carcinoma.

In a first aspect, the invention refers to an RNA molecule (RNA fusion transcript) that is transcribed form a long terminal repeat (LTR) sequence, comprising
  a sequence encoding an endogenous gene, such as CSF1R, in particular at a 3' portion or at a 5' portion, and
  a sequence that is at least in part found in the LTR, in particular at a 5' portion of the RNA molecule, in particular for detecting cancer in a subject.

The sequence of the RNA molecule that is at least in part found in the LTR may be located at a 5' portion or at a 3' portion of the RNA molecule. In a preferred embodiment, the LTR comprises at least a binding site for a transcription factor chosen from the group consisting of NF-kappa B, SP-1, AP-1, E-box factors, and GATA factors.

Further, the LTR sequence may comprise a sequence from a THE1 family of LTRs, in particular from THE1A, THE1B, THE1C, and THE1D. This family and theses sub-families are known to a person of skill in the art.

Preferably, the RNA molecule is an RNA molecule with a sequence of SEQ ID NO 1 to 2.

In another aspect, the invention refers to a DNA molecule (RNA fusion molecule) with a sequence corresponding to an RNA molecule of claims 1 to 5. Corresponding means that the DNA comprises of consists of a sequence from which the RNA molecule described above and herein can be transcribed.

In another aspect, the invention refers to the use of a molecule as described above and herein in medicine, in particular for diagnosing, monitoring, and/or prognosing cancer in a subject.

In yet another aspect, the invention refers to a method for diagnosing, monitoring, and/or prognosing cancer based on a biological sample, wherein the cancer involves the expression or overexpression of a RNA molecule of claims 1 to 5 in a subject, comprising
    detecting the presence or absence of the RNA molecule in the biological sample, and
    deducing from the presence of the RNA molecule that the subject suffers from cancer. Since LTR usually comprises strong promoters, such transcripts can usually be found in high numbers due to strong expression (overexpression).

Preferably, the detection of the molecule is through performing an amplification reaction and/or using a microarray. The amplification reaction can be selected from the group consisting of polymerase chain reaction (including a real time polymerase chain reaction) and ligase chain reaction.

The cancer is preferably selected from the group consisting of malignant hematological diseases, in particular malignant hematological diseases, such as Hodgkin lymphoma and anaplastic large cell lymphoma (ALCL).

In yet another aspect, the invention refers to a vector comprising a molecule with a sequence as described herein, in particular comprising a sequence of SEQ ID NO 3 or SEQ ID NO 4. Preferably, in the vector the sequence (e.g. of SEQ ID NO 3 and/or SEQ ID NO 4) is operatively linked to an expression control sequence allowing expression in a prokaryotic or a eukaryotic host cell.

In another aspect, the invention refers to a prokaryotic host cell genetically engineered with a sequence as described herein, in particular with a sequence of SEQ ID NO 3 or SEQ ID NO 4 or with the vector as described above.

In a further aspect, the invention refers to a kit for detecting a disease that involves an expression or overexpression of a fusion molecule as described herein, in particular CSF1R, comprising a primer for amplifying a nucleic acid fragment comprising a sequence encoding an endogenous gene, such as CSF1R, at a 3' portion, and a sequence that is at least in part found in the LTR.

The invention also refers to a method for decreasing the number of fusion molecules as described in a cell, comprising introducing into the cell or generating in the cell a means for decreasing the number of fusion molecules in the cell.

In a further aspect, the invention refers to a method for treating a patient suffering from cancer that involves expression or overexpression of fusion molecules as described herein in a cell, comprising administering to the patient an effective amount of a means for decreasing the number of molecules in the cell.

In another aspect the invention refers to a pharmaceutical composition, comprising a means for decreasing the number of fusion molecules, e.g. with a sequence of SEQ ID NO. 1 to 4 in a cell.

Such means for decreasing can be an siRNA or an antisense RNA. Such molecules and ways to devise them are known to a person of skill in the art.

In another aspect of the invention, DNA demethylation of the genomic DNA encoding the repressor CBFA2T3 can be used to detect cancer in a subject. Accordingly, further aspects of the invention refer to the methylated and unmethylated genomic sequences, to methods of detecting the methylated and unmethylated sites (using bisulfite treatment as known in the art), optionally amplification of the treated nucleic acids and detection of the methylation (detection of the unmethylation), as well as kits related thereto.

In a more specific aspect, the invention refers to a polynucleotide in the form of an RNA molecule (a spliced mRNA transcript initiating at the newly identified LTR promoter) with
    a sequence of SEQ ID NO. 1, or
    a sequence of SEQ ID NO. 2 (which is the reverse complementary sequence to the sequence of SEQ ID NO. 1), or
    a sequence that is at least 70%, at least 80%, at least 90%, at least 95%, or most preferably at least 99% identical to one of the beforementioned sequences, or
    any fragment of a beforementioned sequence, that comprises a portion encoding for CSF1R and a portion of the 5' untranslated region that is not found in the wild type transcript. Such a RNA molecule can be used in medicine as further described herein.

In addition to a sequence of SEQ ID NO. 1, the invention refers also to a sequence with a 5' untranslated region as described herein (transcript initiating at the newly identified LTR promoter) that comprises the full coding sequence for the CSF1G protein as known.

An RNA molecule with a sequence of SEQ ID NO. 2 or a sequence with an identity thereto as described above, or a fragment thereof can e.g. be used as a probe in detecting a molecule of SEQ ID NO. 1.

The invention also refers to a DNA molecule (fusion cDNA) with
    a sequence of SEQ ID NO. 3, or
    a sequence of SEQ ID NO. 4, (which is the reverse complementary sequence to the sequence of SEQ ID NO. 3), or
    a sequence that is at least 70%, at least 80%, at least 90%, at least 95%, or most preferably at least 99% identical to one of the beforementioned sequences, or
    any fragment of a beforementioned sequence, that comprises a portion encoding for CSF1R and a portion of the 5' untranslated region that is not found in the wild type transcript. Such a RNA molecule can be used in medicine as further described herein.

The invention also refers to the use of a spliced RNA or a DNA molecule initiating at the newly identified LTR promoter as described above for detecting a disease that is accompanied with or involves an overexpression of CSF1R (i.e. of the RNA and/or the protein) in a subject, in particular based on a biological sample.

The invention also refers to a method for detecting a disease that involves an overexpression of CSF1R (i.e. of the RNA and/or the protein) in a subject from a biological sample, comprising
    detecting the presence or absence of an RNA fusion transcript as described above in the biological sample, and
    deducing from the presence of a spliced RNA molecule initiating at the newly identified LTR promoter that the subject suffers from the disease. Usually, the detection of the spliced RNA molecule initiating at the newly identified LTR promoter occurs via the detection of a cDNA molecule, which is derived from the spliced RNA molecule initiating at the newly identified LTR promoter through reverse transcription, as known in the art. This method can also be used for monitoring the progression of the disease, e.g. under treatment, or for prognosis of the disease.

The detection of the spliced RNA transcript initiating at the newly identified LTR promoter is preferably through performing an amplification reaction. This amplification reaction can be a polymerase chain reaction (PCR) or a ligase chain reaction. The polymerase chain reaction is preferably a real time polymerase chain reaction.

Alternatively, the detection of the spliced RNA transcript can be performed using in situ hybridization.

The disease detected in the method is a disease that is selected from the group consisting of breast (mamma) carcinoma and malignant hematological diseases, such as lymphoma. The malignant hematological disease, in turn, is selected from the group consisting of Hodgkin lymphoma and anaplastic large cell lymphoma.

The word "detecting" or detection is meant to refer to diagnosing, monitoring (e.g. under treatment), and/or prognosing.

The invention also refers to the use of a method as described above and herein for detecting a disease that is caused by or involves an overexpression of CSF1R.

The invention also refers to a vector comprising a sequence of SEQ ID NO 3 and/or SEQ ID NO 4. In such a vector, the sequence of SEQ ID NO 3 and/or SEQ ID NO 4 preferably is operatively linked to an expression control sequence allowing expression in a prokaryotic or a eukaryotic host cell.

The invention also refers to a prokaryotic host cell genetically engineered with a sequence of SEQ ID NO 3 or SEQ ID NO 4 or with the vector described above and herein.

The invention also refers to a kit for detecting a disease that involves an overexpression of CSF1R, comprising
a primer for amplifying a nucleic acid fragment comprising a portion encoding for CSF1R and a portion of the 5' untranslated region that is not found in the wild type transcript. Preferred primers are listed in Table 3.1. Most preferably, the primer is selected from the group consisting of −6152, −5090, −161 and +131 of Table 3.1.

The invention further refers to a method for decreasing the amount of CSF1R in a cell, comprising
introducing into the cell or generating in the cell a means for decreasing the number of molecules with a sequence of SEQ ID NO. 1 in the cell.

The invention further refers to a method for treating a patient suffering from a disease that involves an overexpression of CSF1R comprising administering to the patient an effective amount of a means for decreasing the number of molecules with a sequence of SEQ ID NO. 1 in the cell.

The invention still further refers to a pharmaceutical composition, comprising a means for decreasing the number of molecules with a sequence of SEQ ID NO. 1 in a cell.

The means for decreasing the number of molecules with a sequence of SEQ ID NO. 1 in a cell is preferably an siRNA molecule. Such a siRNA molecule needs to be revers complementary to a sequence of SEQ ID NO 1 and preferably has a length of 16 to 28, preferably of 18 to 25, most preferably of 21 or 22 nucleotides. Therefore, such an siRNA molecule represents a portion of the sequence of SEQ ID NO 2.

Sequences of the polynucleotides of the invention are also shown in FIG. 11.

```
Hodgkin-specific transcript (non-canonical CSF1R transcript),
(5'-3'),
                                                       SEQ ID NO. 3
CTCTTTTGCCTGCCATCATGTTGGATGTGATTCTGCTCCTCCTTTGCCTTCCACTATGAT

TCTGAGGCCTCCTCAGCCATGCTGAACTGTTTACCTGTTCTGGATGTTTCATATAGATGG

AGTCGTATGACATTTTGCTACTGGCTTCATTGACTTAACACAGTGTTTTCAAGGTTCATC

CACAGTGTAGCAGCTAAAAGGGGAAGAAGAGGATCAGCCCAAGGAGGAGGAAGAGGAAAA

CAAGACAAACAGCCAGTGCAGAGGAGAGGAACGTGTGTCCAGTGTCCCGATCCCTGCGGA

GCTAGTAGCTGAGAGCTCTGTGCCCTGGGCACCTTGCAGCCCTGCACCTGCCTGCCACTT

CCCCACCGAGGCCATGGGCCCAGGAGTTCTGCTGCTCCTGCTGGTGGCCACAGCTTGGCA

TG

Hodgkin-specific transcript (non-canonical CSF1R transcript),
complement,
                                                       SEQ ID NO. 9
GAGAAAACGGACGGTAGTACAACCTACACTAAGACGAGGAGGAAACGGAAGGTGATACTA

AGACTCCGGAGGAGTCGGTACGACTTGACAAATGGACAAGACCTACAAAGTATATCTACC

TCAGCATACTGTAAAACGATGACCGAAGTAACTGAATTGTGTCACAAAAGTTCCAAGTAG

GTGTCACATCGTCGATTTTCCCCTTCTTCTCCTAGTCGGGTTCCTCCTCCTTCTCCTTTT

GTTCTGTTTGTCGGTCACGTCTCCTCTCCTTGCACACAGGTCACAGGGCTAGGGACGCCT

CGATCATCGACTCTCGAGACACGGGACCCGTGGAACGTCGGGACGTGGACGGACGGTGAA

GGGGTGGCTCCGGTACCCGGGTCCTCAAGACGACGAGGACGACCACCGGTGTCGAACCGT

AC

Hodgkin-specific transcript (non-canonical CSF1R transcript),
inverse,
                                                       SEQ ID NO. 10
GTACGGTTCGACACCGGTGGTCGTCCTCGTCGTCTTGAGGACCCGGGTACCGGAGCCACC

CCTTCACCGTCCGTCCACGTCCCGACGTTCCACGGGTCCCGTGTCTCGAGAGTCGATGAT
```

-continued

```
CGAGGCGTCCCTAGCCCTGTGACCTGTGTGCAAGGAGAGGAGACGTGACCGACAAACAGA

ACAAAAGGAGAAGGAGGAGGAACCCGACTAGGAGAAGAAGGGGAAAATCGACGATGTGAC

ACCTACTTGGAACTTTTGTGACACAATTCAGTTACTTCGGTCATCGTTTTACAGTATGCT

GAGGTAGATATACTTTGTAGGTCTTGTCCATTTGTCAAGTCGTACCGACTCCTCCGGAGT

CTTAGTATCACCTTCCGTTTCCTCCTCGTCTTAGTGTAGGTTGTACTACCGTCCGTTTTC

TC

Hodgkin-specific transcript (non-canonical CSF1R transcript),
inverse complement,
                                                    SEQ ID NO. 4
CATGCCAAGCTGTGGCCACCAGCAGGAGCAGCAGAACTCCTGGGCCCATGGCCTCGGTGG

GGAAGTGGCAGGCAGGTGCAGGGCTGCAAGGTGCCCAGGGCACAGAGCTCTCAGCTACTA

GCTCCGCAGGGATCGGGACACTGGACACACGTTCCTCTCCTCTGCACTGGCTGTTTGTCT

TGTTTTCCTCTTCCTCCTCCTTGGGCTGATCCTCTTCTTCCCCTTTTAGCTGCTACACTG

TGGATGAACCTTGAAAACACTGTGTTAAGTCAATGAAGCCAGTAGCAAAATGTCATACGA

CTCCATCTATATGAAACATCCAGAACAGGTAAACAGTTCAGCATGGCTGAGGAGGCCTCA

GAATCATAGTGGAAGGCAAAGGAGGAGCAGAATCACATCCAACATGATGGCAGGCAAAAG

AG
```

The RNA sequences of SEQ ID NO. 1 and 2 can be deduced from the DNA sequences of SEQ ID NO. 3 and 4 shown above, respectively, but are RNA instead of DNA sequences. Therefore, all Ts of SEQ ID NO. 3 and 4 shown above need to be substituted by Us to obtain the RNA sequences of SEQ ID NOs. 1 and 2.

Further polynucleotides of the invention comprise the 5' UTR initiating at the newly identified LTR promoter together with the coding region for CSF1R. Still further polynucleotides of the invention are polynucleotides with an identity of at least 70%, at least 80%, at least 90%, at least 95%, or most preferably at least 99% to a beforementioned sequence, and any fragment of a beforementioned sequence, that comprises a portion encoding for CSF1R and a portion of the 5' untranslated region that is not found in the wild type transcript. Such a RNA molecule can be used in medicine as further described herein.

SEQ ID NOs 5 to 8 are depicted in FIG. 24a.

FIGURES

FIG. 1. Lineage-inappropriate expression of functional CSF1R and CSF-1 in Hodgkin lymphoma cells. Analysis of CSF1R and CSF-1 protein expression and of CSF1R:Fc functionality. (A) Analysis of CSF1R and CSF1 mRNA expression by RT-PCR in Hodgkin and non-Hodgkin cell lines. Expression of GAPDH was analyzed as a control. (1a) Analysis of CSF1R and CSF1 mRNA expression by RT-PCR in Hodgkin's and non-Hodgkin's cell lines. GAPDH expression was analyzed as a control. One representative of four independent experiments is shown. (B, C) Analysis of CSF1R (B) and CSF-1 (C) protein expression in various cell lines by extracellular and intracellular flow cytometry, respectively. IC, isotype control. (D) Supernatants of various cell lines were analyzed by a CSF-1-specific ELISA. The amount of CSF-1 is shown in ng per ml. As controls, standard medium and the reagent diluent for the standard (reagent D) were included. Date are represented as mean±SD. (E) Induction of CSF1R phosphorylation in HRS cells. Lysates of untreated L540Cy cells and cells stimulated with rhCSF-1 for the indicated times were immunoprecipitated (IP) with a CSF1R-specific antibody or the respective IC. CSF1R tyrosine phosphorylation was detected by WB with an antibody recognizing phospho-tyrosine (p-Tyr; upper panel). As a control, the membrane was reprobed with a CSF1R-specific antibody (lower panel). (F) Constitutive CSF1R tyrosine phosphorylation in HRS cell lines. CSF1R IP of untreated or rhCSF-1 stimulated L540Cy cells, and of unstimulated L428, L1236, KM-H2, L591, HDLM-2 and L540 cells was performed as described in (E). (1F) Analysis of rhCSF-1-induced CSF1R tyrosine phosphorylation in L540Cy cells and of basal levels of CSF1R tyrosine phosphorylation in HRS cell lines following CSF1R immunoprecipitation (IP). IC, isotype control. CSF1R tyrosine phosphorylation was detected by western blotting with an antibody recognizing phosphotyrosine (p-Tyr; top). As a control, the membrane was reprobed with a CSF1R-specific antibody (bottom). One representative of three independent experiments is shown. (G) CSF1R in situ hybridization (ISH) of a representative cHL patient sample with a CSF1R antisense probe (left) or, as a control, sense probe (right). Arrows indicate HRS cells. (1G) CSF1R ISH of a Hodgkin's lymphoma-affected lymph node, using a CSF1R antisense probe (left) or, as a control, a sense probe (right). One representative of ten samples is shown. Arrows indicate HRS cells.

FIG. 2. Expression of CSF-1 is dependent on NF-κB. L428 cells were transfected with the NF-κB super-repressor IκBαΔN or the respective mock control along with pEGFP. Expression of CSF-1 was analyzed in GFP-positive cells by intracellular flow cytometry (upper panel). Expression of IκBαΔN in L428 cells was verified by WB (lower panel). Note that L428 cells lack endogenous IκBα wt expression. β-actin was analyzed as control.

FIG. 3. HRS cells depend on CSF1R activity. (A) L540Cy cells were left untreated (−) or treated with the indicated amounts rhCSF-1 (closed bars) or the respective control (open bars) under serum reduced conditions (1% FCS). After 48 hours, cells were pulsed with 1 μCi [$^3$H]-thymidine per well for a further 20 hours, and [$^3$H]-thymidine incorporation was determined. cpm, counts per minute. Data are represented as mean±SD. (3A) [$^3$H]-thymidine incorporation in L540Cy cells left untreated (−) or treated with the indicated amounts of rhCSF-1 (black bars) or water control (open bars) under serum-reduced conditions (1% FCS) determined after 48 h. Data are represented as means±s.d. One of three experiments is shown. NS, not significant. *P<0.001. (B) Growth arrest of KM-H2 cells following CSF-1 inhibition. KM-H2 cells were treated with 80 μg/ml of the IgG1:Fc control or the specific CSF1R:Fc construct, as indicated. Cells left untreated or treated with BSA were included as controls. After 24 hours, cells were pulsed with [$^3$H]-thymidine incorporation and analyzed as described in (A). (3B) Growth arrest of KM-H2 cells after CSF-1 inhibition. KM-H2 cells were treated with the IgG1:Fc control or with CSF1R:Fc, as indicated. Cells treated with BSA were included as a control. After 24 h, cells were pulsed with [$^3$H]-thymidine. Data are represented as means s.d. One of three experiments is shown. n.s., not significant. *P<0.001. (C) Pharmacological inhibition of CSF1R activation. L540Cy cells were left untreated (−) or stimulated with rhCSF-1 (+) without or after preincubation with the CSF1R inhibiting compounds CYC10268, CYC12752 and CYC12200 or the respective DMSO control. 10 min after addition of rhCSF-1 cells were lyzed and IPs were performed as described in FIG. 1E. (3C) Effects of pharmacological inhibition of CSF1R activation on CSF1R tyrosine phosphorylation. L540Cy cells were left untreated (−) or stimulated with rhCSF-1 (+) without or after preincubation with the CSF1R-inhibiting compounds CYC10268, CYC12752 or CYC12200 or a DMSO control. CSF1R tyrosine phosphorylation was analyzed as described in FIG. 1F. One representative of three independent experiments is shown. (D) Pharmacological inhibition of CSF activity induces apoptosis in HRS but not in non-HRS cell lines. HRS (KM-H2, HDLM-2, L540) and non-HRS (Reh, Namalwa) cell lines were treated for the indicated times with 2 μM CYC10268. The percentage of viable, annexin V-FITC/PI negative cells is shown. One out of three experiments is shown. (3D) Effects of pharmacological inhibition of CSF1R activity on apoptosis. HRS (KM-H2, HDLM-2 and L540) and non-Hodgkin's (Reh and Namalwa) cell lines were treated for the indicated times with 2 μM CYC10268. The percentage of viable, annexin V-FITC/PI-negative cells is shown. One of three experiments is shown.

FIG. 4. Determination of CSF1R transcription start sites (TSS); HRS cells express CSF1R from a different promoter. (A) HRS cells express CSF1R from a different promoter than do non-Hodgkin's cells. To scan for 5'-ends of CSF1R transcripts by qRT-PCR, primers that anneal in exon 1 (−100/−32) or 2 (+59/+131) or in the upstream region (−169/−97; −595/−504; −805/−731) of the CSF1R gene were used. Primer pair+1/+76 (exon1/intron) served as negative control. The map of the CSF1R gene shows the positions of the primers relative to the translation start site (marked as +1). Dashed line, 5' upstream region; grey line, 5'-UTR; black bars, exons, translated regions; dashed line with double slash, intron. n.d., not detectable. (4A) To scan for 5' ends of CSF1R transcripts, mRNA of HRS (L428, L591, L540Cy, KM-H2), myeloid (HL-60) and non-Hodgkin (Namalwa) cell lines was amplified by quantitative RT-PCR using primers that anneal in exon 1 (−100 to −14) or 2 (+59 to +148; positions refer to the mature mRNA transcript) or in the upstream region (−169 to −78; −595 to −483; −805 to −713) of the CSF1R gene. mRNA expression is shown relative to TBP. A primer pair spanning +1 to +96 (exon 1-intron) served as a negative control. Data are represented as means±s.d. One representative of two independent experiments is shown. Top, a schematic of the CSF1R gene shows the positions of the primers relative to the translation start site (marked as +1). Dotted line, 5' upstream region; gray line, 5' UTR; black bars, exons; dashed line with double slash, intron. n.d., not detectable. (B) HRS cells express CSF1R from a different promoter than do non-Hodgkin's cells. Gel analysis of RLM-5'-RACE products. Total RNA from the indicated cell lines was subjected to RLM-5'-RACE and specifically amplified by nested PCR using CSF1R-specific primers. Primer positions are marked (bottom panel). Grey arrow, major amplification product in HL-60 cells; black arrow, major product in KM-H2 and L540Cy HRS cells. DNA marker, 100 bp DNA ladder; NC, negative control. (4B) Gel analysis of 5' RACE products after amplification by nested PCR with CSF1R-specific primers. Gray arrow, major amplification product in HL-60 cells; black arrow, major product in KM-H2 and L540Cy HRS cells. One representative of three independent experiments is shown. DNA marker, 100-bp DNA ladder; NC, negative control. Top, a schematic of the 5' RACE strategy. Arrows represent primer positions. For further description refer to legend of (A). (C) The HRS cell-specific, non-canonical CSF1R transcripts are spliced; schematic summary of the 5'-ends of the CSF1R transcripts. The grey lines represent the 5'-UTR of CSF1R transcripts in HRS and HL-60 cells, respectively. Dashed lines indicate regions that are spliced in HRS cells. Black bar represents the first part of the coding sequence within the first exon (translation start site +1).

FIG. 5. The non-canonical CSF1R transcripts are specific for HL cells. (A) HRS cells express CSF1R from a different promoter than do non-Hodgkin's cells. Map of the CSF1R gene with positions of the primers relative to the translation initiation site related to the gene (−6152; −5090; −161) or the cDNA (+131; +720, +1304; italic). For further description refer to legend of FIG. 4A. (5a) Schematic summary of the 5' ends of the CSF1R transcripts. Gray lines represent the 5' UTRs of CSF1R transcripts. The top and bottom transcripts correspond to those identified in HRS (noncanonical transcript) and HL-60 cells (canonical transcript), respectively. In HRS cells, regions of 975 bp and 4,849 bp are spliced out of the primary transcript. Positions of all primers used in FIGS. 5-16 for amplification of CSF1R mRNA transcripts are indicated relative to the CSF1R translation initiation site (primer positions −6,152, −5,090, and −143 refer to positions in the CSF1R genomic sequence; primer positions +148, +720, and +1,325 refer to positions in the mature CSF1R mRNA transcript). (B) Expression of the canonical (+720/+1304) and non-canonical (−5090/+131; −6152/−161) CSF1R transcripts was analyzed by RT-PCR in various cell lines, as indicated, and purified primary CD33-positive cells from five healthy donors (CD33__#1 to CD33__#5). Expression of GAPDH was analyzed as a control. (5B) RT-PCR analysis of the expression of the canonical (+720 to +1,325) and noncanonical (−5,090 to +148; −6,152 to −143) CSF1R transcripts in various cell lines and primary CD33-positive cells from five healthy donors (CD33__1 to CD33__5). GAPDH expression was analyzed as a control. One of three experiments is shown. (C) Total RNA was extracted from frozen sections of three lymph nodes affected by HL (HL__#1 to HL__#3) and, as controls, of nine human tonsils (human tonsils #1 to #9). Expression of the canonical and non-canonical CSF1R transcripts was analyzed by RT-PCR, as indicated. The analyses of CSF1R transcripts in KM-H2 and Reh cells as well as of GAPDH were included as controls. (5C) RT-PCR analysis of the canonical and noncanonical CSF1R transcripts following extraction of total RNA from frozen sections of three lymph nodes affected by Hodgkin's lymphoma (HL__1 to HL__3)

and, as controls, of nine human tonsils (human tonsils 1 to 9). KM-H2 and Reh cells were included as controls. GAPDH expression was analyzed as a control. One of three experiments is shown.

FIG. 6. The non-canonical CSF1R transcripts in HRS cells initiate at an aberrantly activated LTR. (A) DNase I hypersensitive site (DHS) mapping of the Hodgkin-specific CSF1R TSS. Top panel: Map of the upstream region of the CSF1R gene. The arrow marks the Hodgkin-specific TSS at position −6197 bp relative to the translational initiation site. Specific restriction sites and their positions are indicated. Bottom panel, DHS mapping showing hypersensitive sites at the Hodgkin-specific TSS. Cells were treated without (−) or with increasing concentrations of DNase I, as indicated. Genomic DNA was digested with KpnI and analyzed by Southern blotting using the indicated hybridization probe. The arrows on the right side indicate DHSs. The digestion with KpnI resulted in an approximately 3.3 kb fragment between −5030 bp and −8307 bp. To generate a DNA size marker the KpnI digested genomic DNA was further digested with DraI (−5577 bp), ScaI (−5988 bp) and AseI (−7004 bp) as shown on the left and the top panel. (6A) DNase I-hypersensitive site (DHS) mapping in the vicinity of the Hodgkin's lymphoma-specific CSF1R TSS. Top, map of the upstream region of the CSF1R gene. The Hodgkin-specific TSS at position −6,197 bp is marked by an horizontal arrow. Specific restriction sites and their positions are indicated. The positions of DHSs (see bottom panel) are indicated by heavy arrows and the position of the hybridization probe is indicated. Bottom, Southern analysis of DNase I treated genomic DNA of various cell lines, as indicated. Permeabilized cells were treated without (−) or with increasing concentrations of DNase I, as indicated. Genomic DNA was digested with KpnI and analyzed by Southern blotting and indirect end-labelling with a hybridization probe abutting the restriction fragment (see scheme, top panel). The arrows on the right indicate DHSs. One of two experiments is shown. (B) HRS cells express CSF1R from a different promoter than do non-Hodgkin's cells. The upstream element is an LTR. (6B) Genomic sequence (SEQ ID NO 94) of the genomic CSF1R LTR and flanking sequences. The LTR region is marked with gray rectangles. The 5' UTR of the HRS cell lines from the transcription start site (marked as '+1') to the first splice site is underlined. Numbers and arrows refer to the luciferase constructs used in FIGS. 5 and 6. 'E-Box', 'GATA', 'Sp1', 'AP-1' and 'NF-kB' indicate transcription factor binding sites, 'TATA' indicates a TATA box. (C) The LTR has promoter activity in transient assays. pGL2 basic (negative control), pGL2 control (positive control, containing the SV40 promoter) or pGL2-LTR promoter constructs of different length (−85/+14, −142/+14, −382/+14; see also FIG. 6B) were transiently transfected in L428 and L540Cy cells. Luciferase activity is shown as fold activation compared to pGL2 basic activity, which was set 1. Date are represented as mean SD. (6C) Analysis of luciferase activity of various CSF1R LTR promoter constructs. The LTR has promoter activity. pGL2 basic (negative control), pGL2 control (positive control; contains an SV40 promoter and an SV40 enhancer) or pGL2 LTR promoter constructs (−85 to +14; −142 to +14; −382 to +14; see also FIG. 6B) were transfected into L428 and L540Cy cells. Luciferase activity is shown as fold activation compared to pGL2 basic activity (set as 1). Data are represented as mean±s.d. One of three experiments is shown. *P<0.001 for comparison to pGL2 basic. n.s., not significant. (D) Mutational analysis of the LTR −142/+14 promoter construct. L428 cells were transfected with LTR −142/+14 promoter constructs with and without mutated transcription factor binding sites (mutations are indicated by black crosses), as indicated. Luciferase activity is shown as fold activation compared to pGL2 basic activity, which was set 1. Date are represented as mean±SD. (6D) Mutational analysis of the LTR −142 to +14 promoter construct. L428 cells were transfected with unchanged or mutated LTR −142 to +14 promoter constructs (mutations of transcription factor binding sites are indicated in the schematic by black crosses), as indicated. Grey rectangles represent binding sites for transcription factors Sp1, GATA, AP-1 and NF-kB. Luciferase activity is shown as described in C. One of three experiments is shown. *P<0.001 for comparison to wild type (WT).

FIG. 7. Analysis of CSF1R LTR DNA methylation and CBFA2T3 expression. Expression of the transcriptional corepressor CBFA2T3 is lost in HRS cells. (A) Activation of the non-canonical CSF1R transcripts following treatment with TSA and/or 5-aza-dC. The non-HRS cell lines Reh and Namalwa were left untreated or treated with 5-aza-dC, TSA, or 5-aza-dC in combination with TSA. The expression of canonical and non-canonical CSF1R transcripts was analyzed by RT-PCR. The analysis of KM-H2 cells and of GAPDH expression were used as controls. (7A) Analysis of canonical and noncanonical CSF1R transcripts following treatment of Reh and Namalwa cells with TSA and/or 5-aza-dC. The non-Hodgkin's cell lines Reh and Namalwa were left untreated or were treated with 5-aza-dC, TSA or 5-aza-dC and TSA together. The expression of both canonical (+720 to +1,325) and noncanonical (−5,090 to +148 and −6152 to −143) CSF1R transcripts was analyzed by RT-PCR. KM-H2 cells were used as a control. GAPDH expression was analyzed as a control. As negative control, water was used instead of cDNA (NC). One of three experiments is shown. (B) Various cell lines and primary CD19+ human tonsilar B cells were analyzed for expression of CBFA2T3 mRNA by RT-PCR (upper panel) and protein by Western blotting (WB; lower panel) expression. Note, that in the non-HRS cell lines and in CD19+ B cells expression of the two variants CBFA2T3a and CBFA2T3b was detectable. Expression of GAPDH and β-actin were analyzed as controls. (7B) Analysis of expression of CBFA2T3 mRNA by RT-PCR (top) and protein by western blotting (WB; bottom) in various cell lines and CD19-positive human tonsilar B cells. The non-Hodgkin's cell lines and CD19-positive B cells express the two variants CBFA2T3a and CBFA2T3b. GAPDH and beta-actin expression were analyzed as controls. n.s., non-specific. One of four experiments is shown. (C) Representative immunohistochemistry (IHC) of CBFA2T3 in a germinal center of a normal human tonsil (tonsil), two classical HL cases (cHL; HRS cells are marked by arrows), and one case of diffuse large B cell lymphoma (DLBCL), chronic lymphatic leukemia (CLL) and mantle cell lymphoma (MCL), respectively. (D) Methylation of CBFA2T3 in HRS cell lines. Schematic overview of the regions analyzed for DNA methylation (upper panel) and results of bisulfite pyrosequencing in lymphoma/leukemia cell lines and controls (lower panel). For each sample the amount of DNA methylation is given as color code (red: fully methylated, 100%; green: fully unmethylated, 0%) for each individual CpG in each amplicon. Amplicons 1-3 refer to the region of the transcriptional start site of CBFA2T3b, amplicons 4 and 5 to the region of the transcriptional start site of CBFA2T3a. The results of the controls are shown as the mean of at least 5 independent investigations. (7D) Methylation of the CBFA2T3A and CBFA2T3B promoters in HRS cell lines. Overview of the regions analyzed (amplicons) for DNA methylation (top) and results of bisulfite pyrosequencing in lymphoma or leukemia cell lines and controls (bottom). Top, the GC percent is shown in 5-base windows. The exon-intron structure of CBFA2T3A and CBFA2T3B is shown underneath. Bottom, the amount of DNA methylation for each individual CpG element in each amplicon is represented by a color code (red, CpG site fully methylated (100%); green, CpG site fully unmethylated (0%)). Amplicons 1 to 3 correspond to the region of the TSS of CBFA2T3B, and amplicons 4 and 5 to the region of the TSS of CBFA2T3A. As a control, completely methylated DNA was included (Methyl. control). The mRNA expression level of the HRS cell lines analyzed is indicated on the far right. The results are shown as the mean of at least five independent experiments.

Figure 7B:
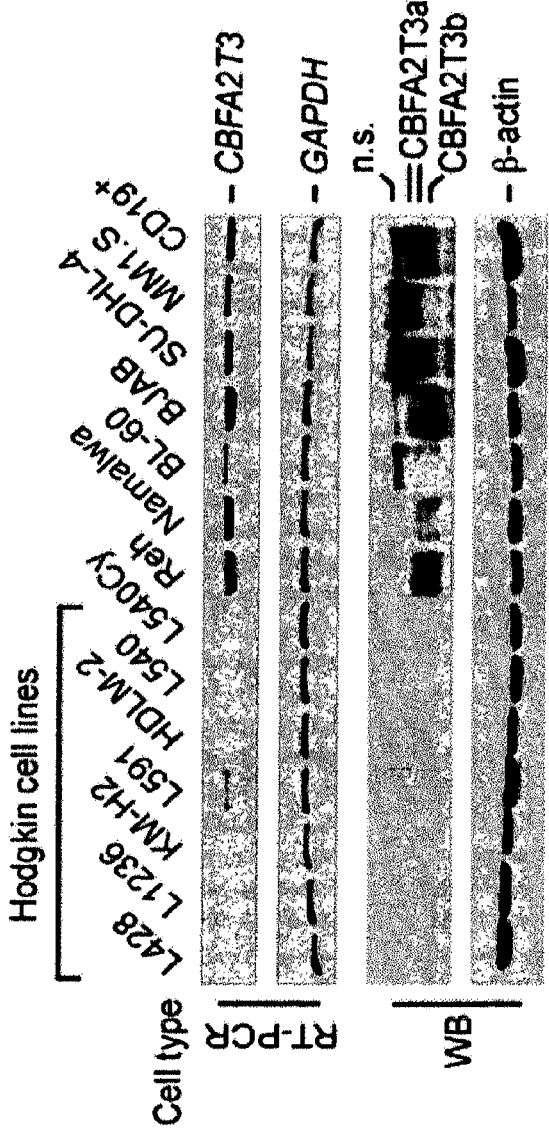
Figure 8:
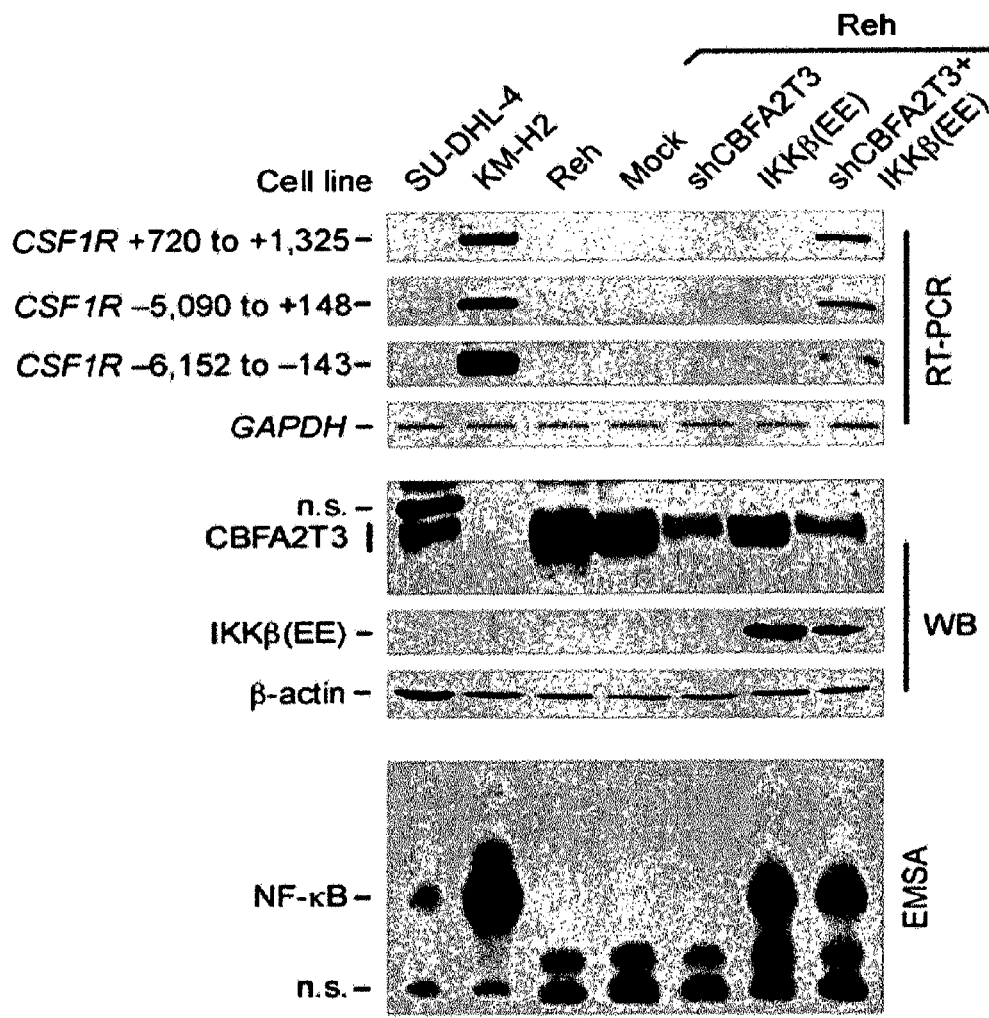

FIG. 8. Down-regulation of CBFA2T3 mediates CSF1R-LTR de-repression in non-HRS cells. The non-HRS cell line Reh was left untreated or transiently transfected with either control plasmids (Mock), or an shCBFA2T3 expression construct (shCBFA2T3), a plasmid encoding a constitutively active mutant of IKKβ (IKKβ(EE)), or the shCBFA2T3 expression construct together with IKKβ(EE) (shCBFA2T3+IKKβ(EE)), all along with pEGFP. After enrichment of transfected cells, mRNA expression of the canonical and non-canonical CSF1R transcripts was analyzed by RT-PCR (upper panels). Protein expression of CBFA2T3 and IKKβ (EE) was controlled in enriched cells by use of antibodies specific for CBFA2T3 or FLAG, respectively (center). The analysis of SU-DHL-4 and KM-H2 cells and of GAPDH and β-actin expression served as controls. The IKKβ(EE)-induced NF-κB activity was monitored by EMSA (lower panel). Note, that in KM-H2 cells NF-κB is constitutively activated. (8) CBFA2T3 expression is lacking in primary HRS cells, full CSF1R LTR activation requires CBFA2T3 downregulation and active NF-kB, and THE1 activation occurs in HRS cells at many genomic locations. Analysis of canonical and noncanonical CSF1R transcripts following transfection of Reh cells with shCBFA2T3, IKKb(EE), or both together. Reh cells were left untreated or transfected with a control plasmid (Mock), the shCBFA2T3 or IKKb(EE) constructs, or both constructs. After enrichment of transfected cells, CSF1R transcripts were analyzed by RT-PCR (top). Protein expression of CBFA2T3 and IKKb(EE) was detected by use of antibodies to CBFA2T3 or Flag, respectively (middle). CBFA2T3a and CBFA2T3b isoforms are not as well separated by gel electrophoresis as in FIG. 7B and FIG. 20, and therefore their corresponding bands are marked as 'CBFA2T3'. GAPDH and beta-actin expression were analyzed as controls. IKKb(EE)-induced NF-kB activity was monitored by electrophoretic mobility shift assay (EMSA) (bottom). Specific NF-kB protein-DNA complexes are marked (NF-kB). SU-DHL-4 and KM-H2 cells were used as controls; in KM-H2 cells, NF-kB is constitutively activated. One of three experiments is shown. n.s., non-specific.

Figure 9A:
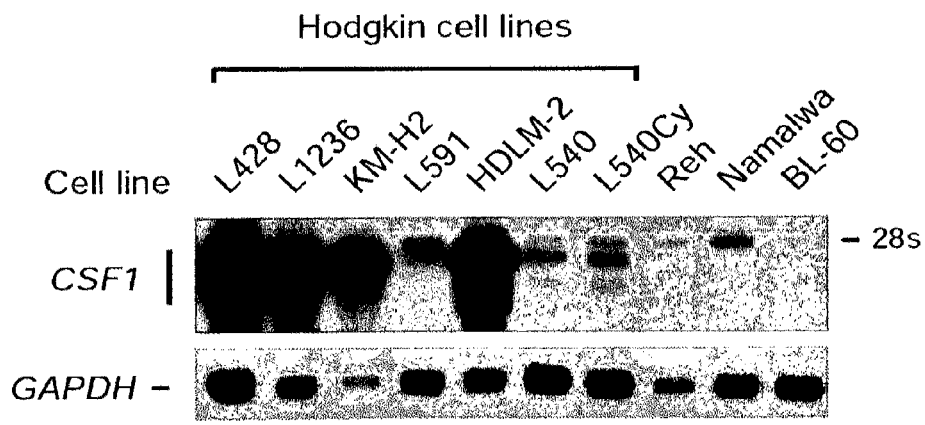
Figure 9B:
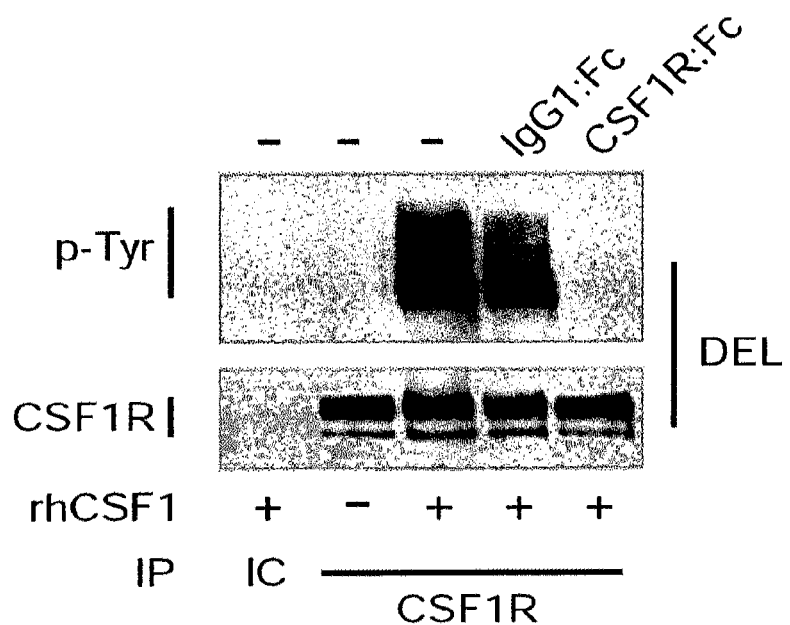
Figure 9C:
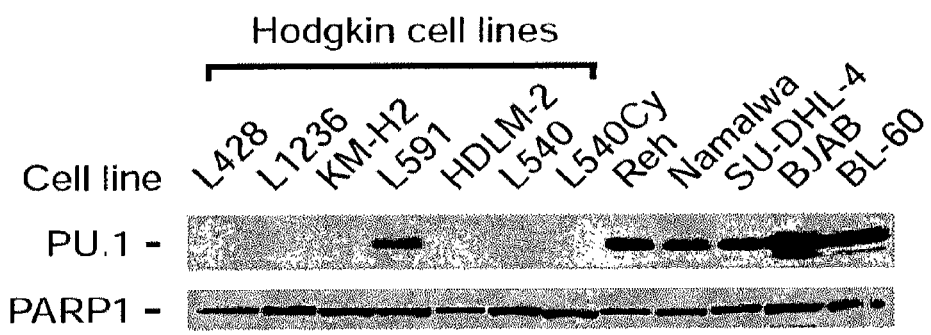

FIG. 9. (A) Analysis of CSF1 mRNA expression by Northern blot in various cell lines, as indicated. Expression of GAPDH was analyzed as a control. Note, that Hodgkin cell lines overexpress two splice variants compared to control cell lines Reh, Namalwa and BL60, which lack CSF1 expression. (B) To test the functionality of the decoy-receptor-like CSF1R:Fc inhibitor, anaplastic large cell lymphoma derived DEL cells, which show an abundant CSF1R expression (Mathas, S. et al., *PNAS* 106, 5831-5836 (2009)), were left untreated or stimulated with rhCSF1 with or without preincubation with CSF1R:Fc or the respective IgG1:Fc control. Thereafter, IP was performed with a CSF1R-specific antibody or the respective isotype control (IC), and CSF1R tyrosine phosphorylation was detected by immunoblot with antibody to phospho-tyrosine (p-Tyr; upper panel). As a control, the membrane was reprobed with antibody to CSF1R (lower panel). Note, that CSF1R:Fc prevents rhCSF-1 induced CSF1R phosphorylation.

(C) Protein expression of transcription factor PU.1 in various cell lines, as indicated. Nuclear extracts of the various cell lines were analyzed by Western blotting for expression of PU.1 and, as a control, for PARP1.

Figure 10A:
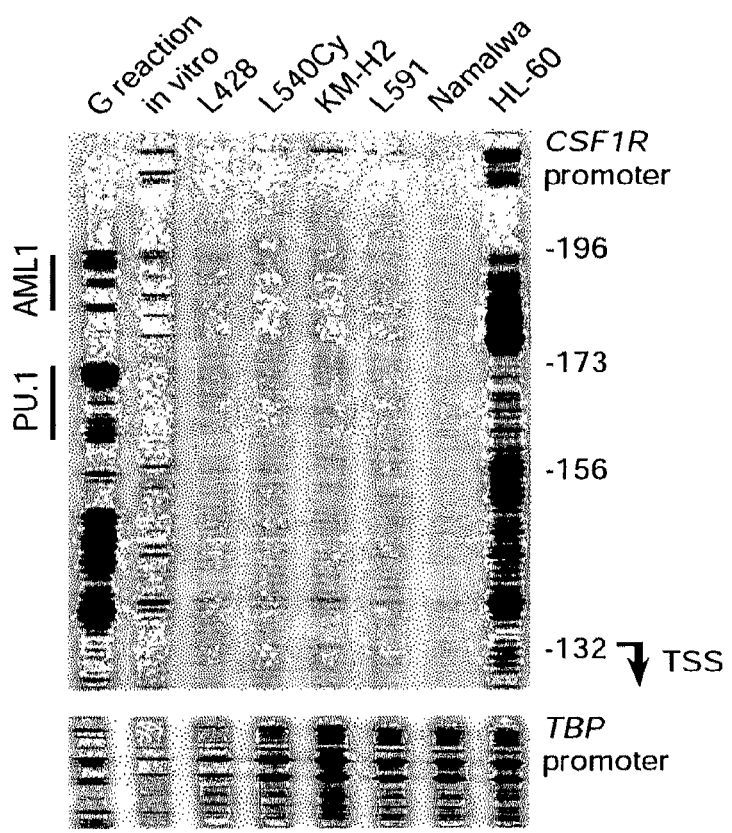
Figure 10:
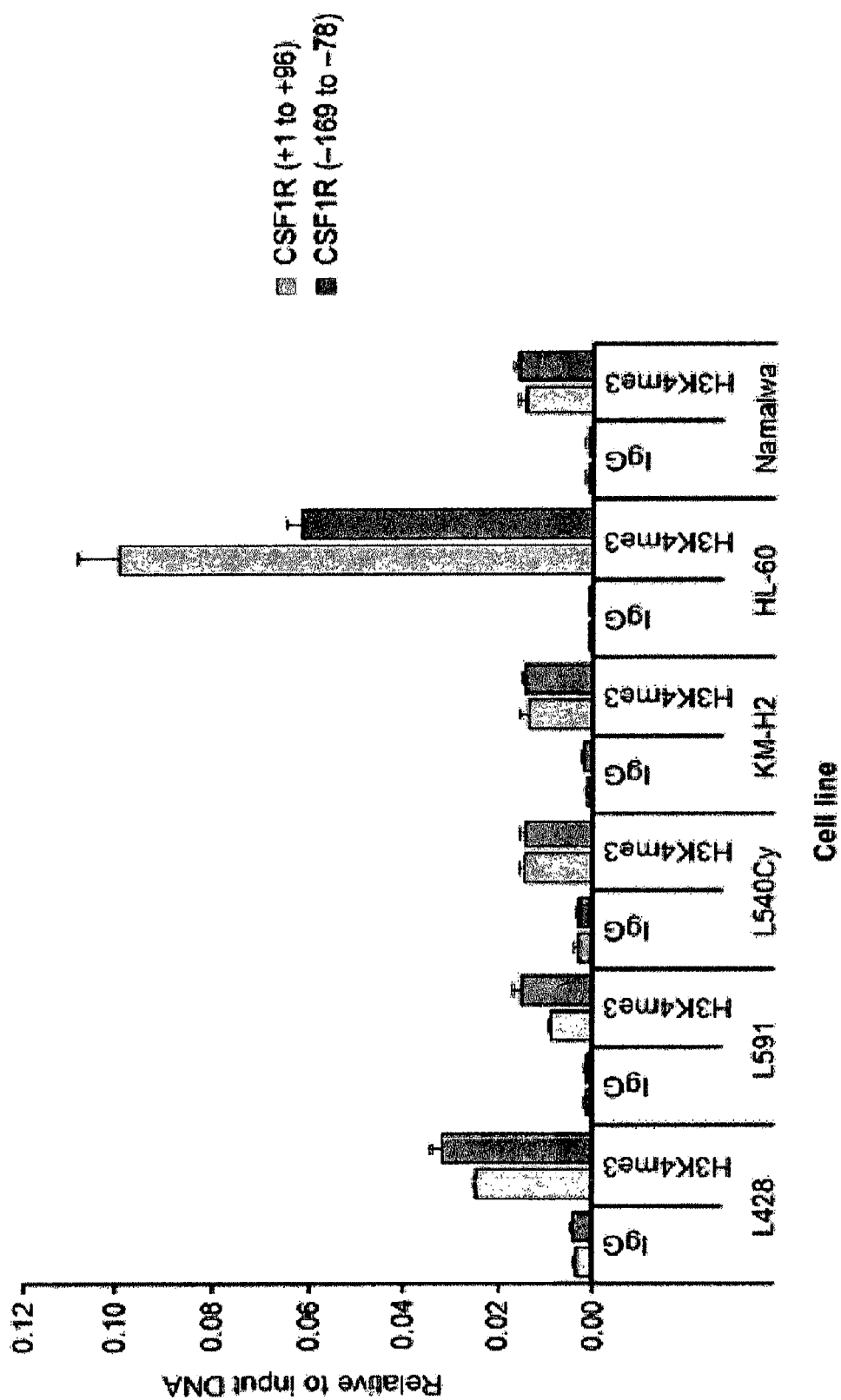

FIG. 10. The myeloid CSF1R promoter is organized in inactive chromatin in HRS cells. (A) DNase I in vivo footprinting experiment examining the myeloid-specific CSF1R promoter in the indicated cell lines. G reaction: Maxim-Gilbert sequencing reaction. In vitro: DNAse I treated naked DNA. As internal control, the same material was amplified with primers specific for the TBP promoter (lower panel). The position of known transcription factor binding sites is indicated at the left, the position of the TSS is indicated by an arrow at the right and is numbered according to the position of the ATG. (B) Chromatin immunoprecipitation experiment examining the presence of trimethylated histone lysine 3 (H3K4me3) at the myeloid promoter in different cell lines. Values were normalized to input DNA and represent the mean values of three measurements. The background is determined by the signal observed in Namalwa cells.

FIG. 11. Sequences obtained by 5'RACE analyses in Hodgkin cell lines (upper panel, SEQ ID NO 3) and HL-60 cells (lower panel, SEQ ID NO 11). Translated sequences are in bold, the translation initiation site (ATG) is underlined. In the Hodgkin-specific transcript, splice sites are shown in BOLD.

Figure 12:
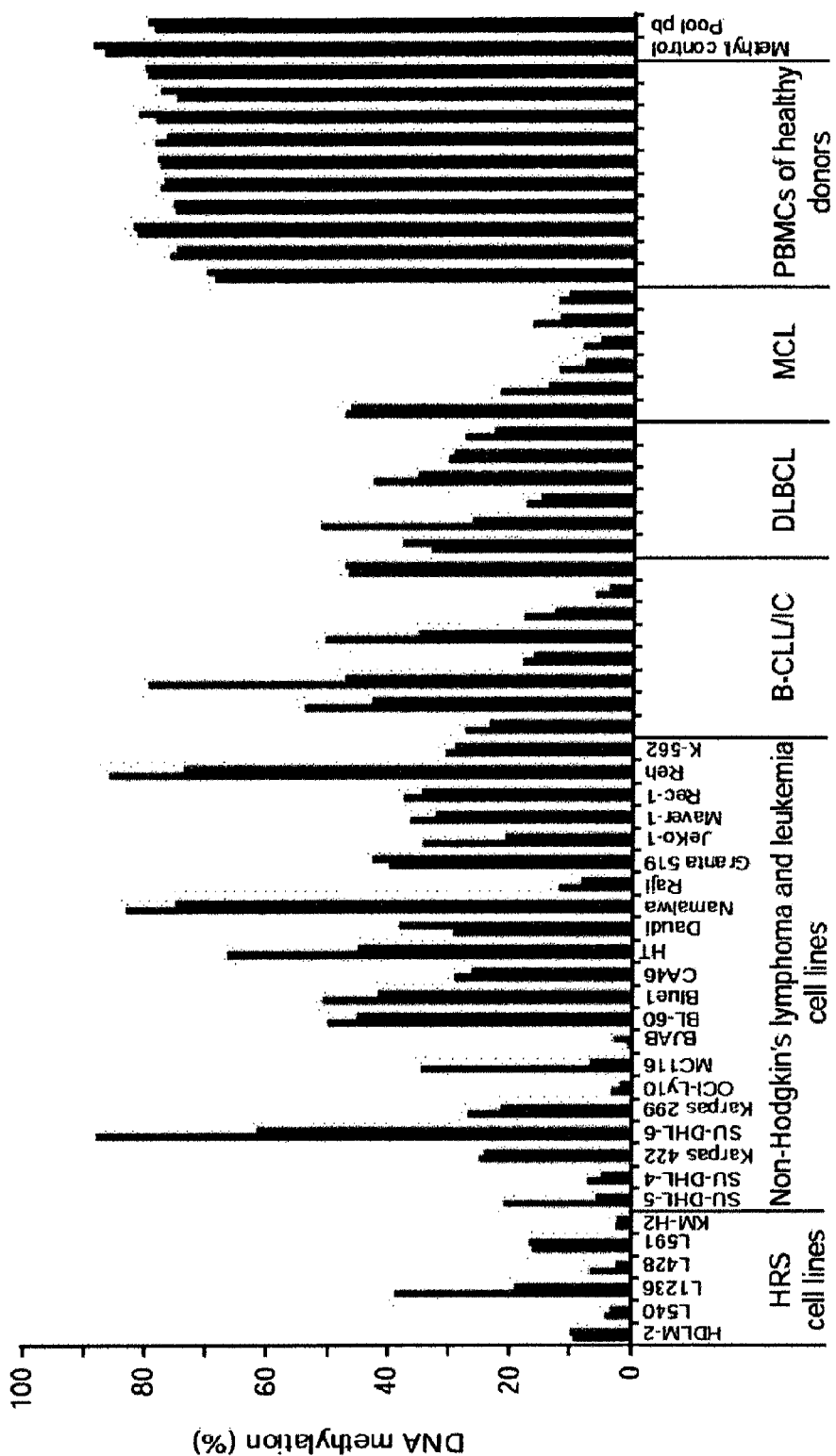

FIG. 12 Analysis of CSF1R LTR DNA methylation and CBFA2T3 expression. Analysis of DNA methylation of two CpG elements of the CSF1R LTR by bisulfite pyrosequencing in various cell lines, primary lymphoma samples and nonmalignant primary hematopoietic cells. For each sample, the amount of DNA methylation is shown as a percentage for each individual CpG element. B-CLL/IC, B cell chronic lymphocytic leukemia/immunocytoma; DLBCL, diffuse large B cell lymphoma; MCL, mantle cell lymphoma; PMNCs, peripheral mononuclear cells of the blood. Methyl. control, in vitro-methylated control DNA; Pool pb, pooled DNA from PMNCs.

Figure 13:
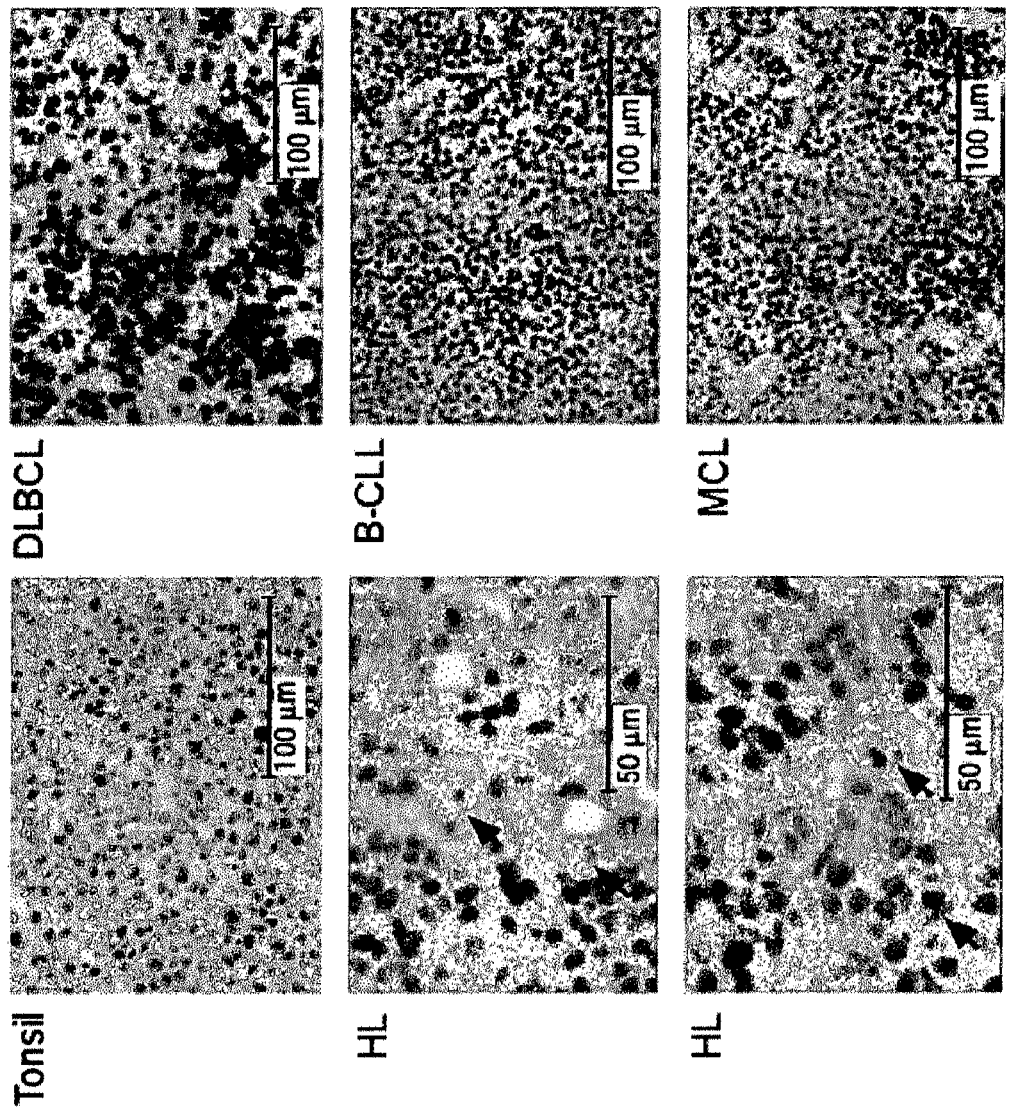

FIG. 13 Analysis of CSF1R LTR DNA methylation and CBFA2T3 expression. CBFA2T3 expression is lacking in primary HRS cells, full CSF1R LTR activation requires CBFA2T3 downregulation and active NF-kB, and THE1 activation occurs in HRS cells at many genomic locations. Immunohistochemistry (IHC) to detect CBFA2T3 expression in a germinal center in normal human tonsil tissue (Tonsil), two classical Hodgkin's lymphoma cases (HL; HRS cells are marked by arrows), and one case each of diffuse large B cell lymphoma (DLBCL), B cell chronic lymphocytic leukemia (B-CLL) and mantle cell lymphoma (MCL), respectively. Apart from HRS cells, nuclear staining of CBFA2T3 is observed in most cells. The IHC staining shown is representative for the respective lymphoma type.

Figure 14:
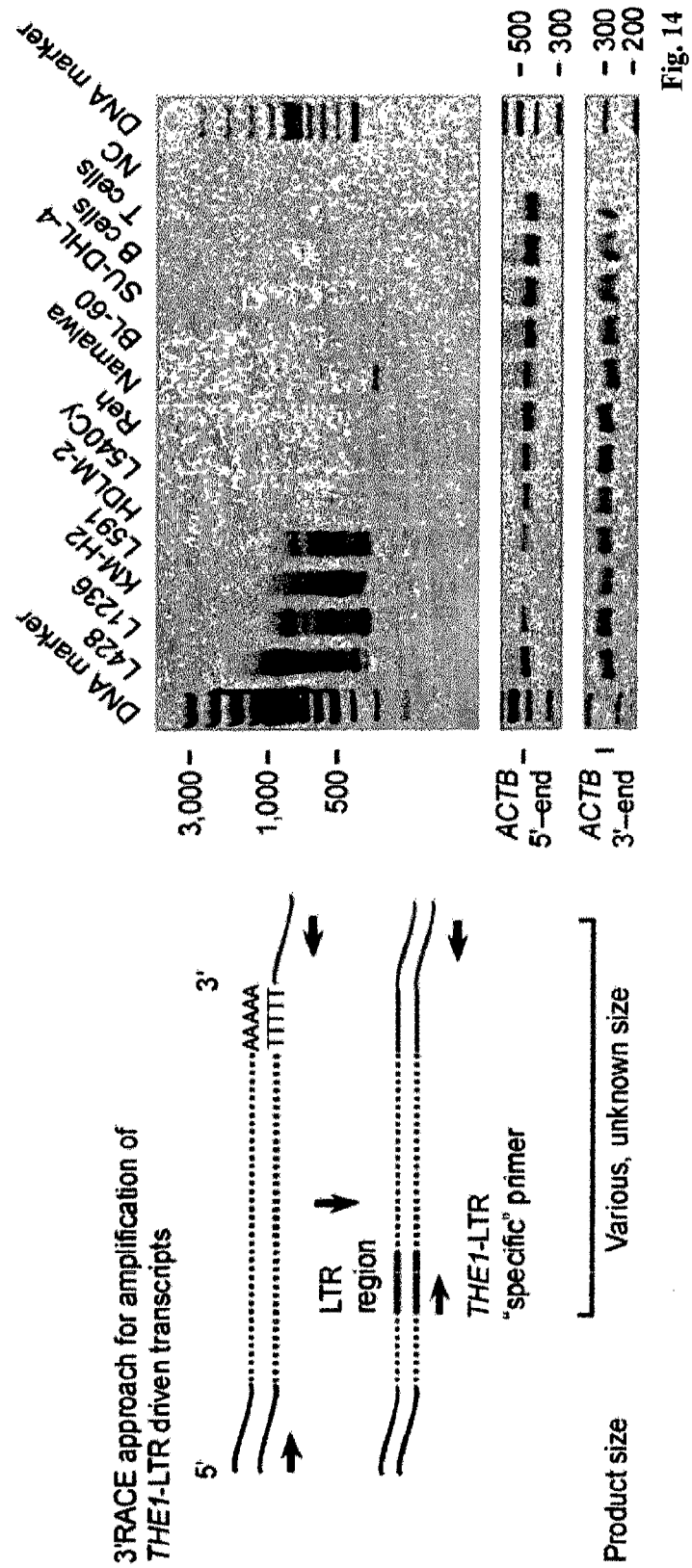

FIG. 14 Analysis of CSF1R LTR DNA methylation and CBFA2T3 expression. CBFA2T3 expression is lacking in primary HRS cells, full CSF1R LTR activation requires CBFA2T3 downregulation and active NF-kB, and THE1 activation occurs in HRS cells at many genomic locations. 3' RACE analysis detecting multiple full-length mRNAs starting from THE1 LTRs in HRS cells. 3' RACE was performed with forward THE1B primer_2 (FIG. 18C) and a reverse primer recognizing a tagging sequence, as depicted in the schematic on the left. In HRS cells, bands of multiple sizes were amplified. 5' and 3' ends of ACTB (beta-actin) were analyzed by 5' RACE and 3' RACE, respectively, as internal controls. As a negative control, water was used instead of cDNA (NC). One of three experiments is shown.

Figure 15:
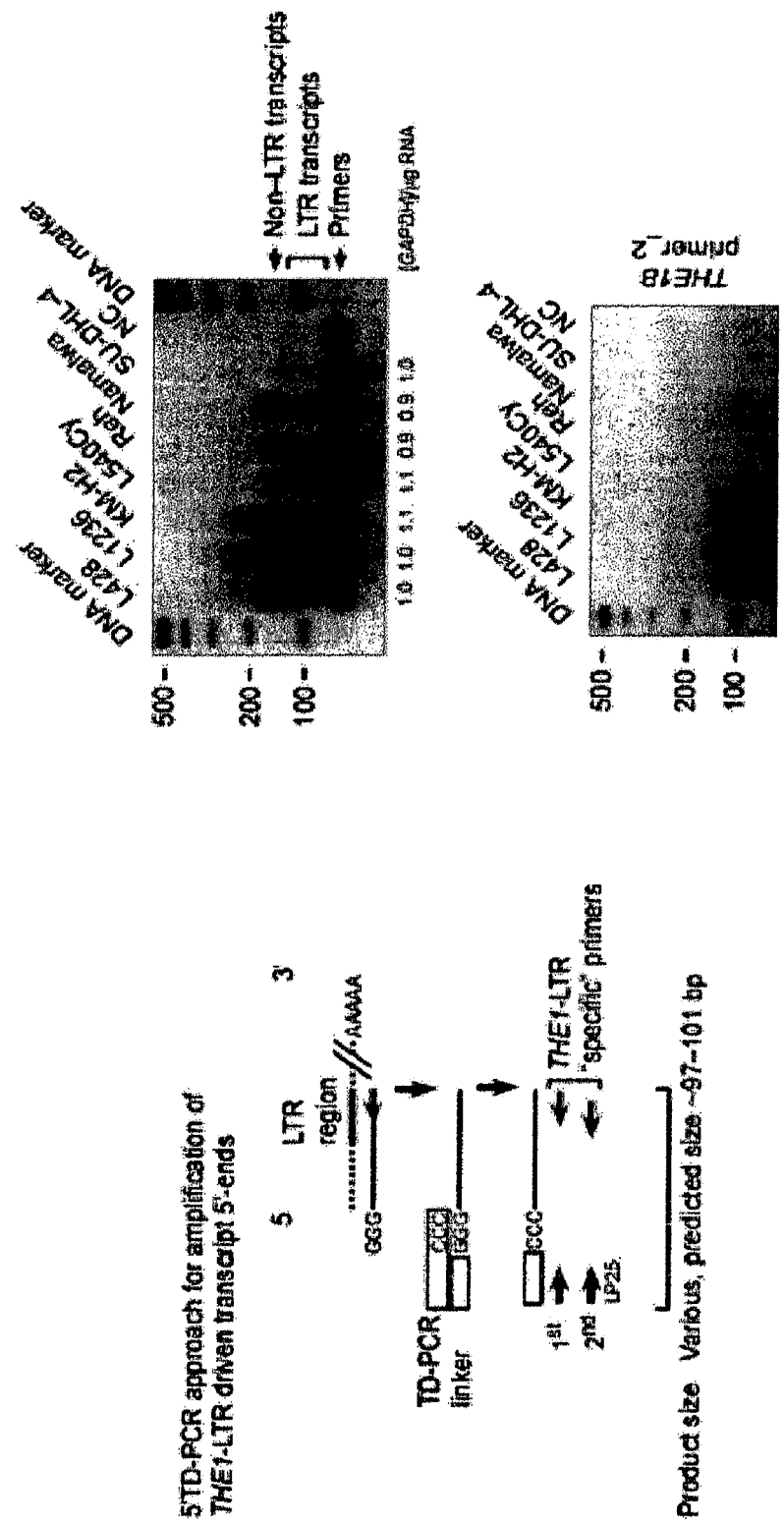

FIG. 15 CBFA2T3 expression is lacking in primary HRS cells, full CSF1R LTR activation requires CBFA2T3 down-regulation and active NF-kB, and THE1 activation occurs in HRS cells at many genomic locations. Top, 5' RACE of LTR RNAs performed by TD-PCR using the reverse THE1B primer_1 in combination with the reverse CSF1R primer_1 (FIG. 18C), as depicted in the schematic on the left. The bracket to the right of the gel indicates products that fall within the predicted size range of THE1 products. The black arrow indicates an unexpected product that could not be re-amplified by nested PCR. As a control, the relative amounts of amplified GAPDH mRNA per mg RNA for each sample is shown. As negative control, water was used instead of cDNA (NC). Below, nested PCR of 5' RACE TD-PCR products. DNA fragments migrating within the bracketed region of predicted THE1 products (top gel) were subjected to nested PCR with primer LP25 and the reverse THE1B primer_2. This primer pair is predicted to generate THE1A or THE1B family LTR products of ~97-101 bp. DNA migrating within this size range was purified and subcloned for sequencing. As negative control, water was used instead of cDNA (NC). One of two experiments is shown.

Figure 16:
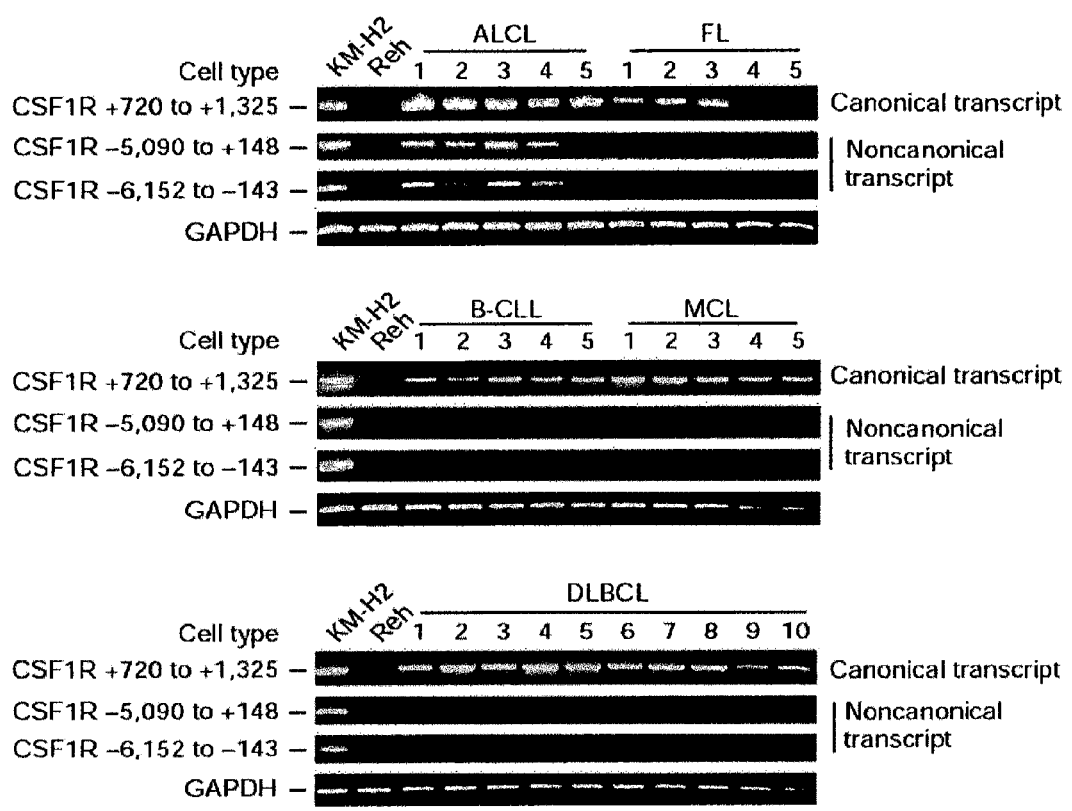

FIG. 16 LTR-CSF1R transcripts are expressed in anaplastic large cell lymphoma (ALCL) specimens. Total RNA was extracted from frozen lymph node tissue sections of five cases each of anaplastic ALCL, follicular lymphoma (FL), B-CLL and MCL, and ten cases of DLBCL. Expression of the canonical and noncanonical CSF1R transcripts was analyzed by RT-PCR, as indicated. KM-H2 and Reh cells were used as controls. GAPDH expression was analyzed as a control. One representative of three experiments is shown.

FIG. 17 Transcribed THE1B and THE1A family LTR promoters. Alignment of the promoters of the transcribed THE1B and THE1A LTRs identified by 5'RACE in HRS cells (see FIGS. 8 and 13 to 15). Conserved transcription factor motifs are highlighted in bold, and those sites that were mutated in the promoter analyses (FIG. 6d) have their names underlined. Transcription initiation sites are shown in bold and underlined. For clone 715, lower case represents transcribed sequences present in the 5'RACE clone. For clone 713, the underlined section represents a directly repeated region, and two alternative alignments of this region are shown. For the CSF1R-LTR the underlined base represents the endpoint of the −142 promoter (FIG. 6c). The LTRs in clones 702, 703 and 709 were identified by RACE more than once in this study. The THE1B consensus sequence was obtained from Repbase (Jurka, J. et al., *Cytogenetic and Genome Research* 110, 462-267 (2005)) (THE1B consensus (SEQ ID NO 95), CSF1R THE1B (SEQ ID NO 96), 703 THE1B (SEQ ID NO 97), 707 THE1B (SEQ ID NO 98), 709 THE1B (SEQ ID NO 99), 712 THE1B (SEQ ID NO 100), 715 THE1B (SEQ ID NO 101), 716 THE1B (SEQ ID NO 102), 702 THE1B (SEQ ID NO 103), 713 THE1B (SEQ ID NO 104)).

FIG. 18 (A) Alignment of conserved DNA sequences within the consensus THE1B-LTR (SEQ ID NO 106) and the CSF1R-LTR (SEQ ID NO 105). The indicated transcription factor consensus motifs and the underlined predicted transcription initiation sites are highlighted in bold. Position −142 representing the end-point of the fully functional CSF1R-LTR promoter (FIGS. 6c and 6d) is also underlined. Transcription factor motifs that were mutated in subsequent promoter analyses (FIG. 6d) have their names underlined. All CG motifs are double underlined and highlighted in grey. The ancestral THE1B element is predicted to have contained 13 CG motifs, but in the CSF1R-LTR, and most other THE1B elements, the majority of these have mutated to either TG or the complementary CA (see also FIG. 18B). (B) CG content of conserved THE1B-LTR elements. Listed here are the 10 most highly conserved THE1B elements in the human genome. These full length LTRs show an average of 94% homology with the ancestral THE1B element but have an average of just 3 CG motifs per LTR. Note that half of the variation from the consensus in these elements can be accounted for by mutations in CG motifs, and that this analysis may be biased towards LTRs with a higher CG content. The mutated CG motifs presumably existed in a predominantly methylated state prior to their mutation as they exhibit an accelerated mutation rate relative to other bases in the LTR. (THE1B 181 (SEQ ID NO 108), CSF1R 173 (SEQ ID NO 107, THE1B primer_1 (SEQ ID NO 109), THE1B primer_2 (SEQ ID NO 110), CSF1R primer_1 (SEQ ID NO 111), CSF1R primer_2 (SEQ ID NO 112)) (C) Sequence conservation and PCR primer strategies. Alignment of DNA sequences within the consensus THE1B-LTR and the CSF1R-LTR. The underlined predicted transcription initiation site is highlighted in bold. Predicted splice sites are marked by a slash, with the consensus intron splice junction sequence shown in lower case. Sequences employed as PCR primers are depicted above and below the corresponding sequences.

Figure 19:
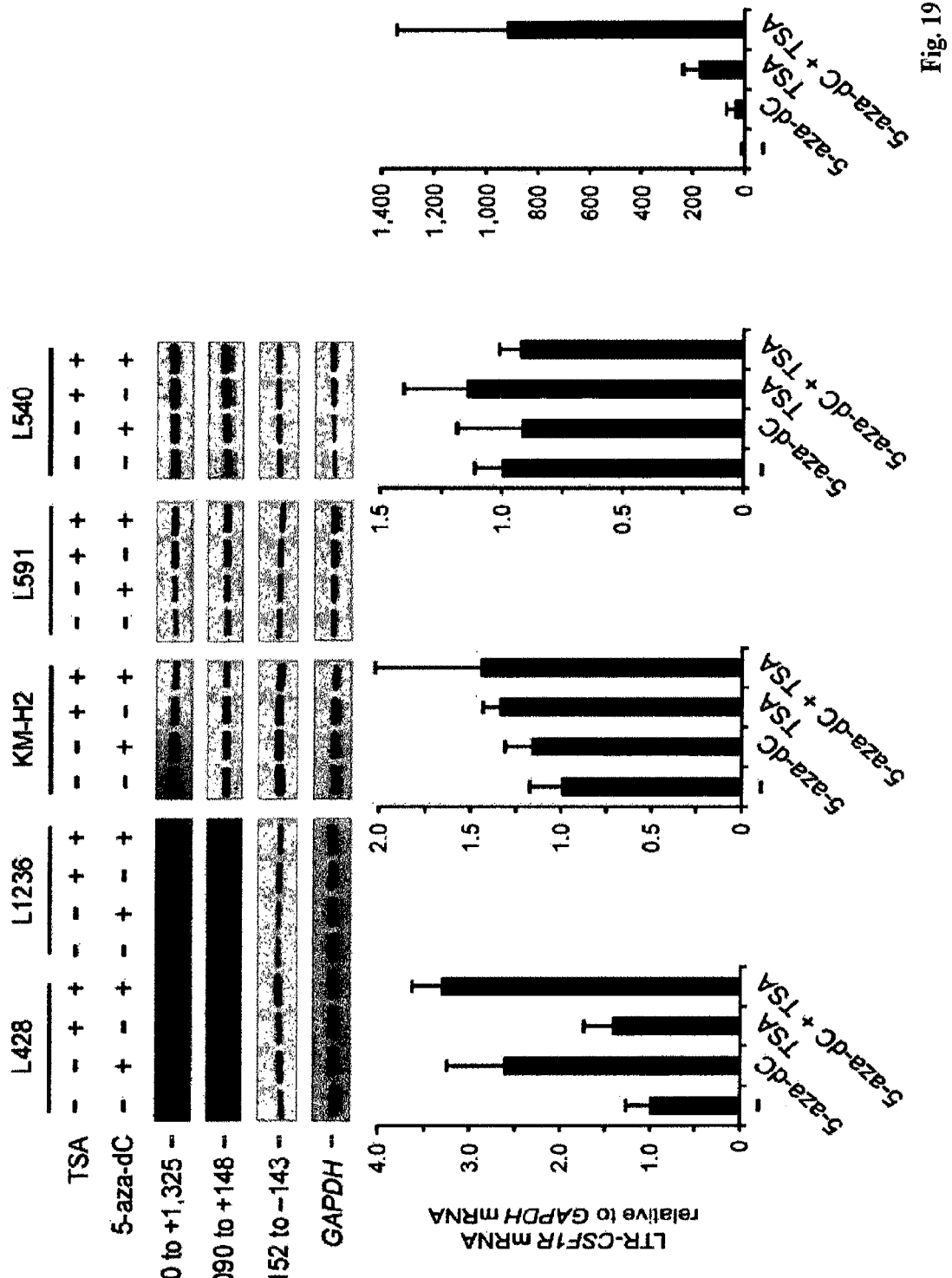

FIG. 19 Analysis of CSF1R transcripts in HRS cell lines following treatment with 5-aza-dC and TSA. Various HRS cell lines were left untreated or treated with 5-aza-dC, TSA, or 5-aza-dC in combination with TSA, as indicated. The expression of canonical and non-canonical CSF1R transcripts was analyzed by RT-PCR (upper panel; GAPDH was analyzed as a control) or by real-time PCR (lower panel; non-canonical transcript using primers −6,152 to −143; bars denote 95% CI). One representative out of three experiments is shown. Note, that among HRS cell lines only L428 and L1236 (with a lower steady-state expression level compared to e.g. KM-H2 or L540 cells, FIG. 1A) cells show weak alterations of LTR-CSF1R transcripts. In contrast, these transcripts are strongly induced in the non-Hodgkin cell line Reh, which is shown for comparison on the far right.

Figure 20:
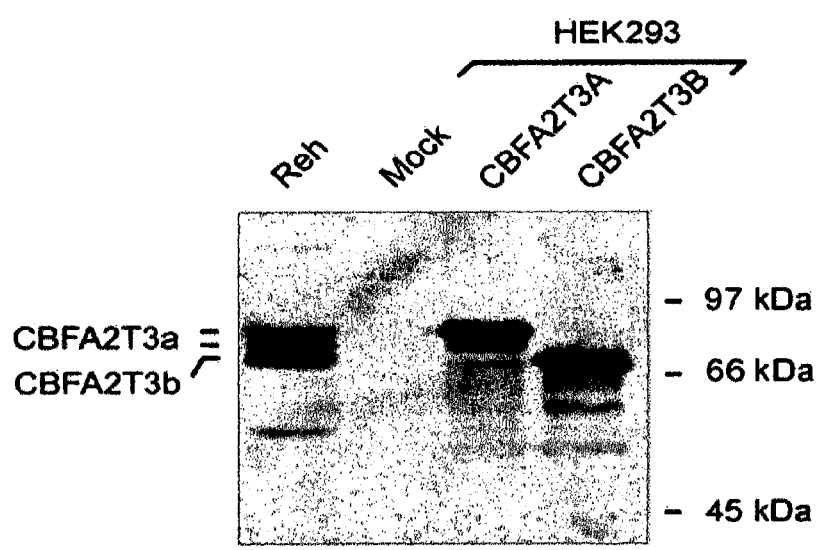

FIG. 20 Western blot analysis showing expression of CBFA2T3a and b isoforms in the non-Hodgkin cell line Reh and in HEK293 cells with ectopic expression of CBFA2T3a or CBFA2T3b. HEK293 cells were transfected with expression plasmids encoding CBFA2T3a or CBFA2T3b or the respective control (Mock). 48 hours after transfection whole cell extracts were prepared which were used as reference extracts for comparison with detected bands in the non-Hodgkin cell line. The Western blot analysis was performed by use of a rabbit polyclonal antibody to CBFA2T3. Positions of CBFA2T3a and b are indicated. A molecular weight standard is indicated on the right. kDa, kilodalton.

FIG. 21 Methylation of the CBFA2T3 promoter region 5 in various primary lymphoma samples and non-malignant hematopoietic cells. Six CpGs of the CBFA2T3 DNA region 5 (see FIG. 7d) were analyzed for DNA methylation by bisulfite-pyrosequencing in various primary human lymphoma samples and non-malignant hematopoietic cells (PMNC of healthy donors). For each sample, the amount of DNA methylation is shown in % for each individual CpG. B-CLL/IC, B cell chronic lymphocytic leukemia/immunocytoma; DLBCL, diffuse large B cell lymphoma; BL, Burkitt's lymphoma; MCL, mantle cell lymphoma; PMNC, peripheral blood mononuclear cells. Methyl. control, in vitro methylated control DNA; Pool pb, pooled DNA from PMNC of 9 male and female healthy donors.

FIG. 22 Induction of LTR-driven CSF1R transcripts following down-regulation of CBFA2T3; analysis of CBFA2T3 protein expression following treatment of Hodgkin and non-Hodgkin cell lines with 5-aza-dC and/or TSA. (a) The non-Hodgkin cell line Reh was transiently transfected with either control shRNA plasmid (Mock) or shRNA construct targeting CBFA2T3, both along with pEGFP. 72 h after transfection, GFP-positive cells were enriched, and mRNA expression of the non-canonical CSF1R transcript was analyzed by real-time PCR using primers −6152 to −143. Bars denote 95% CI. One representative out of three experiments is shown. (b) The Hodgkin cell lines L428, L1236 and KM-H2 and the non-Hodgkin B cell lines Reh and Namalwa were left untreated or treated with 5-aza-dC, TSA, or 5-aza-dC in combination with TSA. CBFA2T3 protein expression was analyzed in whole cell extracts by Western blotting. beta-actin was analyzed as a control. Note, that, in agreement with the unchanged expression levels of CSF1R transcripts in HRS cell lines (FIG. 19), no changes of CBFA2T3 protein expression were observed in HRS cell lines following 5-aza-dC and/or TSA treatment. Note, that CBFA2T3a and b isoforms are not just as well separated as in FIG. 7b and FIG. 20, and therefore bands are marked as 'CBFA2T3'. n.s., non-specific.

Figure 23A:
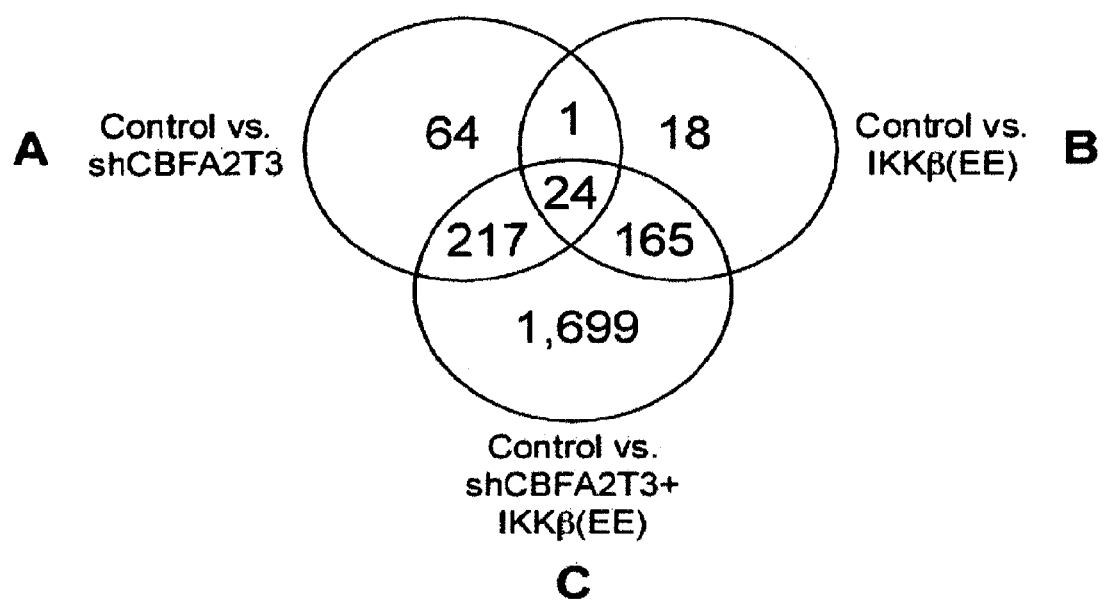
Figure 23B:
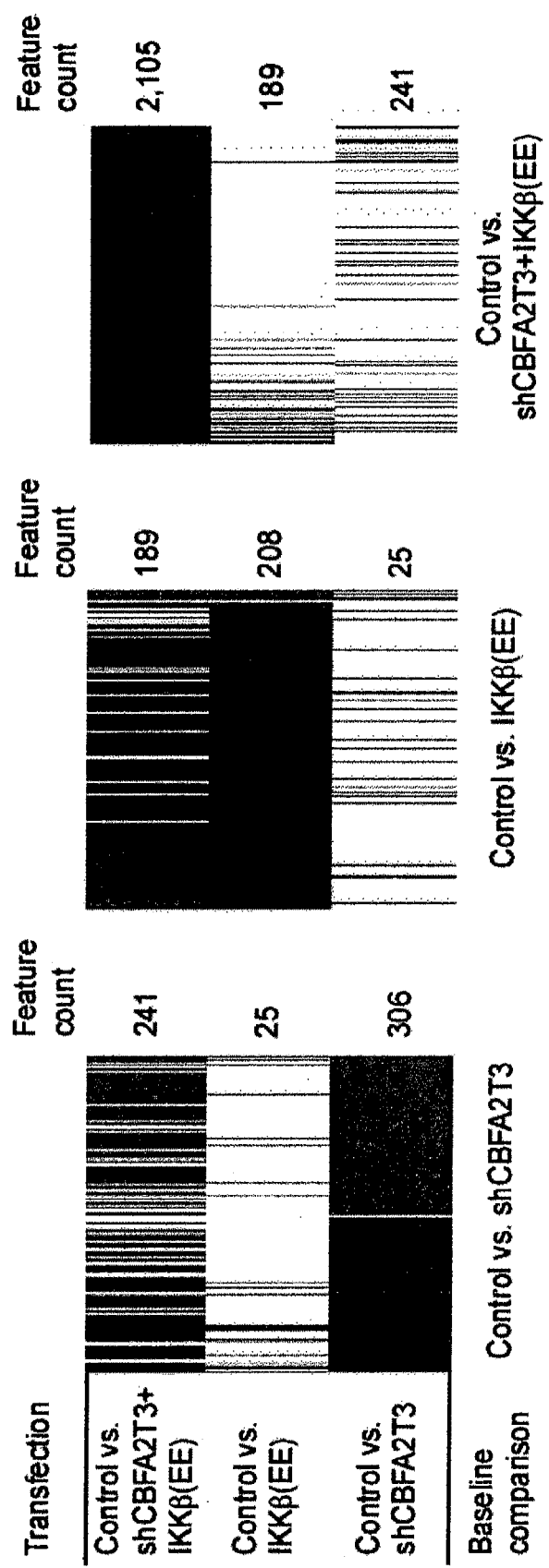

FIG. 23 Impact of CBFA2T3 knockdown and ectopic IKK-b(EE) expression on the gene expression profile of Reh cells. Cells of the non-Hodgkin B cell line Reh were transfected in duplicate with different combinations of vectors encoding shCBFA2T3 and/or IKKb(EE) or respective control plasmids along with pEGFP. 72 h after transfection, pEGFP+ cells were enriched by flow cytometry, and total RNA was used for gene expression profiling (Affymetrix Human Genome U133 Plus 2.0 arrays). After RMA background correction and quantile normalization of the raw data, data were variance-filtered with an interquartile range cutoff of 0.5. Significantly deregulated features were extracted using LIMMA with an adjusted p-value cutoff of 0.05 and a log 2-fold change cutoff of 0.5. Adjusted p-values were calculated using the Benjamini & Hochberg method to correct for multiple testing. (a) The number of differentially expressed features after CBFA2T3 inhibition (shCBFA2T3; A; n=306), after ectopic expression of IKKb(EE) (B; n=208) or after their combination (C; n=2, 105) were used to construct a Venn diagram demonstrating the extent of overlapping genes. Note, that shCBFA2T3 and IKKb(EE) alone regulate each a limited number of genes with only a small overlap, whereas combination of both results in a dramatic synergistic regulation of gene expression. (b) Heat diagrams show the overlap of all comparisons with the indicated baseline comparison. For each corresponding scheme, the number of significantly deregulated features is stated. The color code indicates the relative up- (red) or down- (green) regulation.

FIG. 24 Supplementary FIG. 11 Examples of polyadenylated mRNAs originating in THE1-LTRs identified by 3'RACE PCR. Amplification and sequencing of mRNAs was as described in Table 5 (designation Clone 1 to Clone 4 is identical to Table 5 and refers to the same identified sequence, respectively). The chromosomal location resp. alignment of each sequence is according to the hg19 sequence.

Figure 25:
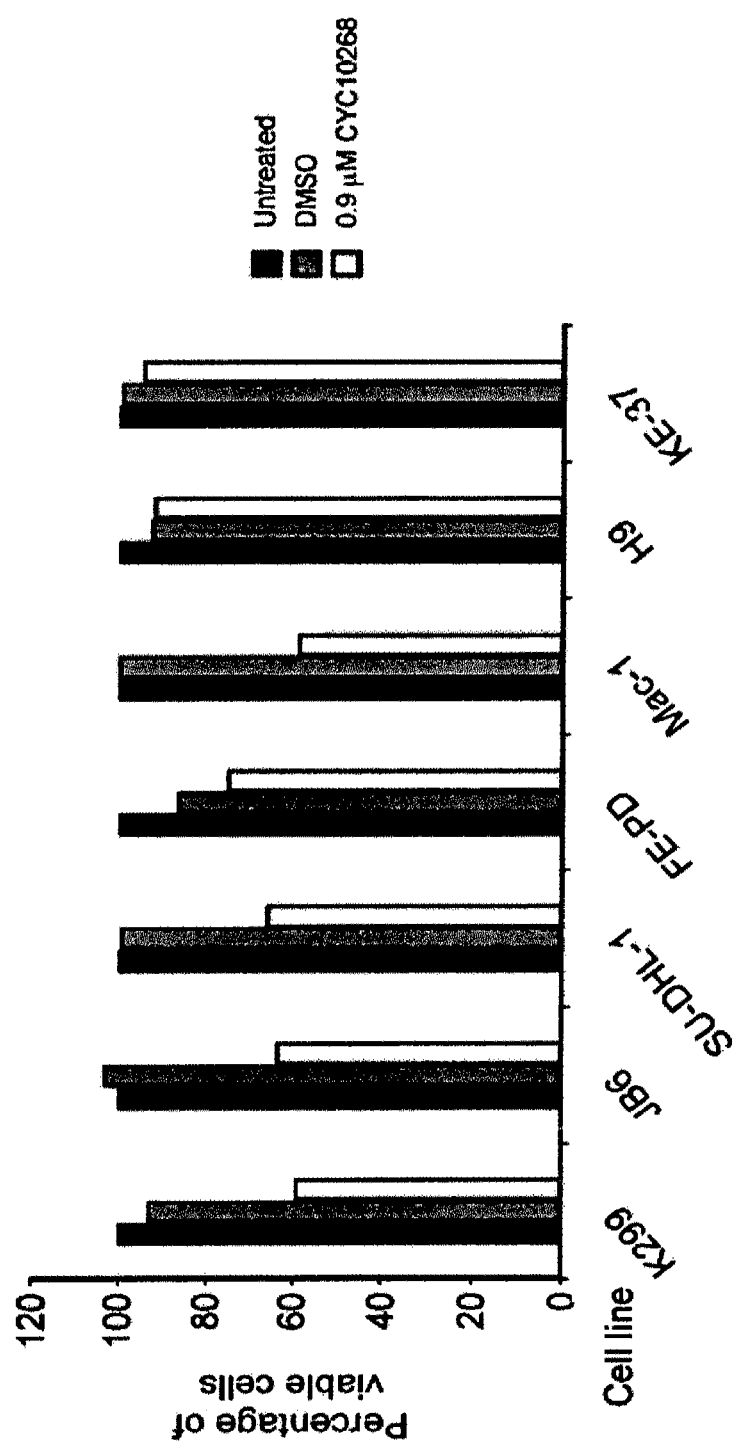

FIG. 25 CSF1R inhibition induces apoptotic cell death in anaplastic large cell lymphoma (ALCL) cell lines but not control T cell lymphoma derived cell lines. Various ALCL (K299, JB6, SU-DHL-1, FE-PD, Mac-1) and non-ALCL T cell-derived control cell lines (H9, KE-37) were left untreated, or treated with the CSF1R inhibiting compound CYC10268 or the DMSO control, respectively. After 96 hours, the percentage of viable cells was determined by annexin V-FITC/PI staining and flow cytometry. One representative out of three experiments is shown.

EXAMPLES

Results

HRS Cell-Specific Expression and Activity of CSF1R and CSF-1.

The inventors analyzed a panel of HRS cell-derived and non-HRS B cell lines for CSF1R and CSF-1 mRNA and protein expression (FIG. 1A-1D). Expression of both genes was absent in all B cell-derived non-HRS cell lines. In contrast, all HRS cell lines aberrantly expressed both genes (FIG. 1A and FIG. 9A). mRNA expression data largely correlated with protein expression of CSF1R (FIG. 1B), even though CSF1R expression was weak at the cell surface of some HRS cell lines, and CSF-1 measured by flow cytometry and by ELISA (FIGS. 1C and 1D), respectively.

Figure 1E:
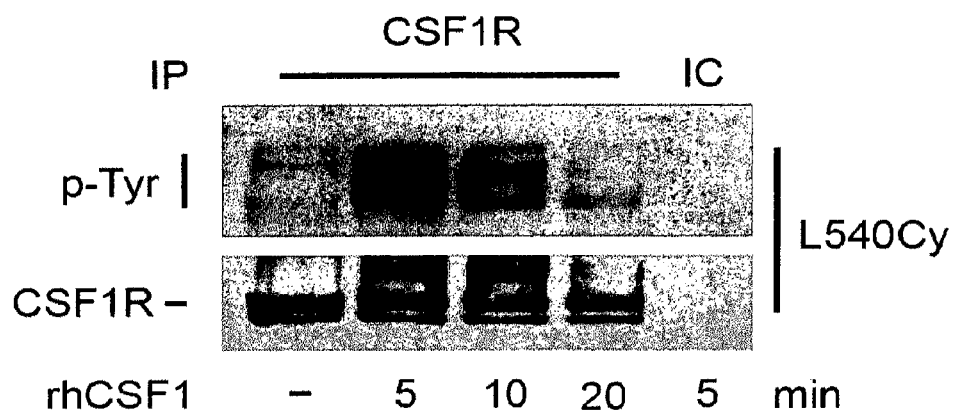
Figure 1F:
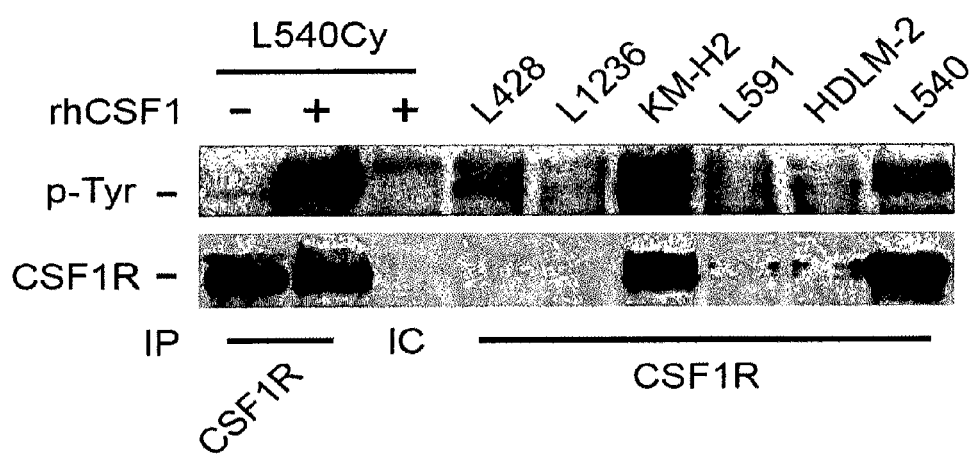
Figure 1G:
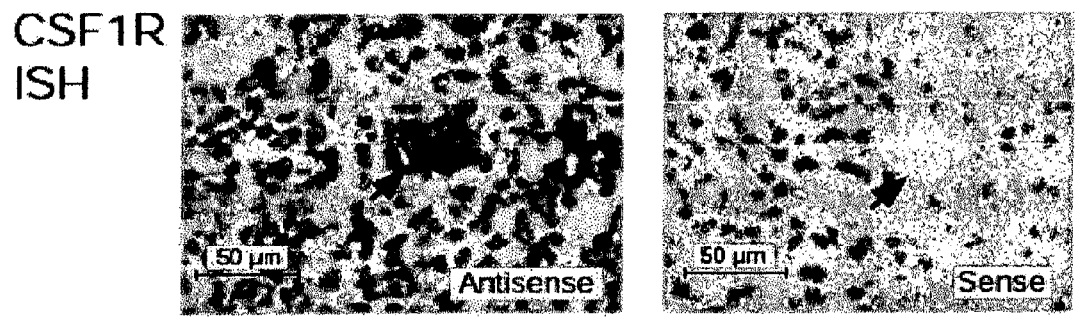

To investigate CSF1R functionality in HRS cell lines, cell lines with CSF1R but low CSF-1 expression were stimulated with rhCSF-1. Following stimulation of L540Cy cells, CSF1R was immunoprecipitated and activation was determined by analyzing its phosphorylation (Pixley and Stanley, 2004) (FIG. 1E). A rapid increase in tyrosine phosphorylation from a basal level was observed. The fact that this basal level could measured prompted testing whether the production of CSF-1 resulted in an autocrine or paracrine activation of CSF1R in HRS cell lines. Therefore, unstimulated HRS cell lines were investigated for CSF1R tyrosine phosphorylation, which showed that CSF1R was constitutively activated, most prominent in L428, KM-H2 and L540 cells (FIG. 1F). Finally, elevated expression levels of CSF1R were confirmed by RNA in situ hybridization (ISH) in HRS cells of all ten HL patient samples analyzed (FIG. 1G); expression of CSF-1 in HRS cells of HL patient samples has been previously described (Moreau et al., 1992).

CSF-1 Expression is NF-κB Dependent and HRS Cell Survival Depends on CSF1R Signaling.

Since high level activity of transcription factor nuclear factor kappa B (NF-κB) is a hallmark of HRS cells (Hinz et al., 2002), and NF-κB has been implicated in CSF-1 regulation (Li et al., 2002), its contribution to CSF-1 expression in HRS cells was investigated (FIG. 2 and data not shown). L428 and KM-H2 cells were transfected with an expression vector encoding the NF-κB super-repressor IκBαΔN, and expression of CSF-1 was monitored by flow cytometry. CSF-1 was strongly down-regulated following NF-κB inhibition (FIG. 2), indicating that aberrant CSF-1 expression in HRS cell lines is primarily dependent on their constitutive NF-κB activity.

Figure 3A:
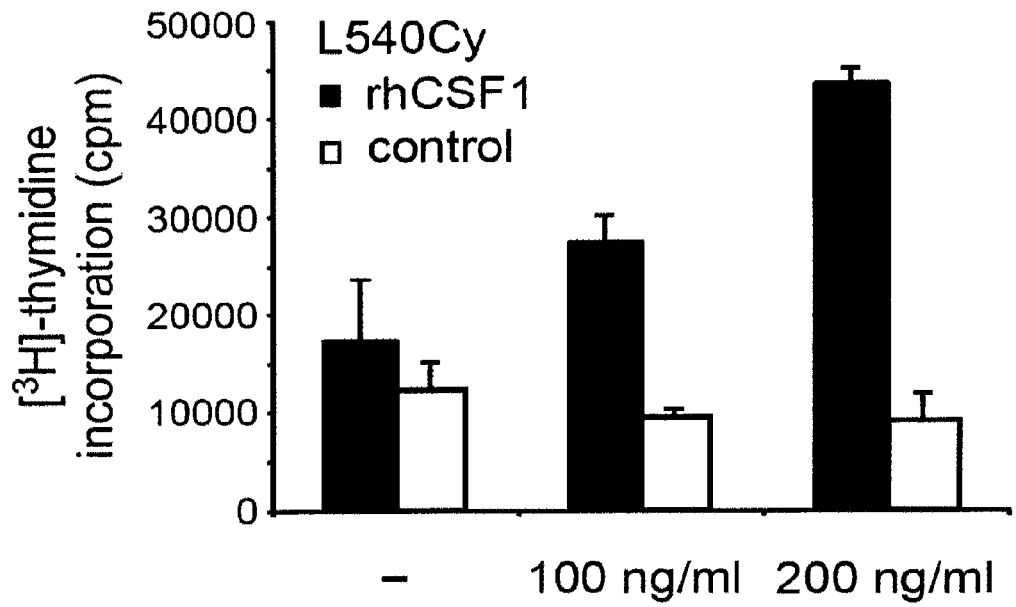
Figure 3B:
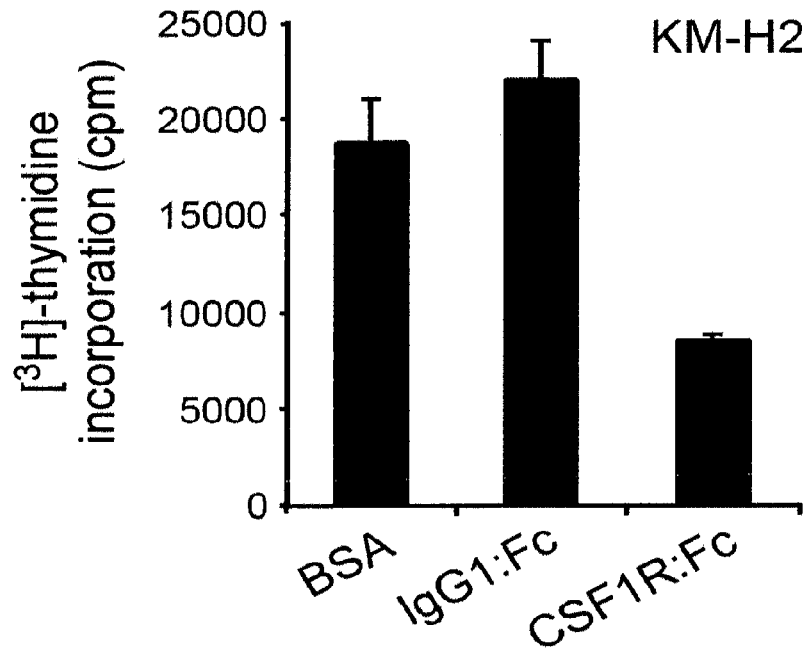
Figure 3C:
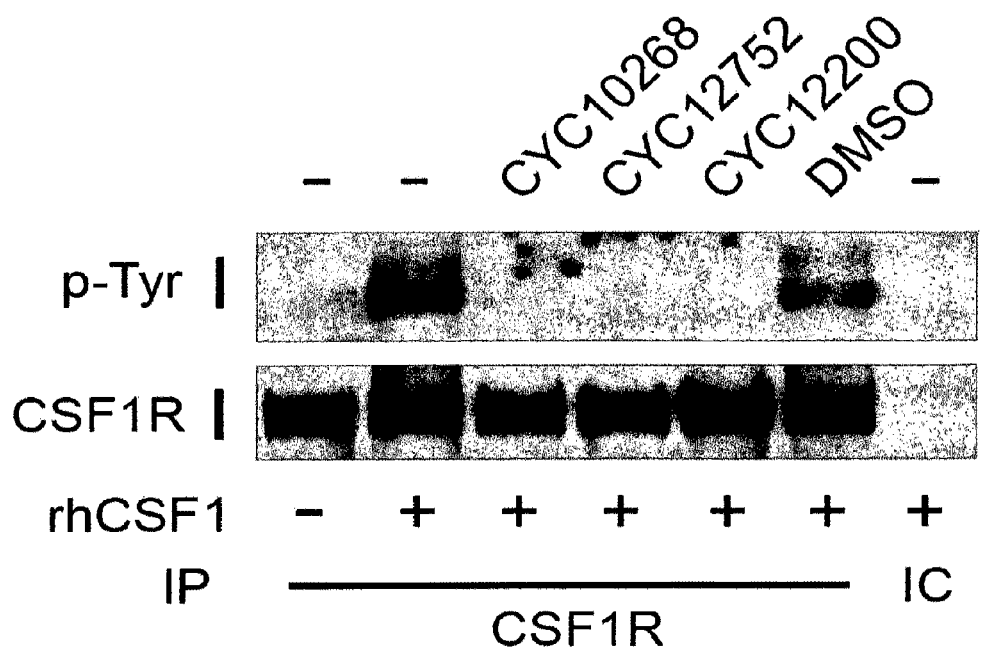
Figure 3D:
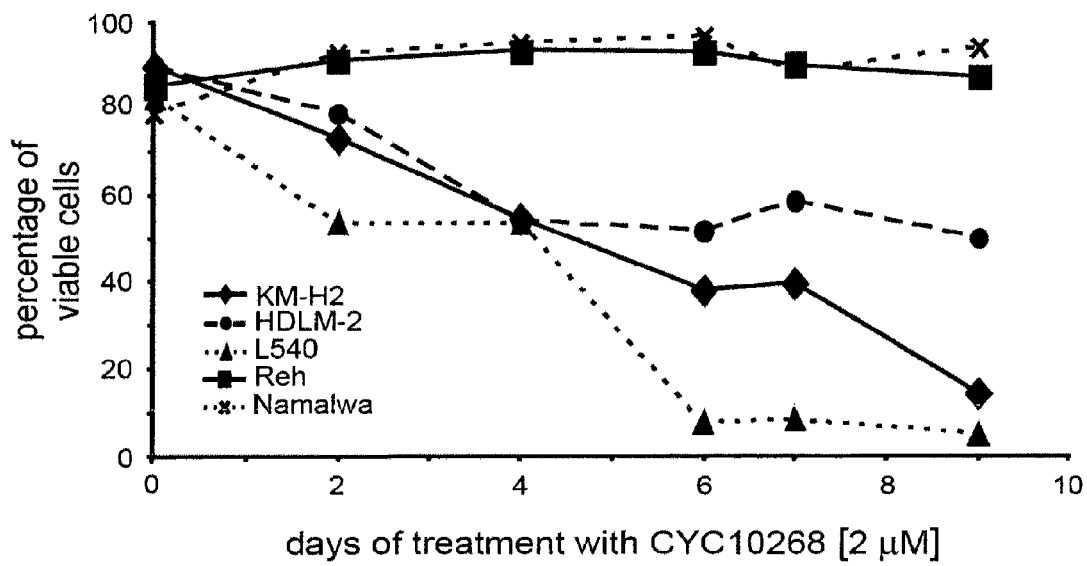

To address the functional consequences of CSF1R activity for HRS cell lines (FIG. 3), the effect of CSF1R activation on L540Cy cells was first investigated. Their stimulation with rhCSF-1 induced proliferation in a dose-dependent manner (FIG. 3A). In a complementary experiment, we treated KM-H2 cells, which highly express both CSF1R and CSF-1, with the decoy-receptor-like inhibitor CSF1R:Fc that binds to and neutralizes CSF-1 (FIGS. 3B and S1B), and observed a strong reduction of [$^3$H]-thymidine incorporation. These data implied that CSF1R activity supports HRS cell proliferation. To further substantiate this finding, we blocked this pathway more efficiently with the recently described CSF1R-specific inhibitory small compounds CYC10268, CYC12752 and CYC12200 (Burns et al., 2009; Irvine et al., 2006) (FIGS. 3C and 3D and Table 1). In our experimental settings, all three compounds efficiently blocked rhCSF-1 induced CSF1R phosphorylation in L540Cy cells (FIG. 3C), and treatment of various cell lines with these inhibitors induced, as determined by Annexin-V/PI staining, cell death in HRS cell lines. The non-HRS cell lines Reh and Namalwa, which lack CSF1R protein expression, remained unaffected (FIG. 3D and Table 1).

In summary, the data show that HRS cells express both CSF1R and CSF-1, establishing an autocrine/paracrine loop that is required for survival.

HRS Cells Express CSF1R from an Upstream Promoter.

In myeloid cells, CSF1R expression is controlled by a well defined set of cis-regulatory elements, namely the promoter and the c-fms intronic regulatory element (FIRE-enhancer) (Bonifer and Hume, 2008), which both are critically dependent on the transcription factor PU.1 (Bonifer and Hume, 2008). However, with the exception of L591 cells, expression of transcription factor PU.1 is lost in HRS cell lines and primary cells (FIG. 9C) (Jundt et al., 2002). To examine how CSF1R expression is activated in HRS cells despite the absence of PU.1 we measured transcription factor occupancy and chromatin accessibility of the CSF1R promoter by in vivo DNase I and DMS footprinting (FIG. 10A and data not shown). Myeloid-derived HL-60 cells express CSF1R from a myeloid-specific promoter, which binds transcription factors and forms a DNase I hypersensitive site (DHS) (Follows et al., 2003). Namalwa B cells served as negative control. As expected, HL-60 cells displayed increased DNase I accessibility at the promoter as indicated by high band intensity whereas band intensity in CSF1R non-expressing Namalwa cells was low. DMS in vivo footprinting confirmed that the CSF1R promoter in HL-60 indeed bound transcription factors (data not shown). To our surprise, we were unable to detect increased DNase I accessibility and transcription factor occupancy at the promoter region and FIRE-enhancer in any of the CSF1R-expressing HRS cell lines (FIG. 10A and data not shown). The absence of active chromatin at the CSF1R promoter region in HRS cell lines was further confirmed by ChIP assaying trimethylated histone H3 lysine 4 (H3K4me3) (FIG. 10B).

Figure 4A:
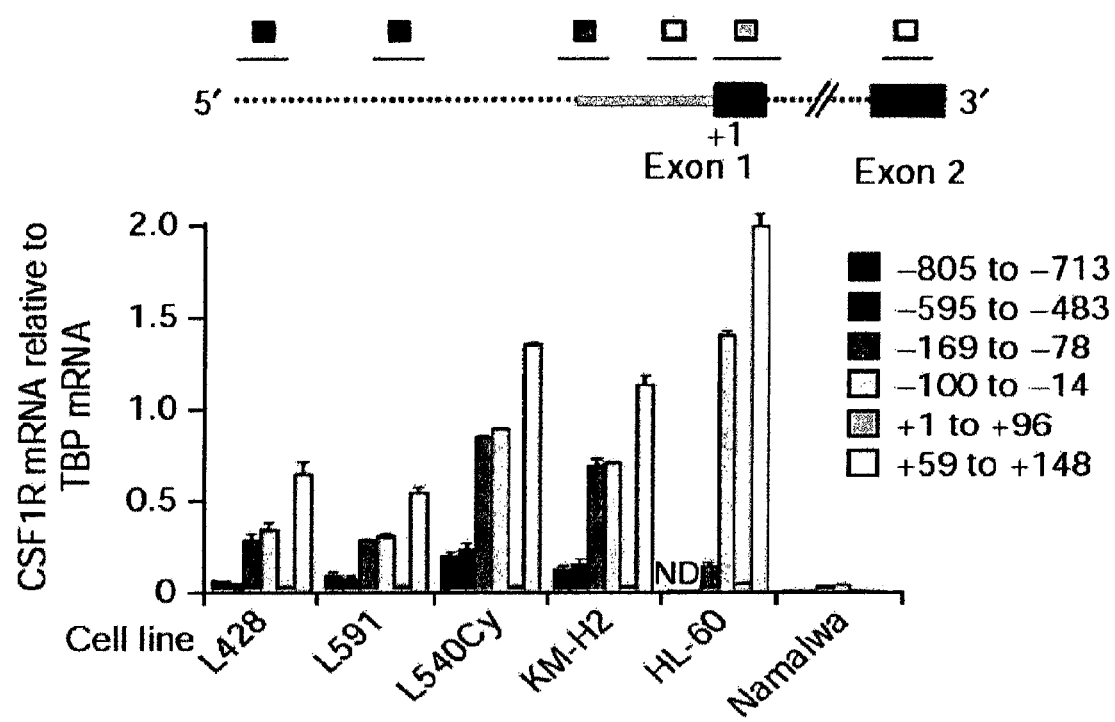
Figure 4B:
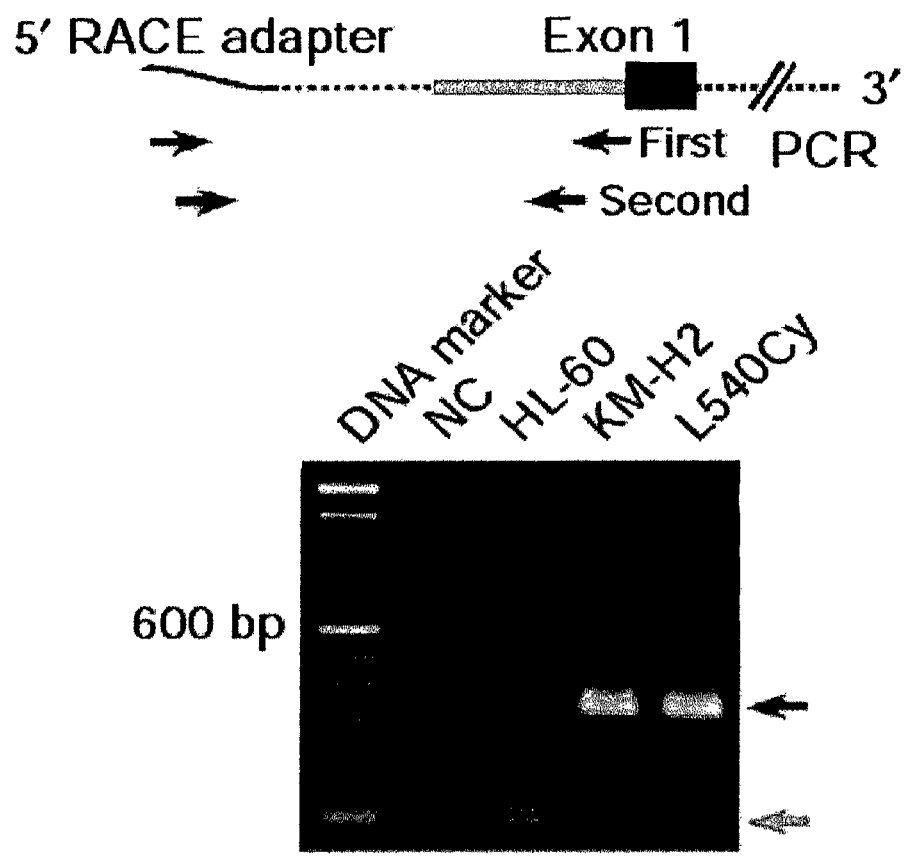

In human trophoblasts CSF1R is expressed from an alternative promoter 25 kB upstream of the myeloid promoter (Visvader and Verma, 1989). To test for the presence of longer transcripts in HRS cells, we performed real-time PCR using primers upstream of the known myeloid-specific transcription start site (TSS) (−805/−731, −595/−504 and −169/−97) (FIG. 4A). Amplification products in HRS but not HL-60 cells demonstrated the presence of upstream transcripts in HRS cells (FIG. 4A). 5'RACE analysis revealed that the CSF1R 5' ends in both analyzed HRS cell lines were approximately 250 bp longer compared to those in HL-60 cells (FIG. 4B). Aligning the sequenced reaction products to genomic DNA demonstrated that CSF1R transcripts in HL-60 cells originated from the known myeloid promoter (FIGS. 4C and S3) (in the following referred to as canonical transcripts). In contrast, HRS cells expressed a spliced CSF1R transcript originating ~6.5 kB upstream of the normal myeloid transcription start site (TSS) (FIGS. 4C and S3) (referred to as non-canonical transcripts) which is, however, outside the promoter region defined in trophoblasts.

Non-Canonical CSF1R Transcripts are Specific for HRS Cells.

We next analyzed expression of canonical and non-canonical CSF1R transcripts in the cell lines and in CD33-positive primary myeloid cells, using primers placed in the coding region of the gene (+720/+1304) as well as upstream of the myeloid promoter (−5090/+131 and −6152/−161) (FIGS. 5A and 5B). As expected, the +720/+1304 primers detected transcripts in all HRS and in primary myeloid cells, but not in control Reh and Namalwa cells. In contrast, expression of the non-canonical transcripts, analyzed with the −5090/+131 and −6152/−161 primer pairs, was restricted to HRS cell lines and was undetectable in the myeloid cells (FIG. 5B). This result was verified with primary HL patient samples whereby we examined mRNA isolated from frozen samples of HL-affected lymph nodes and, for comparison, primary human tonsils (FIG. 5C). Canonical CSF1R transcripts (+720/+1304) were detectable in all tonsils, likely originating from myeloid cells in this tissue. In contrast, non-canonical CSF1R transcripts (−5090/+131; −6152/−161) were exclusively detected in HL patient samples.

The Non-Canonical CSF1R Transcript in HRS Cells Initiates at an Aberrantly Activated Long Terminal Repeat (LTR).

Figure 6A:
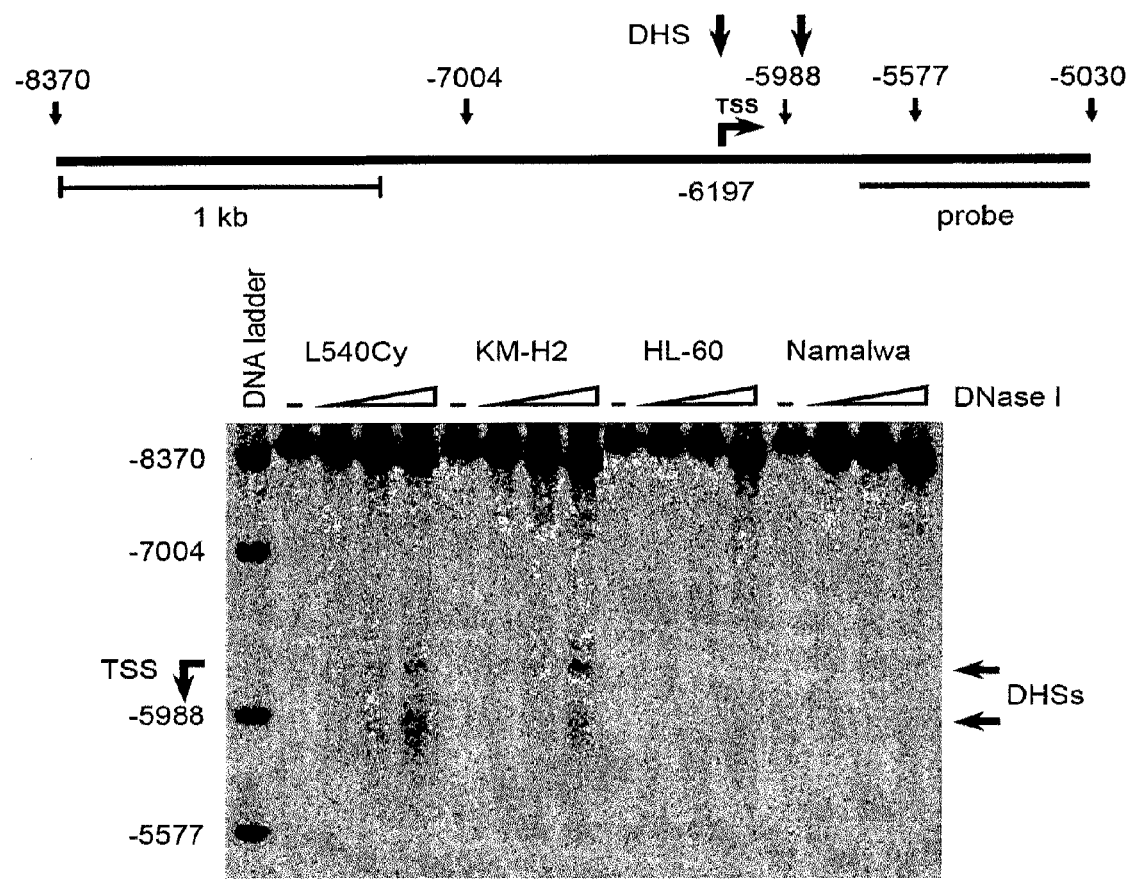
Figure 6C:
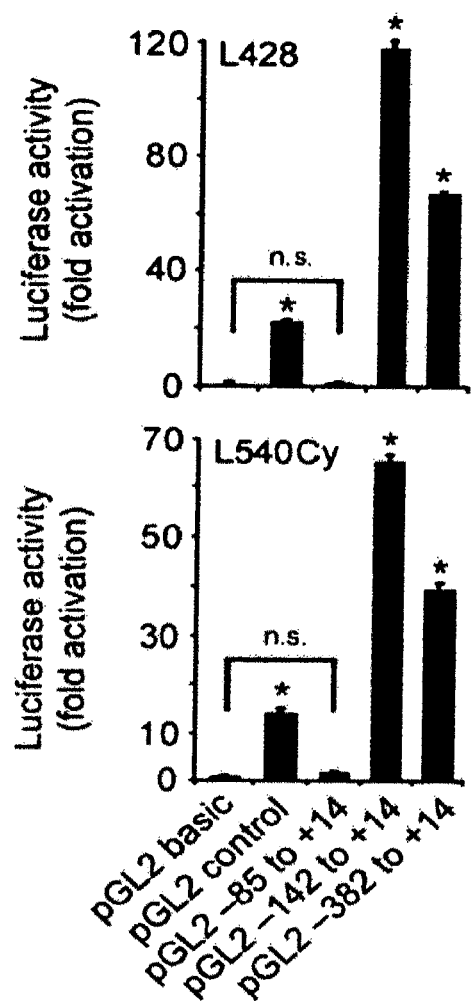

In order to characterize the upstream regulatory region in HRS cells in more detail, we performed DHS mapping in HRS and control cell lines (FIG. 6A). In contrast to control cells, we detected two DHS sites in HRS cells, one of which mapped to the TSS as identified by 5'RACE, indicating that this region indeed contained an active promoter. This was confirmed by ChIP using primers located within and outside this region demonstrating the association of RNA Polymerase II with this sequence in FIRS cells (data not shown).

Figure 6D:
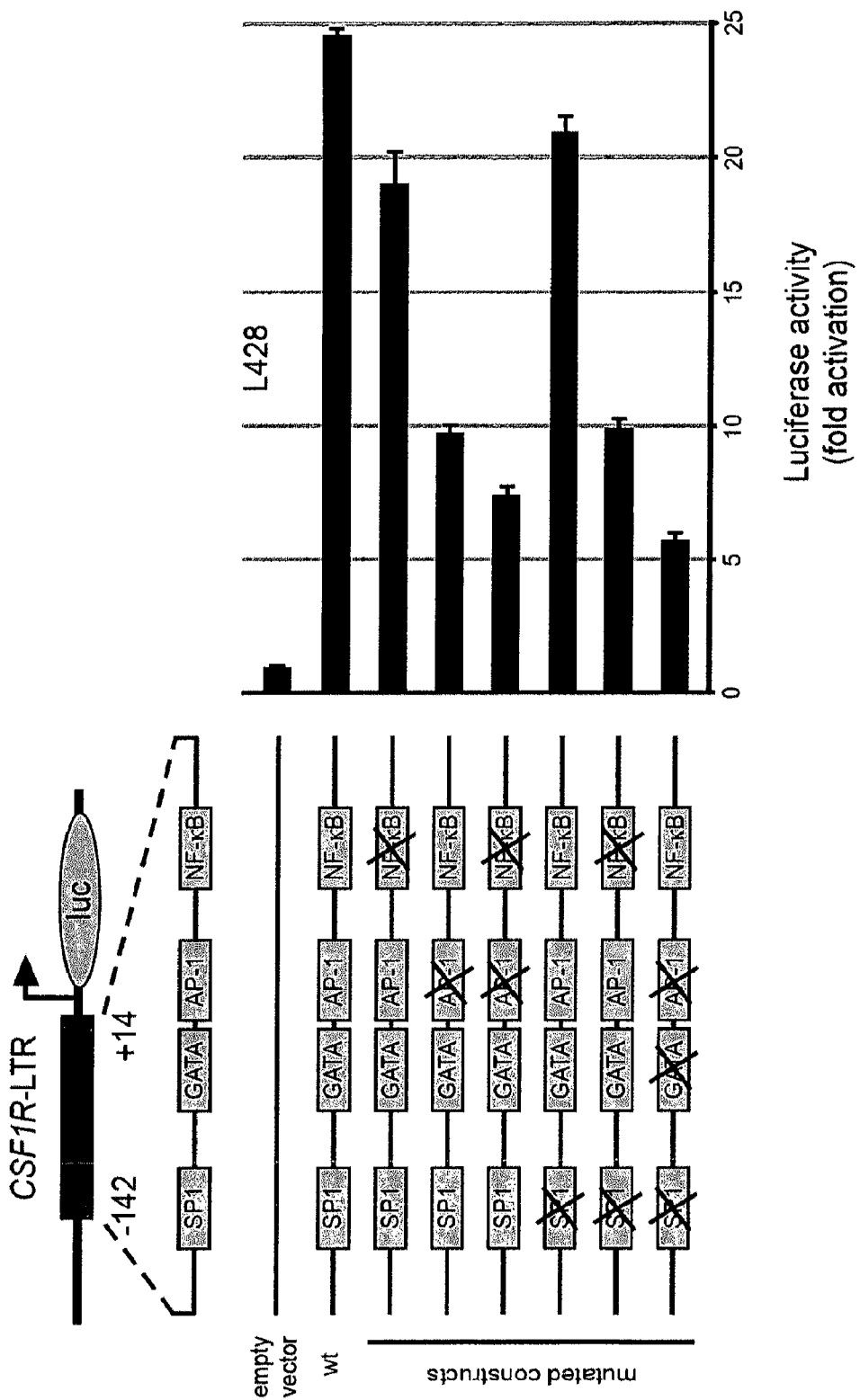

Closer inspection of the sequence around the TSS revealed that this sequence was not unique in the genome, but represented a LTR of the mammalian apparent LTR-retrotransposon (MaLR) family (Smit, 1993) (FIG. 6B). To confirm promoter activity of this element, we cloned different fragments upstream of the HRS cell-specific TSS (FIGS. 6B and 6C) (−85/+14; −142/+14; −382/+14) into the luciferase reporter vector pGL2 and analyzed promoter activity in HRS cell lines (FIG. 6C and data not shown). The strong activation of luciferase activity showed that the mapped TSS was indeed functional and that minimal promoter activity was located between −142 bp and +14 bp. The LTR region contained a number of putative binding sites for transcription factors (FIG. 6B) such as NF-κB, GATA, AP-1 and SP1, several of which are constitutively activated in HRS cells (Küppers, 2009). To determine the contribution of these transcription factors to LTR-activity in HRS cells, we altered these sites by point mutagenesis of the pGL2 −142/+14 construct. These experiments demonstrated that the combined activity of transcription factors NF-κB, SP1 and AP-1 was required for full LTR promoter activity (FIG. 6D and data not shown).

LTR De-Repression in HRS Cells is Linked to Loss of the Transcriptional Co-Repressor CBFA2T3.

Figure 7A:
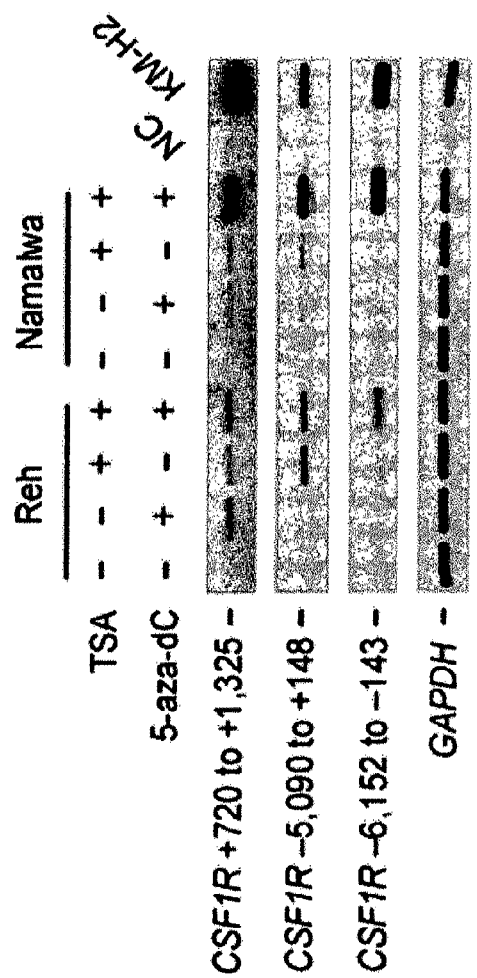

During evolution the human and mouse genome have accumulated a large number of LTRs derived from retroviral sequences (Jern and Coffin, 2008), which are epigenetically silenced early in development, usually by DNA methylation (Maksakova et al., 2008). We therefore hypothesized that the LTR de-repression in HRS cells may be caused by a loss of epigenetic control. To test this idea, we treated the non-HRS cell lines Reh and Namalwa with the DNA methyltransferase inhibitor 5-aza-2'-deoxycytidine (5-aza-dC) and/or histone-deacetylase inhibitor Trichostatin A (TSA) which alone or in combination are capable of activating epigenetically silenced genes, and assayed for the presence of canonical and non-canonical CSF1R transcripts (FIG. 7A). Both transcripts were weakly induced by 5-aza-dC or TSA alone, but we observed a synergistic activation following treatment with both agents (FIG. 7A). This indicated that this promoter was normally epigenetically silenced.

Figure 7C:
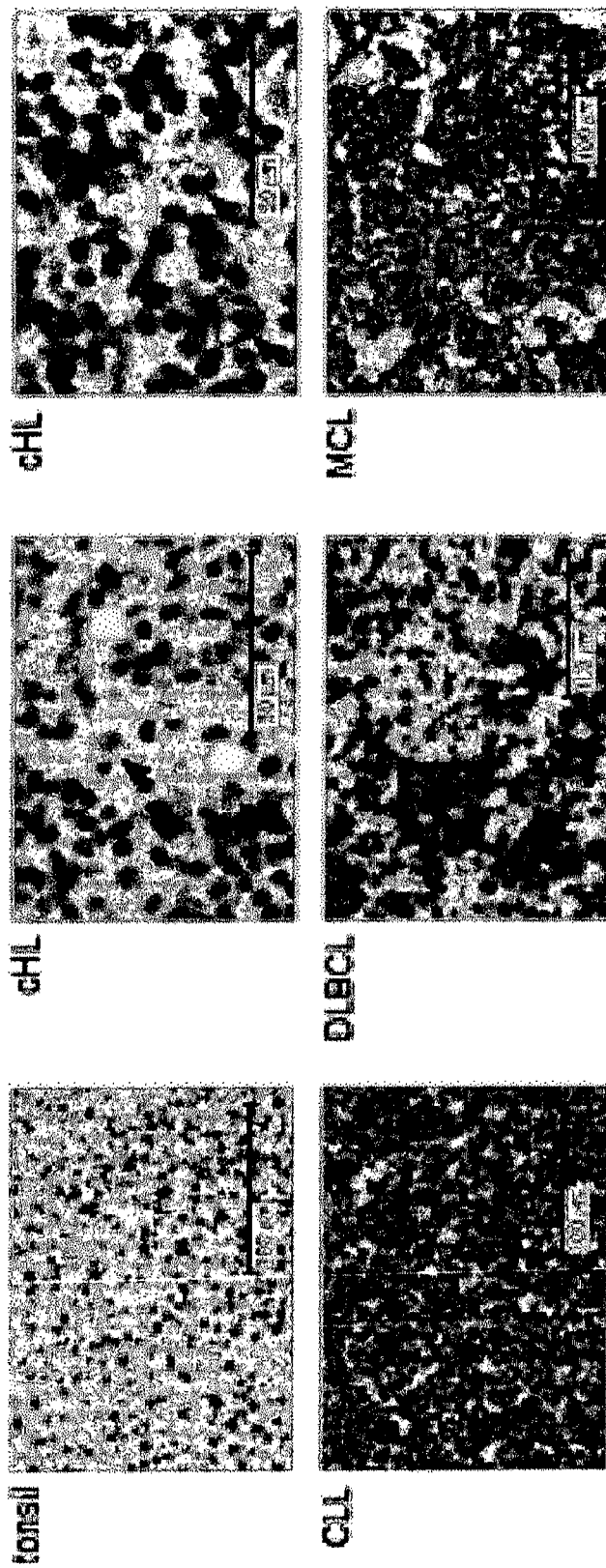
Figure 7D:
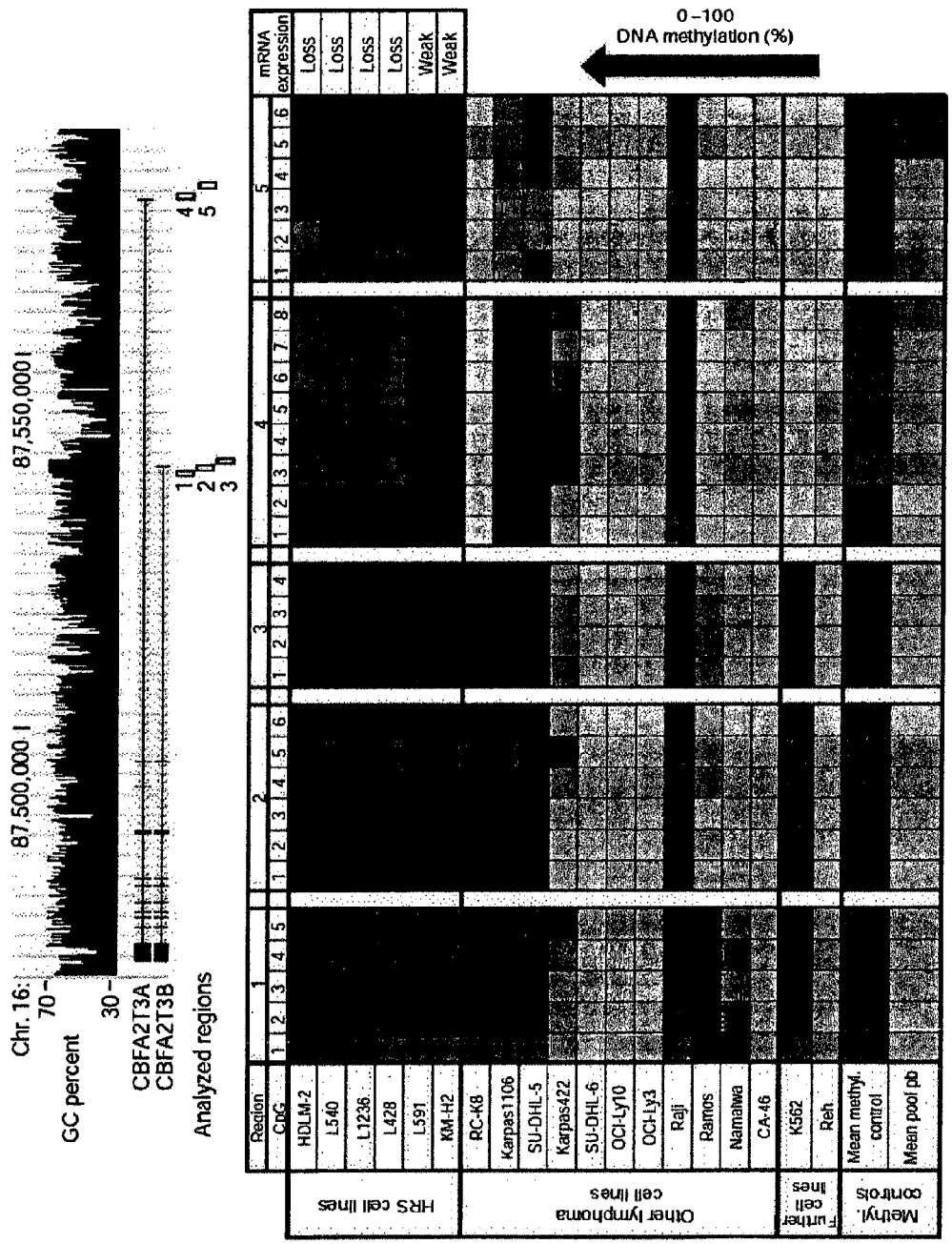

Assuming a disturbed epigenetic control in HRS cells, we screened using a candidate approach for modifiers known to be involved in epigenetic gene silencing and showing an altered expression in HRS compared to non-HRS cells. We identified a HRS cell-specific deregulated expression of the MTG/ETO-family member CBFA2T3 (also called MTG16 or ETO2), which acts as a transcriptional repressor via interaction with HDACs and co-repressors such as N-CoR and Sin3 (Hug and Lazar, 2004). Most HRS cell lines lacked CBFA2T3 mRNA and protein expression, with the exception of weak expression in KM-H2 and L591 cells (FIG. 7B). This was in contrast to the other B cell-derived cell types which all expressed CBFA2T3 mRNA (FIG. 7B, upper panel) and both CBFA2T3a and/or CBFA2T3b protein isoforms (FIG. 7B, lower panel). These results were verified in patient material of various lymphomas by CBFA2T3 immunohistochemistry (FIG. 7C and Table 2). Overall, CBFA2T3 expression was absent (or detectable only in single cells) in HRS cells of the vast majority of HL cases (91.4%; 32 of 35 cases; Table 2) whereas it was expressed in the vast majority of B cell non-Hodgkin lymphomas (85.5%; 53 of 62 cases; Table 2). To investigate whether chromosomal deletions in 16q24.3 containing the CBFA2T3 locus were associated with the lack of its expression we performed combined immunofluorescence for CD30, which is a marker for HRS cells, and interphase cytogenetic analyses (FICTION) on 17 HL patient cases (data not shown). The number of 16q24.3 was lower than that of centromere 16 in 6 HL cases (35%) indicating deletion in 16q24.3. Additionally, 3 HL cases showed a signal pattern indicating loss of whole chromosome 16. No homozygous deletions were observed. In addition, we investigated epigenetic silencing of the CBFA2T3 gene by DNA methylation in six HRS cell lines by bisulfite-pyrosequencing of CpGs around the TSSs of both variants CBFA2T3a and CBFA2T3b (FIG. 7D). The DNA was strongly methylated at most investigated CpGs in all five studied regions in the four HRS cell lines with complete lack of CBFA2T3 expression (L428, L1236, HDLM-2, L540), and in particular in regions 1 to 3 in cell lines KM-H2 and L591 with weak CBFA2T3 expression. The same regions were unmethylated in DNA from peripheral blood used as control. Other lymphoma and leukemia cell lines displayed a heterogeneous pattern with most of them retaining at least the region around the CBFA2T3a TSS unmethylated (FIG. 7D).

To investigate a mechanistic link between loss of CBFA2T3 and LTR de-repression, we transfected the non-Hodgkin cell line Reh with a shRNA construct targeting both CBFA2T3 isoforms (FIG. 8). Since constitutive NF-κB activity is one of the central molecular features of HRS cells (Hinz et al., 2002; Küppers, 2009) and this activity contributes to the LTR activation in HRS cell lines (FIG. 6D), we also transfected a constitutively activated form of the IκB kinase β (IKKβ(EE)) (Delhase et al., 1999). The simultaneous downregulation of CBFA2T3 and activation of NF-κB in Reh cells led to a strong synergistic activation of the LTR and expression of the non-canonical CSF1R transcripts (FIG. 8).

Expression of a Novel mRNA Transcript According to the Invention in ALCL and Mamma Carcinoma.

Apart from Hodgkin lymphoma, an aberrant expression of CSF1R has been described in anaplastic large cell lymphoma (ALCL) (Mathas, S., Kreher, S., Meaburn, K. J., Jöhrens, K., Lamprecht, B., Assaf, C., Sterry, W., Kadin, M. E., Daibata, M., Joos, S., et al. (2009). Gene deregulation and spatial genome reorganization near breakpoints prior to formation of translocations in anaplastic large cell lymphoma. PNAS 106, 5831-58369) and mamma carcinoma (Lin, E. Y., Nguyen, A., Russell, R. G., Pollard, J. W. (2001). Colony-stimulating factor 1 promotes progression of mammary tumors to malignancy. J. Exp. Med. 193, 727-740).

The inventors were able to show that all investigated ALCL cell lines expressing CSF1R expressed the newly identified LTR-driven CSF1R transcripts (7 of 7 cell lines; analyzed with the −5090/+131 primer pair). In addition, 35 primary tissue samples of patients suffering from mammary tumors were investigated. In 9 of 35 samples, the newly identified aberrant CSF1R transcripts according to the invention were detected (analyzed with the −5090/+131 primer pair).

Furthermore, the mRNA of 35 breast cancer specimens was screened for the presence of LTR driven CSF1R transcripts. To this end, total RNA was extracted from frozen sections and expression of canonical and non-canonical CSF1R transcripts was analyzed by RT-PCR. In 6 of the 35 samples, an amplification of LTR-CSF1R transcripts was detectable.

Discussion

In this study we addressed the questions of whether up-regulation of lineage-inappropriate genes is linked to the malignant transformation of lymphoid cells and by which molecular mechanism non-B lineage genes are activated. Based on the facts (i) that HRS cells do not express a functional BCR (Küppers, 2009), (ii) that they concomitantly up-regulate non-B lineage genes (Küppers, 2009; Küppers et al., 2003; Mathas et al., 2006) and (iii) that they usually do not home in the germinal center which is their supposed environment of origin (Höpken et al., 2002), we have postulated that the lineage-infidelity of HRS cells is required to ensure their survival (Janz et al., 2006).

Here we provide evidence that expression of non-B lineage genes, exemplarily shown for the CSF-1:CSF1R signaling pathway, are required for FIRS cell survival. Although the precise signaling pathways affected by CSF1R activation in HRS cells have to be investigated in future studies, the facts that (i) CSF1R is constitutively activated in most HL cell lines, (ii) all primary HL cases express CSF1R and CSF-1, and (iii) cell lines with CSF1R activation are sensitive to its inhibition point to CSF1R inhibition as a new therapeutic strategy for HL.

The loss of the B cell-specific gene expression pattern and the concomitant up-regulation of CSF1R and other non-B lineage genes in HRS cells is reminiscent of the reprogramming of the B cell-specific gene expression by deletion of the transcription factor genes Pax5 and E2A in mice (Ikawa et al., 2004; Nutt and Kee, 2007). However, our data show that the molecular mechanism of reprogramming in human HRS cells fundamentally differs from that observed in these mouse models. In mice, PAX5 represses the Csf1r promoter by directly interacting with a binding site next to the TSS (Tagoh et al., 2006). In contrast, in HRS cells CSF1R is not expressed from its regular promoter, but transcription initiates at a LTR element located more than 6 kB upstream of the normal promoter.

It has long been speculated that the aberrant activation of repeat elements could contribute to development of human diseases (Druker and Whitelaw, 2004; Jern and Coffin, 2008). LTRs in the human genome, of which more than 100,000 copies are MaLR like sequences (Smit, 1993), originate from ancient retroviral infections and contain promoter and enhancer elements required to express retroviral genes (Jern and Coffin, 2008). Since the insertion of an active LTR can interfere with gene regulation, the mammalian organism has devised a number of surveillance mechanisms to silence these elements, both in terms of gene activity and mobilization (Jern and Coffin, 2008; Maksakova et al., 2008). In spite of this, genome wide analysis of the human transcriptome revealed that an unexpectedly high proportion of transcripts initiates within repetitive elements (Faulkner et al., 2009).

However, for only a few human genes the initiation of transcription from repeat elements has been documented in detail, where LTRs function as alternative promoters regulating e.g. cell type-specific gene expression (Jern and Coffin, 2008). Moreover, the pathogenetic relevance of previously described repeat activation in human malignancies is unclear (Ehrlich, 2002; Jern and Coffin, 2008). We have extended these findings here by demonstrating that LTR-driven transcription results in the aberrant and pathogenetically important up-regulation of a gene with transforming capacity (Roussel et al., 1987) in human transformed cells.

When searching for epigenetic regulatory factors differentially expressed in HRS cells, we identified a HRS cell-specific lack of the MTG/ETO-family member CBFA2T3, which normally is ubiquitously expressed including all human B cell subsets (Gamou et al., 1998; Küppers et al., 2003). Our data are in accordance with microarray data showing that CBFA2T3 is among the most differentially regulated genes in HRS and non-HRS cells (Küppers et al., 2003). Loss of CBFA2T3 expression was found to be associated with aberrant DNA methylation, and 3 of 17 HL cases (18%) showed losses of chromosome 16 as compared to the ploidy. Moreover, the number of signals for 16q24 containing CBFA2T3 was lower than that for centromer 16 in 6 HL cases studied. Though this pattern formally fulfills the criteria for diagnosing a deletion of 16q24, gains of the short arm of chromosome 16 can result in a similar signal pattern and have been detected by CGH in 24% of HL cases (Joos et al., 2002). Furthermore, it needs to be considered that the frequent loss of heterozygosity in 16q24 in 4/7 HL cases described by Oshima et al. (2001) might not only be due to chromosomal deletion but also to isodisomy, which is not detectable by FISH.

MTG/ETO-family genes are key transcriptional co-repressors in various cell types, and they can recruit other co-repressors like N-CoR/SMRT, Sin3A/3B and HDAC1-3 to various transcription factors and block their transcriptional activity (Hug and Lazar, 2004). Alterations of CBFA2T3 expression in human breast cancer suggest a function as tumor suppressor (Kochetkova et al., 2002). It is intriguing to speculate that the lack of such an epigenetic regulatory factor appears to be central to FIRS cell biology, since these cells employ different mechanisms to render CBFA2T3 inactive. This is in agreement with recently published data showing the induction of a Hodgkin-like phenotype in B cells following combined histone acetylation and DNA demethylation (Ehlers et al., 2008). Interestingly, following Cbfa2t3 deletion in mice the number of B cells is reduced and early progenitor cells are shifted towards the granulocytic-macrophage lineage (Chyla et al., 2008). Furthermore, Cbfa2t3 deletion results in the up-regulation of genes involved in several signaling pathways, including C/EBP proteins, Stat and Notch members, Id2, and Csf1r (Chyla et al., 2008), all known to have important biological functions in the malignant HRS cells (Kuppers, 2009). This phenotype of Cbfa2t3-deficient mice supports our interpretation that loss of CBFA2T3 expression is intimately linked to HL pathogenesis. Since ETO-family proteins can furthermore modulate the activity of bHLH transcription factors (Kumar et al., 2008), the loss of CBFA2T3 might enhance the functional block of the bHLH factor E2A in FIRS cells (Mathas et al., 2006). However, loss of CBFA2T3 per se is not sufficient for CSF1R activation. Transcription factors with a known altered activity in HRS cells contribute to the aberrant activation of the CSF1R-LTR. Specifically, our data link the deregulated IKK/NF-κB activity, which is also involved in MaLR element regulation in the rat CYP2B1 promoter (Lee et al., 2000), in HRS cells to their reprogramming. Taken together, these data suggest that the activity of non-B lineage genes contributes to the replacement of the B cell-specific regulatory circuitry in HRS cells, and they strongly support the hypothesis that lineage-infidelity of lymphoid cells is linked to their malignant transformation.

On a more speculative note, the data opens a new view on the unique and unusual genomic instability of HRS cells. Chromosomes of FIRS cells are often composed of multiple chromosome fragments of different origin and show an ongoing rearrangement activity and segmental chromosomal aberrations (Joos et al., 2002; MacLeod et al., 2000). In mice, genomic hypomethylation due to lymphoid-specific helicase (Lsh) deletion or generation of a hypomorphic DNA methyltransferase 1 (Dnmt1) allele results in reactivation of repetitive elements concomitant with chromosomal instability (Eden et al., 2003; Huang et al., 2004).

Furthermore, in hypomethylation-induced erythroleukemias originating from Lsh$^{-/-}$ hematopoietic progenitors and T cell lymphomas of Dnmt1-hypomorphic mice a direct link between leukemo/lymphomagenesis and activation and transposition of endogenous retroviral elements has been proven (Fan et al., 2008; Howard et al., 2008). Thus, the data regarding the activation of repetitive elements with their intrinsic capability to recombine offers an attractive explanation for the unusual genomic instability of HRS cells.

THE1 LTR Activation is a Widespread Phenomenon in HRS Cells

The inventors addressed the question whether THE1 subfamily LTR activation in HRS cells is restricted to CSF1R or whether LTR derepression is a more general phenomenon. To this end, the inventors screened mRNAs of the various Hodgkin's and non-Hodgkin's cell lines for additional THE1 family LTR-driven transcripts. The inventors used a 3' RACE approach for the identification of LTR-driven full-length transcripts (FIG. 14 and FIG. 18*c*) and a terminal transferase-dependent PCR (TD-PCR) approach for the identification of the 5' ends of putative LTR-driven mRNAs (FIG. 15 and FIG. 18*c*). Both analyses showed prominent amplification products in most HRS cell lines as compared to non-Hodgkin's cell lines or primary B and T cells, in which we observed only weak or no amplification (FIG. 14, 15). The fact that products of multiple sizes were generated in HRS cells by both approaches shows that THE1 LTR-driven transcripts originated from multiple LTRs of this family. The inventors confirmed this supposition by cloning and sequencing of several PCR products and determining their genomic alignment (Tables 4 and 5, FIGS. 17 and 24). From these data, the inventors conclude that THE1 subfamily LTR activation in HRS cells is not restricted to CSF1R but occurs at many independent genomic sites and includes at least THE1A, THE1B and THE1C.

Detection of LTR-Driven CSF1R Transcripts in ALCL

To evaluate whether LTR-CSF1R transcripts are restricted to Hodgkin's lymphoma or are also present in other human malignancies, the inventors analyzed 30 primary lymphoma samples of various subtypes for expression of canonical and LTR-driven noncanonical CSF1R transcripts (FIG. 16). The inventors detected canonical CSF1R transcripts in all samples; these were most likely produced by normal myeloid cells present in these samples. In contrast, LTR-CSF1R transcripts were present in only four of the five ALCL samples, in which the inventors recently described an aberrant CSF1R expression[29] and in which CSF1R activation contributes to cell survival (FIG. 25), whereas LTR-CSF1R transcripts were not detectable in any of the other non-Hodgkin's lymphoma samples analyzed (FIG. 16).

Experimental Procedures
Cell Lines, Culture Conditions, and Transfections.

HRS (L428, L1236, KM-H2, L591 [EBV+], HDLM-2, L540, and L540Cy), pro-B lymphoblastic leukemia (Reh), Burkitt's lymphoma (Namalwa, BL-60, BJAB), diffuse large B-cell lymphoma (DLBCL; SU-DHL-4), multiple myeloma (MM1.S) and acute myeloid leukemia (AML; HL-60) cell lines were cultured as described (Mathas et al., 2002; Mathas et al., 2006). Where indicated, cells were maintained in fetal calf serum (FCS)-reduced medium. Cells were treated with 100-200 ng/ml recombinant human (rh)CSF-1 (216-MC), 80 µg/ml rhCSF1R:Fc chimera (CSF-1R:Fc; 329-MR) or control IgG1:Fc (110-HG; all from R&D Systems), the indicated amounts of CYC10268 (Irvine et al., 2006), CYC12200 (compound 12 in Burns et al., 2009), and CYC12752 (all prepared as in Burns et al., 2009) (Cytopia patent application WO2008058341) or DMSO control, 3 mmol/l 5-aza-dC for 72 h, 625 nmol/l TSA (both from Sigma-Aldrich) for 24 h. Cells were electroporated (EP) in OPTI-MEM I using a Gene-Pulser II (Bio-Rad) with 950 µF and 0.18 kV (L428, L540Cy), 50 µF and 0.5 kV (KM-H2), 500 µF and 0.3 kV (Reh, L591). Transfection efficiency was determined by pEGFP-N3 (Clontech Laboratories) co-transfection and FACS analysis. L428 and KMH2 cells were transfected with 20 µg pcDNA3-IκBαΔN or control plasmid along with 10 µg pEGFP-N3. After 48 h, CSF-1 protein expression in GFP+ cells was analyzed by intracellular FACS analysis. Reh cells were transfected with 30 µg of a pMSCVpuroH1-shCBFA2T3 and/or 30 µg of a pRK5-IKKβ(EE) expression plasmid or controls along with 10 µg pEGFP-N3. 48 h after transfection, GFP+ cells were enriched by FACS sorting. For analysis of luciferase activity, L428, KM-H2, L540Cy, and L591 cells were transfected by EP with 10-14 µg of reporter constructs, together with 200-400 ng pRL-TKLuc as an internal control. 24-48 h after transfection, the ratio of the two luciferases was determined (Dual luciferase kit; Promega). Primary CD33+ myeloid cells were purified from peripheral blood of healthy donors using the Monocyte Isolation Kit II (130-091-153), primary CD19+ B cells from human tonsils with CD19 MicroBeads (130-050-301; both Miltenyi Biotec). Purity of CD33+ and CD19+ B cells was greater than 83% and 97%, respectively. The use of human material was approved by the local ethics committee of the Charité (Berlin, Germany), and performed in accordance with the Declaration of Helsinki.

DNA constructs.

The pcDNA3-IκBαΔN expression construct was described (Mathas et al., 2002). Vectors for expression of shRNAs were generated from pMSCVpuro-H1 (pMSCVpuro obtained from Clontech) cloning target sequences CBFA2T3 5'-GAAGTGATCGACCACAAGC (SEQ ID NO. 12) (provided by N. Goardon (Goardon et al., 2006)) or control sequence (scrambled) 5'-GACACGCGACTTGTACCA (SEQ ID NO. 13) downstream of the H1 promoter. For the IKKβ(EE) construct, full-length human IKKβ cDNA was cloned with N-terminal FLAG epitope into pRK5 and activating mutations S177E and S181E were introduced (Delhase et al., 1999). For generation of CSF1R-LTR reporter constructs, fragments of positions −382/+14, −142/+14 and −85/+14 (positions relative to the HL-specific TSS) were amplified from the genomic clone RZPDB737C051001D (imaGenes) and cloned into pGL2-Basic (Promega). pGL2-Promoter (Promega) served as positive control. Where indicated, the binding site for SP1 was mutated from 5'-GGGTGGGG to 5'-GTTTGGGG, for GATA from 5'-AGATAA to 5'-ACTTAA, for AP-1 from 5'-TGAATCA to 5'-TGAATTG, for NF-κB from 5% GGGAGTTCCCC (SEQ ID NO. 14) to 5'-GGCCTTTAACC (SEQ ID NO. 15) by use of the QuickChange Multi Site-Directed Mutagenesis Kit (Stratagene). All constructs were verified by sequencing.

RNA Preparation, Northern Blot and PCR Analyses.

RNA preparation and Northern blot (NB) analyses were performed as described (Mathas et al., 2002; Mathas et al., 2006). For NB analyses, membranes were hybridized with [α-$^{32}$P]dCTP-labeled random prime-labeled DNA probes specific for CSF1 and GAPDH. For RT-PCR analyses, cDNA-synthesis was performed with the 1st strand cDNA synthesis Kit (AMV; Roche). qRT-PCR analyses were performed as described (Walter et al., 2008). TSSs were determined with 10 µg of total RNA by 5'-RLM-RACE using the FirstChoice® RLM-RACE Kit (Ambion). Gene-specific primers were used to amplify endogenous CSF1R (5'-RACE outer primer: CSF1R-32 as; 5'-RACE inner primer: CSF1R-97 as). PCR products were gel purified and cloned into pCR®2.1 vector (TA Cloning® Kit, Invitrogen). Inserts from 10 individual plasmid-containing bacterial colonies derived from each RLM-RACE were sequenced. All primers used are listed in Table 3.1.

In Vivo DNase I Footprinting, Linker-Mediated PCR (LM-PCR), DNase I Hypersensitive Site (DHS) Mapping.

In vivo DNase I footprinting and LM-PCR were performed as described (Walter et al., 2008), primers are listed in Table 3.3. For DHS mapping, 15 µg of in vivo DNase I treated DNA was digested with KpnI to completion and subjected to Southern blot analysis. The hybridization probe was generated by PCR using CSF1R-5747 s (5'-GCGTGCTCAATAGTT-TATGT) (SEQ ID NO. 16) and CSF1R-5084 as (5'-TTAAGT-CAATGAAGCCAGTA) (SEQ ID NO. 17) as primers.

Immunoprecipitation (IP) and Chromatin Immunoprecipitation (ChIP).

CSF1R IP was essentially performed as described (Downing et al., 1991) (for detailed protocol see Supplemental Information) using anti-CSFR antibody (MAB3291) or the respective isotype control (MAB002; both R&D Systems). Western blot (WB) analyses were performed with an anti-p-Tyr antibody (sc-7020; Santa Cruz) and membranes were reprobed with anti-CSF1R (sc-692; SantaCruz). ChIP assays included RNA polymerase II (sc-900X, Santa Cruz) and H3K4me3 (ab4441, Abcam) (for detailed protocol see Supplemental Information). The eluted DNA was analyzed by qRT-PCR or semi-quantitative PCR. Primers are listed in Table 3.1.

Electrophoretic Mobility Shift Assay (EMSA) and Western Blotting.

Whole-cell extract preparation, EMSA and WB were performed as described (Mathas et al., 2002). For WB, the following primary antibodies were used: anti-kκBα (sc-371; SantaCruz), anti-CBFA2T3 (Kumar et al., 2008), anti-FLAG M2 (F1804), anti-β-actin (both from Sigma-Aldrich). Filters were incubated with HRP-conjugated secondary antibodies. Bands were visualized using the enhanced ECL system (Amersham Pharmacia Biotech).

Immunofluorescence and Flow Cytometry.

For the analysis of CSF1R expression, cells were stained with an anti-CSF1R antibody (MAB3291) or control (MAB002; both R&D Systems), expression of intracellular CSF-1 was analyzed by use of the Fix&Perm kit (GAS-004; Caltag Laboratories) and staining with anti-CSF-1 antibody (MAB216) or control (MAB003; both R&D Systems). Following incubation with a PE-conjugated F(ab')$_2$ fragment goat anti-mouse IgG (115-116-071; Dianova) immunofluorescence was analyzed.

Measurement of the Secreted Amount of CSF-1 by ELISA.

ELISA was performed with supernatants of various cell lines by use of the CSF-1 DuoSet ELISA Development kit (DY216; R&D Systems). Cells were plated at 0.8×10⁶/ml, and supernatants were collected after 48 hours.

Proliferation Assays and Analysis of Apoptosis.

DNA synthesis was determined by [$^3$H]-thymidine incorporation assays using standard protocols. The percentage of viable and apoptotic cells was determined by annexin V-FITC/propidium iodide (PI) double-staining (Bender Med-Systems) and subsequent FACS analysis.

Interphase Cytogenetics.

Combined immunofluorescence and interphase fluorescence in situ hybridization (FISH) was performed as described (Martin-Subero et al., 2002) using BAC clone CTD-3010L24 (labeled in Spectrum Orange) hybridizing in chromosome 16q24.3 (chr16:87,193,946-87,438,619 bp) immediately (~30 kb) centromeric of the CBFA2T3 gene (chr16:87,468,768-87,570,902). Commercial probes for the centromeric regions of chromosomes 6 (CEP6, Spectrum Aqua), 10 (CEP10, Spectrum Aqua), 16 (CEP16, Spectrum Aqua) and 17 (CEP17, Spectrum Green) served for determining copy number of chromosome 16 and estimating ploidy of HRS cells. For FICTION, immunofluorescence with anti-CD30 antibody detected with an Alexa-594 conjugated secondary antibody (Molecular probes) was applied. The median number of HRS cells evaluated for 16q24.3 and CEP16 per case was 26 (10-36). Nuclei of bystander cells served as internal controls. A deletion of 16q24.3 was defined as lower number of 16q24.3 signals as compared to CEP16 signals in at least 30% of HRS cells.

Bisulfite Pyrosequencing.

Bisulfite pyrosequencing of 5 amplicons covering the regions of TSSs of CBFA2T3 isoforms (isoform A: NM_005187.4; isoform B: NM_175931) was performed according to standard protocols (for detailed protocol see Supplemental Information). PCR and sequencing primer sequences are shown in Table 3.2. All assays were optimized and validated using completely methylated DNA (Millipore) and pooled DNA isolated from peripheral blood of 10 healthy male and female controls, respectively.

Immunohistochemistry (IHC) and RNA In Situ Hybridization (ISH).

For IHC, the dewaxed 4 µm sections were subjected to an antigen-demasking procedure of brief, high-temperature heating of the sections immersed in citrate buffer (10 mmol/l, pH 6.0) and heating for 2 min in a high-pressure cooker. CBFA2T3 antibody (Kumar et al., 2008) was applied at a dilution of 1:500. Bound antibody was visualized using the alkaline phosphatase anti-alkaline phosphatase method and fastRed as chromogen (DAKO). For RNA ISH, paraffin embedded tissue specimens were dewaxed and treated with proteinase K (DAKO; 1:10 dilution). Hybridization with biotin-labeled CSF1R probes (fragment +720/+1304; sense (negative control) and anti-sense orientation) was performed over night at 50° C. in a DAKO hybridizer. The hybridized sections were washed under stringent conditions in order to get rid of unspecifically bound probes. Detection of specifically bound probe was carried out after blocking of endogenous biotin with a streptavidin-AP conjugate employing NBT/BCIP (DAKO) as a substrate.

TABLE 1

Table 1. Induction of apoptosis in HRS (KM-H2, HDLM-2, L540) but not non-Hodgkin (Reh, Namalwa) cell lines following pharmacological CSF1R inhibition.

| Compound | KM-H2 | HDLM-2 | L540 | Reh | Namalwa | time |
|---|---|---|---|---|---|---|
| CYC10268 1.0 µM | +++ | + | ++ | 0 | 0 | 72 h |
| CYC10268 2.0 µM | +++ | ++ | ++++ | 0 | 0 | 7 d |
| CYC12200 5 µM | + | + | 0 | 0 | 0 | 7 d |
| CYC12200 10 µM | ++ | +++ | + | 0 | 0 | 7 d |
| CYC12752 10 µM | + | + | ++ | 0 | 0 | 7 d |
| CYC12752 15 µM | ++ | +++ | +++ | 0 | 0 | 7 d |

0 unaltered viability
+ 5-20% apoptotic cells
++ 20-40% apoptotic cells
+++ 40-70% apoptotic cells
++++ 70-100% apotopic cells The various cell lines were treated with the indicated amounts of the CSF1R inhibiting compounds CYC10268, CYC12200, and CYC12752, as indicated. At the indicated times, the amount of apoptotic cells was determined by annexin V-FITC/propidium iodide (PI) double-staining and subsequent flow cytometry.

TABLE 2

Table 2. Summary of CBFA2T3 immunohistochemistry.

| Entity | Number of cases analyzed | all neoplastic cells negative | single positive cells | <50% of neoplastic cells positive | >50% of neoplastic cells positive |
|---|---|---|---|---|---|
| CLL | 7 | 0 | 0 | 5 | 2 |
| Mantle cell lymphoma | 9 | 0 | 1 | 0 | 8 |
| Follicular lymphoma grade 1-2 | 13 | 0 | 1 | 12 | 0 |
| Follicular lymphoma grade 3a and 3b | 11 | 4 | 0 | 5 | 2 |
| Diffuse large B cell lymphoma | 15 | 3 | 0 | 4 | 8 |
| Burkitt lymphoma | 7 | 0 | 0 | 2 | 5 |
| Classical Hodgkin lymphoma | 35 | 28 | 4 | 0 | 3 |

Expression of CBFA2T3 was analyzed in various human lymphoma entities, as indicated.

TABLE 3

Table 3.1 Primers used for semiquantitative RT-PCR and RealTime PCR analyses were:

| name | 5'- Sequence -3' | product length |
|---|---|---|
| CSF1R-*805*s | TGACCCCAGATGTAGAGGAT (SEQ ID NO. 18) | 74 bp |
| CSF1R-*731*as | GGCACCAGATTCGTGTCT (SEQ ID NO. 19) | |
| CSF1R-*595*s | CTGGGCAACAGAGTGAAACTG (SEQ ID NO. 20) | 113 bp |
| CSF1R-*504*as | CCCTGATGTCCTGGCTTACAA (SEQ ID NO. 21) | |

TABLE 3-continued

Table 3.1 Primers used for semiquantitative
RT-PCR and RealTime PCR analyses were:

| name | 5'- Sequence -3' | product length |
|---|---|---|
| CSF1R-169s | AGAAGAGGATCAGCCCAAGGA (SEQ ID NO. 22) | 91 bp |
| CSF1R-97as | AGGGATCGGGACACTGGAC (SEQ ID NO. 23) | |
| CSF1R-100s | TGTGTCCAGTGTCCCGATCC (SEQ ID NO. 24) | 87 bp |
| CSF1R-32as | AAGTGGCAGGCAGGTGCAG (SEQ ID NO. 25) | |
| CSF1R + 1s | ATGGGCCCAGGAGTTCTG (SEQ ID NO. 26) | 95 bp |
| CSF1R +76as | TCCATCACACCCCAACAAAG (SEQ ID NO. 27) | |
| CSF1R + 59s | CCCAGTGATAGAGCCCAGTGT (SEQ ID NO. 28) | 90 bp |
| CSF1R + 131as | CATTCCACGCTGCCATTG (SEQ ID NO. 29) | |
| CSF1R-5747s | GCGTGCTCAATAGTTTATGT (SEQ ID NO. 16) | 663 bp |
| CSF1R-5084as | TTAAGTCAATGAAGCCAGTA (SEQ ID NO. 17) | |
| CSF1R-5090s | TTTTGCTACTGGCTTCATTGA (SEQ ID NO. 30) | 389 bp |
| CSF1R + 131as | CATTCCACGCTGCCATTG (SEQ ID NO. 29) | |
| CSF1R-6152s | GCCTTCCACTATGATTCTGA (SEQ ID NO. 31) | 185 bp |
| CSF1R-161as | CCTCCTCCTTGGGCTGAT (SEQ ID NO. 32) | |
| CSF1R + 720s | AACACTAAGCTCGCAATCC (SEQ ID NO. 33) | 605 bp |
| CSF1R + 1304as | TCACACCTATCAGTGTGGCC (SEQ ID NO. 34) | |
| CSF1s | TGCTGTTGTTGGTCTGTCTCC (SEQ ID NO. 35) | 467 bp |
| CSF1as | AGCTGTTGTTGCAGTTCTTGC (SEQ ID NO. 36) | |
| GAPDHs | ATGCTGGCGCTGAGTAC (SEQ ID NO. 37) | 257 bp |
| GAPDHas | TGAGTCCTTCCACGATAC (SEQ ID NO. 38) | |
| TBPs | CAGGAGCCAAGAGTGAAGAACA (SEQ ID NO. 39) | 79 bp |
| TBPas | AGCTGGAAAACCCAACTTCTGT (SEQ ID NO. 40) | |
| CBFA2T3s | CGAGCACCTCAGCAAACG (SEQ ID NO. 41) | 410 bp |
| CBFA2T3as | GGGCCCTTCTTTGTGTCCTC (SEQ ID NO. 42) | |

Regarding CSF1R, primers are numbered relativ to the translational start (+1).
'Bold/italic' indicates relative position in the genomic sequence, '*italic*' relative position in the cDNA sequence (NM_005211).

TABLE 3.2.

Primers used for Bisulfite Pyrosequencing were:

| Name | 5'- sequence -3' | 5'-end modification | product length |
|---|---|---|---|
| R1-2_F | GTGAGTTTTTGTGGAGGGATAGATGGTTGGA (SEQ ID NO 43) | Biotin | |
| R1-2_R | CCCCACCCTAACTAAAACCACAAACCTAACAACTACC (SEQ ID NO 44) | | 349 bp |
| R1-2_seq1 | CCCACAAAATAAATAAAAAATA (SEQ ID NO 45) | | |
| R1-2_seq2 | CCCCCCACCAACCTA (SEQ ID NO 46) | | |
| R3_F | TTTGTAGGTAGTTGTTAGGTTTGTGGTTTTAGTTAGGGTG (SEQ ID NO 47) | | |
| R3_R | CAAACCCAACCCTCCCCCCTTCAAATCT | Biotin | 264 bp |

TABLE 3.2.-continued

Primers used for Bisulfite Pyrosequencing were:

| Name | 5'- sequence -3' | 5'-end modification | product length |
|---|---|---|---|
| | (SEQ ID NO 48) | | |
| R3_seq | TAGGAGGTTTTTAGGGTAG (SEQ ID NO 49) | | |
| R4_F | TGGGAGGAGGAAGTTGTTGGAAGGTTAAA (SEQ ID NO 50) | Biotin | |
| R4_R | CCTAAAAAACCCAAACCCTCCCCACCACCAACTAAATAT (SEQ ID NO 51) | | 289 bp |
| R4_seq | AAAAAAATCTCCCTACAACCT (SEQ ID NO 52) | | |
| R5_F | AGGTGGTGGGGTGGGGGTAGAGA (SEQ ID NO 53) | | |
| R5_R | CTCACCAACCCACCTACCCCAACT (SEQ ID NO 54) | Biotin | 183 bp |
| R5-seq | GGGTGGGGGTAGAGA (SEQ ID NO 55) | | |

TABLE 3.3.

Primers used for LM-PCR were:

| | | |
|---|---|---|
| CSF1R promoter | 1st | CTACTAGCTCCGCAGGGATCG (SEQ ID NO 56) |
| | 2nd | ACACGTTCCTCTCCTCTGCACTG (SEQ ID NO 57) |
| | 3rd | CTCTCCTCTGCACTGGCTGTTTGTCTTG (SEQ ID NO 58) |
| TBP promoter | 1st | ATCTGTTACCTGGGTCACT (SEQ ID NO 59) |
| | 2nd | AGATCACTATGGGCCAGCGGAAG (SEQ ID NO 60) |
| | 3rd | ATGGGCCAGCGGAAGCGAAGTTAAACAG (SEQ ID NO 61) |

TABLE 4

| Clone | Cells | LTR | Strand | Start site | 5'-end of RNA |
|---|---|---|---|---|---|
| Table 4.1 Single clones from nested PCR of LTR 5'RACE using reverse consensus THE1B primer_2 | | | | | |
| Consensus | | THE1B | | | GCTCTCTTGCCTGCCGCCATGTAAGACGT . . . (SEQ ID NO 62) |
| CSF1R | | THE1B | − | chr5: 149, 472, 187 | GCTCTCTTGCCTGCCGCCATGTAAGACGT . . . (SEQ ID NO 62) |
| 703 * | L428 | THE1B | + | chr14: 97, 903, 794 | TTTCTTTGCCTGCTGTCATTCATGTAAGA . . . (SEQ ID NO 63) |
| 709 * | KM-H2 | THE1B | − | chr14: 89, 744, 579 | ATTCTCCCTTGTCTGTCGCCATGTAAGAC . . . (SEQ ID NO 64) |
| 712 | KM-H2 | THE1B | − | chr22: 40, 270, 068 | TTTCTTTGCCTGCCACCATCCACATAAGA . . . (SEQ ID NO 65) |
| 713 | KM-H2 | THE1A | − | chr2: 60, 343, 785 | CTCATTTTCTCTTGCCACAGCCATGAAAG . . . (SEQ ID NO 66) |
| 715 | KM-H2 | THE1B | + | chr5: 151, 338, 423 | AAGGGGGAGTTTTCCTGCACAAGATCTCT . . . (SEQ ID NO 67) |
| 716 | KM-H2 | THE1B | + | chr14: 94, 886, 434 | GCTTGCCACCATGTAAGATGTGACTTTGC . . . (SEQ ID NO 75) |
| Table 4.2 Single clones from nested PCR of LTR 5'RACE using reverse CSF1R-LTR primer_2 | | | | | |
| 702 * | L428 | THE1A | − | chr12: 68, 835, 919 | TCTCTTGCTGCCGCCGTGTAAGAAGGACC . . . (SEQ ID NO 68) |

TABLE 4-continued

| Clone | Cells | LTR | Strand | Start site | 5'-end of RNA |
|---|---|---|---|---|---|
| 707 | KM-H2 | THE1B | + | chr2: 12, 007, 319 | TCTCTTAACTGCTGCCATGTAAGACACGC . . . (SEQ ID NO 69) |
| 718 | L1236 | THE1B | + | chr14: 97, 903, 794 | TTTCTTTGCCTGCTGTCATTCATGTAAGA . . . (SEQ ID NO 63) |

Table 4 Identification of transcription initiation sites within newly identified transcribed MaLR THE1-family LTRs. To enable amplification of LTRs matching either the THE1B consensus or the CSF1R sequence, cDNA was synthesised from L428, KM-H2 and L1236 HRS cell RNA using a mixture of both reverse THE1B primer_1 and reverse CSF1R primer_1, as depicted in Supplementary FIG. 5c. cDNA TD-PCR products of ~80-110 bp having the correct size for initiation within THE1-family LTRs were purified for subsequent nested PCR using the reverse THE1B primer_2 in combination with the LP25 primer (see also FIG. 5d and Supplementary FIG. 5c). Shown above are representative clones of mRNA 5'-ends amplified with either the THE1B or the CSF1R primer. Asterisks denote transcribed LTRs that were detected more than once by either 5' or 3'RACE. Each transcribed LTR has an ideal consensus splice site (GTGAGT or GTAAGT) within the genomic sequence at the predicted splice site just downstream of the reverse primer (not shown). All genome analyses are based upon the build 37.1 hg19 2009 assembly of the human genome sequence.

TABLE 5

| Clone | Exon | chromosomal location | sequence of exon junctions with primer above |
|---|---|---|---|
| Table 5.1 3'RACE of L428 cell LTR RNA using forward consensus THE1B primer_2 | | | |
| 1 | 1 | THE1B LTR(+) 2: 192, 866, 495- 192, 866, 529 | CCATGATTGTGAGGCCTCCC (SEQ ID NO 110) CCATGATTGTGAGGCCTCCCTACCCACGTGGAACT/gtgagt (SEQ ID NO 71) |
|  | 2 | 2: 192, 897, 297- 192, 897, 364 | tacag/TTACAAGCGGTAATACAAAGAGACAGGATT . . . (SEQ ID NO 72) |
| 2 | 1 | THE1B LTR(-) 2: 155, 062, 125- 155, 062, 159 | CCATGATTGTGAGGCCTCCC (SEQ ID NO 110) CCATGATTGTGAGGCCTCCCCAGCCATATGGAAAT/gtaagt (SEQ ID NO 73) |
|  | 2 | 2: 155, 057, 018- 155, 057, 118 | tccag/ATAATGCAGCAACAAGCTGCCATCTTGAAA . . . (SEQ ID NO 74) |
| Table 5.2 3'RACE of L428 cell LTR RNA using forward CSF1R primer_2 | | | |
| 3 | 1 | THE1C (+) 7: 130, 708, 095- 130, 708, 125 | GATTCTGAGGCCTCCTCAGCCATG (SEQ ID NO 112) GTTCCTGAGGCCTCCCCAGCCATGCAGAACT/gtgagt (SEQ ID NO 76) |
|  | 2 | 7: 130, 715, 937- 130, 716, 071 | tgaag/GTCATTTCAAAGCCTTAGAAACTGGCCTCAAC . . . (SEQ ID NO 77) |
| 4* | 1 | THE1A (+) 21: 47, 013, 592- 47, 013, 622 | GATTCTGAGGCCTCCTCAGCCATG (SEQ ID NO 112) GATTCTGAGGCCTCCCCAGCCATGTGGAACT/gtaagt (SEQ ID NO 78) |
|  | 2 | 21: 47, 015, 477- 47, 015, 575 | gatag/TTTTTTCTAGCTTGTGTTGTGTTTTTAATGGG . . . (SEQ ID NO 79) |

Table 5 Identification of transcribed MaLR THE1-family LTRs linked to mature mRNAs. cDNA was synthesised from L428 cell mRNA using oligo(dT) as the reverse transcriptase primer. mRNAs with exons containing LTR sequences were identified by 3'RACE PCR using the forward THE1B primer_2 or CSF1R-LTR primer_2. Amplified DNA was purified by gel electrophoresis, cloned and sequenced. Shown above are two representative clones of mRNAs amplified with either the THE1B primer_2 or the CSF1R primer_2.
The asterisk denotes a transcribed LTR that was detected twice. Each LTR mRNA is spliced at the predicted splice site and contains an ideal consensus 5' intron splice site (gtaagt or gtgagt) just downstream of the exon containing the LTR. The chromosomal location of each LTR clone is classified according to the hg 19 sequence, the orientation (+ or - strand) and THE1 family to which it belongs. Each clone was correctly spliced and polyadenylated (Supplementary FIG. 11).

TABLE 6

Table 6a Primers used for semiquantitative RT-PCR and real time PCR analyses were:

| name | 5'- Sequence -3' | product length |
|---|---|---|
| CSF1R-*805* F | TGACCCCAGATGTAGAGGAT (SEQ ID NO 18) | 74 bp |
| CSF1R-*713* R | GGCACCAGATTCGTGTCT (SEQ ID NO 19) |  |
| CSF1R-*595* F | CTGGGCAACAGAGTGAAACTG (SEQ ID NO 20) | 113 bp |

TABLE 6-continued

Table 6a Primers used for semiquantitative RT-PCR and real time PCR analyses were:

| name | 5'- Sequence -3' | product length |
|---|---|---|
| CSF1R-*483* R | CCCTGATGTCCTGGCTTACAA (SEQ ID NO 21) | |
| CSF1R-*169* F | AGAAGAGGATCAGCCCAAGGA (SEQ ID NO 22) | 91 bp |
| CSF1R-*78* R | AGGGATCGGGACACTGGAC (SEQ ID NO 23) | |
| CSF1R-*100* F | TGTGTCCAGTGTCCCGATCC (SEQ ID NO 24) | 87 bp |
| CSF1R-*14* R | AAGTGGCAGGCAGGTGCAG (SEQ ID NO 25) | |
| CSF1R + *1* F | ATGGGCCCAGGAGTTCTG (SEQ ID NO 26) | 95 bp |
| CSF1R + *96* R | TCCATCACACCCCAACAAAG (SEQ ID NO 27) | |
| CSF1R + *59* F | CCCAGTGATAGAGCCCAGTGT (SEQ ID NO 28) | 90 bp |
| CSF1R + *148* R | CATTCCACGCTGCCATTG (SEQ ID NO 29) | |
| CSF1R-*5,747* F | GCGTGCTCAATAGTTTATGT (SEQ ID NO 16) | 663 bp |
| CSF1R-*5,065* R | TTAAGTCAATGAAGCCAGTA (SEQ ID NO 17) | |
| CSF1R-*5,090* F | TTTTGCTACTGGCTTCATTGA (SEQ ID NO 30) | 389 bp |
| CSF1R + *148* R | CATTCCACGCTGCCATTG (SEQ ID NO 29) | |
| CSF1R-*6,152* F | GCCTTCCACTATGATTCTGA (SEQ ID NO 31) | 185 bp |
| CSF1R-*143* R | CCTCCTCCTTGGGCTGAT (SEQ ID NO 32) | |
| CSF1R + *720* F | AACACTAAGCTCGCAATCC (SEQ ID NO 33) | 605 bp |
| CSF1R + *1,325* R | TCACACCTATCAGTGTGGCC (SEQ ID NO 34) | |
| CSF1 F | TGCTGTTGTTGGTCTGTCTCC (SEQ ID NO 35) | 467 bp |
| CSF1 R | AGCTGTTGTTGCAGTTCTTGC (SEQ ID NO 36) | |
| GAPDH F | ATGCTGGCGCTGAGTAC (SEQ ID NO 37) | 257 bp |
| GAPDH R | TGAGTCCTTCCACGATAC (SEQ ID NO 38) | |
| GAPDH F (real time) | CTCTGCTCCTCCTGTTCGAC (SEQ ID NO 80) | 144 bp |
| GAPDH R (real time) | TTAAAAGCAGCCCTGGTGAC (SEQ ID NO 81) | |
| TBP F (real time) | CAGGAGCCAAGAGTGAAGAACA (SEQ ID NO 39) | 79 bp |
| TBP R (real time) | AGCTGGAAAACCCAACTTCTGT (SEQ ID NO 40) | |
| CBFA2T3 F | CGAGCACCTCAGCAAACG (SEQ ID NO 41) | 410 bp |
| CBFA2T3 R | GGGCCCTTCTTTGTGTCCTC (SEQ ID NO 42) | |

Numbers of CSF1R primers are given relative to the translation initiation site (+1). Thereby, numbers of primers marked in 'bold/italic' refer to positions in the CSF1R genomic sequence, numbers of primers marked in '*italic*' refer to positions in the mature CSF1R mRNA sequence (NM_005211). F, forward; R, reverse; P, promotor.

TABLE 6b

Primers used for bisulfite pyrosequencing were:

| Name | | 5'- sequence -3' | 5'-end modification | product length | Annealing temperature (° C.) |
|---|---|---|---|---|---|
| CBFA2T3 | R1_F | TTTGTAGGTAGTTGTTAGGTTTGTGGTTTTAGTTAGGGTG (SEQ ID NO 47) | | 264 bp | 60 |
| | R1_R | CAAACCCAACCCTCCCCCCTTCAAATCT (SEQ ID NO 48) | Biotin | | |
| | R1_seq | TAGGAGGTTTTTAGGGTAG (SEQ ID NO 49) | | | |

TABLE 6b-continued

Primers used for bisulfite pyrosequencing were:

| Name | | 5'- sequence -3' | 5'-end modification | product length | Annealing temperature (° C.) |
|---|---|---|---|---|---|
| | R2-3_F | GTGAGTTTTTGTGGAGGGATAGATGGTTGGA (SEQ ID NO 43) | Biotin | | 65 |
| | R2-3_R | CCCCACCCTAACTAAAACCACAAACCTAACAACTACC (SEQ ID NO 44) | | 349 bp | |
| | R2-3_seqR2 | CCCACAAAATAAATAAAAAATA (SEQ ID NO 45) | | | |
| | R2-3_seqR3 | CCCCCCACCAACCTA (SEQ ID NO 46) | | | |
| | R4_F | AGGTGGTGGGGTGGGGTAGAGA (SEQ ID NO 53) | | | 65 |
| | R4_R | CTCACCAACCCACCTACCCCAACT (SEQ ID NO 54) | Biotin | 183 bp | |
| | R4-seq | GGGTGGGGGTAGAGA (SEQ ID NO 55) | | | |
| | R5_F | TGGGAGGAGGAAGTTGTTGGAAGGTTAAA (SEQ ID NO 50) | Biotin | | 60 |
| | R5_R | CCTAAAAAACCCAAACCCTCCCCACCACCAACTAAATAT (SEQ ID NO 51) | | 289 bp | |
| | R5_seq | AAAAAAATCTCCCTACAACCT (SEQ ID NO 52) | | | |
| CSF1R LTR (THE1B) | FP | TAGGTGGAGATAATTGAATT (SEQ ID NO 82) | Biotin | 399 bp | 60 |
| | RP | CACATATACATTTACAACAATCT (SEQ ID NO 83) | | | |
| | seq | TATAAAACCATCAAATC (SEQ ID NO 84) | | | |

TABLE 6c

Primers used for LM-PCR were:

| | | | |
|---|---|---|---|
| CSF1R promoter | 1st | CTACTAGCTCCGCAGGGATCG (SEQ ID NO 56) | |
| | 2nd | ACACGTTCCTCTCCTCTGCACTG (SEQ ID NO 57) | |
| | 3rd | CTCTCCTCTGCACTGGCTGTTTGTCTTG (SEQ ID NO 58) | |
| TBP promoter | 1st | ATCTGTTACCTGGGTCACT (SEQ ID NO 59) | |
| | 2nd | AGATCACTATGGGCCAGCGGAAG (SEQ ID NO 60) | |
| | 3rd | ATGGGCCAGCGGAAGCGAAGTTAAACAG (SEQ ID NO 61) | |

Immunoprecipitation (IP) and Chromatin Immunoprecipitation (ChIP).

For CSF1R IP, 6×10⁷ untreated cells or cells treated for 5, 10, and 20 min with rhCSF-1 were washed in PBS and lyzed in HEPES buffer (pH 7.4) containing 137 mmol/l NaCl, 2 mmol/l EDTA, 1% Triton X-100, 10% glycerol, 1 mmol/l NaF, 1 mmol/l Na₃VO₄, phosphatase inhibitor cocktail II (P2850; Sigma-Aldrich), and the complete mini protease inhibitor cocktail (Roche). Lysates were centrifuged and supernatant was used for IP. After preclearance, IP was performed with 2.5 mg protein and 4 µg monoclonal anti-CSFR antibody (MAB3291) or the respective isotype control (MAB002; both R&D Systems) for 6 h. The precipitated proteins were separated by SDS-PAGE and blotted onto a nitrocellulose transfer membrane (Schleicher and Schuell). The membranes were incubated with a mouse monoclonal anti-p-Tyr antibody (sc-7020; Santa Cruz) and subsequently with horseradish peroxidase-conjugated secondary antibodies. Thereafter, membranes were reprobed with rabbit polyclonal anti-CSF1R (sc-692; SantaCruz). Bands were visualized with the enhanced chemiluminescence (ECL) system (Amersham Pharmacia Biotech). For ChIP analyses, exponentially growing cells were harvested, resuspended in 2.5 ml of RT-equilibrated cell culture medium per 1×10⁷ cells and cross-linked with 1% formaldehyde (Pierce) for 10 min at RT. The crosslinking reaction was quenched by the addition of glycine to a final concentration of 200 mmol/l, followed by two washes with ice-cold PBS. Cells were resuspended in 5 ml of ice-cold ChIP buffer A (10 mmol/l HEPES (pH 8.0), 10 mmol/l EDTA, 0.5 mmol/l EGTA, 0.25% Triton X-100, proteinase inhibitor cocktail (Roche)) per 1×10⁷ cells and incubated for 10 min at 4° C. with rotation, and centrifuged 5 min at 500×g at 4° C. The pellet was resuspended in 5 ml of ice-cold ChIP buffer B (10 mmol/l HEPES (pH 8.0), 200 mmol/l NaCl, 1 mmol/l EDTA, 0.5 mmol/l EGTA, 0.01% Triton X-100, protease inhibitor cocktail (Roche)) per 1×10⁷ cells, incubated for 10 min at 4° C. with rotation and centrifuged for 5 min at 500×g at 4° C. Cells were resuspended in 500 µl of ice-cold ChIP lysis buffer (25 mmol/l Tris-HCl (pH 8.0), 150 mmol/l NaCl, 1 mmol/l EDTA, 0.5 mmol/l EGTA, 1% Triton X-100, 0.25% SDS (Bio-Rad), protease inhibitor cocktail (Roche)) per 1×10⁷ cells, incubated 10 min on ice and sonicated at 5° C. using the Bioruptor™ (Diagenode) to generate fragments between 500-5000 bp (10-20 min with 30 s "ON" and "OFF" cycles, power setting high). The lysates were centrifuged for 10 min at 16.000×g at 4° C. and the supernatants were diluted with two volumes of ice-cold ChIP dilution buffer (25 mmol/l Tris-HCl (pH 8.0), 150 mmol/l NaCl, 1 mmol/l EDTA, 0.5 mmol/l EGTA, 1% Triton X-100, 7.5% glycerol, protease inhibitor cocktail (Roche)). For each TP, 10 µl of Dynabeads® protein G were pre-incubated with 50 µg BSA and 2 µg antibody (RNA polymerase II (Santa Cruz, sc-900X), H3K4me3 (Abcam, ab4441)) for 2 h at 4° C. with rotation. The blocked antibody bound protein G mix was added to 20-25 µg chromatin in a total volume of 500 µl diluted ChIP lysis buffer and incubated for 2 h at 4° C. with rotation. After magnetic separation the beads were washed once with 1 ml wash buffer 1 (20 mmol/l Tris-HCl (pH 8.0), 150 mmol/l NaCl, 2 mmol/l EDTA, 1% Triton X-100, 0.1% SDS), twice with 1 ml wash buffer 2 (20 mmol/l Tris-HCl (pH 8.0), 500 mmol/l NaCl, 2 mmol/l EDTA, 1% Triton X-100, 0.1% SDS), once with 1 ml LiCl buffer (10 mmol/l Tris-HCl (pH 8.0), 250 mmol/l LiCl, 1 mmol/l ETDA, 0.5% NP-40, 0.5% Na-deoxycholate) and twice with 1 ml TE/NaCl buffer (10 mmol/l Tris-HCl (pH 8.0), 50 mmol/l NaCl, 1 mmol/l EDTA). For each wash the beads were mixed with ice-cold washing buffers for 10 min at 4° C. The immunoprecipitated DNA was eluted two times with 50 µl ChIP elution buffer (100 mmol/l NaHCO$_3$, 1% SDS) for 15 min at RT with shaking. At this step the input control (1% of the starting material) was included in the experimental procedure after first adjusting the final volume to 100 µl with ChIP elution buffer. The eluted DNA was incubated overnight at 55° C. in the presence of 200 mmol/l NaCl, 10 mmol/l EDTA and 50 µg proteinase K. After adding Tris-HCl (pH 6.5) to a final concentration of 20 mmol/l to adjust the pH, the DNA was finally purified using Agencourt® AMPure® (Beckman Coulter) magnetic beads according to the manufacturer's instructions. The DNA was eluted with 50 µl 0.1×TE and analyzed by qRT-PCR or semi-quantitative PCR. Primers are listed in Table 3.1.

Bisulfite Pyrosequencing.

Bisulfite pyrosequencing of five amplicons covering the regions of transcription start sites of CBFA2T3 isoforms (isoform A: NM_005187.4; isoform B: NM_175931) was performed according to standard protocols with few modifications. Briefly, genomic DNA was bisulfite converted using the EpiTect Bisulfite Conversion Kit (Qiagen). In a following PCR amplification, locus-specific primers were used with one primer biotinylated at the 5' end (PCR and sequencing primer sequences are shown in Table 3.2). For amplification reactions, AccuPrime Taq Polymerase and buffer II (Invitrogen) were used with approximately 75 ng bisulfite converted DNA, and primers in a final volume of 25 µl. After initial denaturation, PCR consisted of 45 cycles of each 95° C. for 30 s, annealing temperature for 30 s, and 68° C. for 30 s followed by a final synthesis at 68° C. for 2 min. Amplification was verified by agarose gel electrophoresis. Using the Vacuum-Prep Tool (Biotage) single strands were prepared followed by a denaturation step at 85° C. for two min and final sequencing primer hybridization. Pyrosequencing was performed using the Pyrosequencer ID and the DNA methylation analysis software Pyro Q-CpG 1.0.9 (Biotage), which was also used to evaluate the ratio T:C (mC:C) at the CpG sites analyzed. All assays were optimized and validated using commercially available completely methylated DNA (Millipore) and pooled DNA isolated from peripheral blood of 10 healthy male and female controls, respectively.

Supplemental Methods

Transfections and Purification of Primary Cells.

Cells were electroporated (EP) in OPTI-MEM I using a Gene-Pulser II (Bio-Rad) with 950 µF and 0.18 kV (L428, L540Cy), 50 µF and 0.5 kV (KM-H2), 500 µF and 0.3 kV (Reh, L591). Transfection efficiency of transfected cells was determined by pEGFP-N3 (Clontech Laboratories) co transfection and subsequent FACS analysis. Reh cells were transfected with 30 µg of a pMSCVpuroH1-shCBFA2T3 and/or 30 µg of a pRK5-IKKβ(EE) expression plasmid or controls along with 10 µg pEGFP-N3. 48 h after transfection, GFP$^+$ cells were enriched by FACS sorting. For analysis of luciferase activity, L428, KM-H2, L540Cy, and L591 cells were transfected by EP with 10-14 µg of reporter constructs, together with 200-400 ng pRL-TKLuc as an internal control. 24-48 h after transfection, the ratio of the two luciferases was determined (Dual luciferase kit; Promega). Primary CD33$^+$ myeloid cells were purified from peripheral blood of healthy donors using the Monocyte Isolation Kit II (130-091-153), primary CD19$^+$ B cells from human tonsils with CD19 MicroBeads (130-050-301; both Miltenyi Biotec). Purity of CD33$^+$ and CD19$^+$ B cells was greater than 83% and 97%, respectively.

DNA Constructs.

Where indicated, the binding site for Sp1 was mutated from 5'-GGGTGGGG-3' to 5'-G<u>TTT</u>GGGG-3', for GATA from 5'-AGATAA-3' to 5'-A<u>CTT</u>AA-3', for AP-1 from 5'-TGAATCA-3' to 5'-TGAA<u>TTG</u>-3', for NF-κB from 5'-GG-GAGTTCCCC-3' (SEQ ID NO 14) to 5'-GG<u>CCTTT AACC</u>-3' (SEQ ID NO 15) by use of the QuickChange Multi Site-Directed Mutagenesis Kit (Stratagene).

Measurement of the Secreted Amount of CSF-1 by ELISA.

ELISA was performed with supernatants of various cell lines by use of the CSF-1 DuoSet ELISA Development kit (DY216; R&D Systems). For collection of cell culture supernatants for ELISA, cells were plated at 0.8×10$^6$ ml$^{-1}$, and supernatants were collected after 48 hours.

Proliferation Assays and Analysis of Apoptosis.

We determined DNA synthesis by [$^3$H]-thymidine incorporation assays using standard protocols. In case of L540Cy cells (FIG. 1d), after 48 hours, cells were pulsed with 1 µCi [$^3$H]-thymidine per well for a further 20 hours, and [$^3$H]-thymidine incorporation was determined. In case of KM-H2 cells (FIG. 1e), after 24 hours, cells were pulsed with 1 µCi [$^3$H]-thymidine per well for a further 20 hours, and [$^3$H]-thymidine incorporation was determined. The percentage of viable and apoptotic cells was determined by annexin V-FITC/propidium iodide (PI) double-staining (Bender MedSystems) and flow cytometry.

Immunoprecipitation (IP).

For CSF1R IP, 6×10$^7$ untreated cells or cells treated for 5, 10, and 20 min with rhCSF-1 were washed in PBS and lysed in HEPES buffer (pH 7.4) containing 137 mM NaCl, 2 mM EDTA, 1% Triton X-100, 10% glycerol, 1 mM NaF, 1 mM Na$_3$VO$_4$, phosphatase inhibitor cocktail II (P2850; Sigma-Aldrich), and the complete mini protease inhibitor cocktail (Roche). Lysates were centrifuged and supernatant was used for IP. After preclearance, IP was performed with 2.5 mg protein and 4 µg monoclonal antibody to CSFR (MAB3291) or the respective isotype control (MAB002; both R&D Systems) for 6 h. The precipitated proteins were separated by SDS-PAGE and blotted onto a nitrocellulose transfer membrane (Schleicher and Schuell). The membranes were incubated with a mouse monoclonal antibody to p-Tyr (sc-7020; Santa Cruz) and subsequently with horseradish peroxidase-conjugated secondary antibodies. Thereafter, membranes were reprobed with rabbit polyclonal antibody to CSF (sc-692; SantaCruz). Bands were visualized with the enhanced chemiluminescence (ECL) system (Amersham Pharmacia Biotech).

For ChIP analyses, exponentially growing cells were harvested, resuspended in 2.5 ml of RT-equilibrated cell culture medium per 1×10$^7$ cells and cross-linked with 1% formaldehyde (Pierce) for 10 min at RT. The crosslinking reaction was quenched by the addition of glycine to a final concentration of 200 mM, followed by two washes with ice-cold PBS. Cells were resuspended in 5 ml of ice-cold ChIP buffer A (10 mM HEPES (pH 8.0), 10 mM EDTA, 0.5 mM EGTA, 0.25% Triton X-100, proteinase inhibitor cocktail (Roche)) per 1×10$^7$ cells and incubated for 10 min at 4° C. with rotation, and centrifuged 5 min at 500×g at 4° C. The pellet was resuspended in 5 ml of ice-cold ChIP buffer B (10 mM HEPES (pH 8.0), 200 mM NaCl, 1 mM EDTA, 0.5 mM EGTA, 0.01% Triton X-100, protease inhibitor cocktail (Roche)) per 1×10$^7$ cells, incubated for 10 min at 4° C. with rotation and centrifuged for 5 min at 500×g at 4° C. Cells were resuspended in 500 µl of ice-cold ChIP lysis buffer (25 mM Tris-HCl (pH 8.0), 150 mM NaCl, 1 mM EDTA, 0.5 mM EGTA, 1% Triton X-100, 0.25% SDS (Bio-Rad), protease inhibitor cocktail (Roche)) per 1×10$^7$ cells, incubated 10 min on ice and sonicated at 5° C. using the Bioruptor™ (Diagenode) to generate fragments between 500-5,000 bp (10-20 min with 30 s "ON" and "OFF" cycles, power setting high). The lysates were centrifuged for 10 min at 16,000×g at 4° C. and the supernatants were diluted with two volumes of ice-cold ChIP dilution buffer (25 mM Tris-HCl (pH 8.0), 150 mM NaCl, 1 mM EDTA, 0.5 mM EGTA, 1% Triton X-100, 7.5% glycerol, protease inhibitor cocktail (Roche)). For each IP, 10 µl of Dynabeads® protein G were pre-incubated with 50 µg BSA and 2 µg antibody (RNA polymerase II (Santa Cruz, sc-900X), H3K4me3 (Abcam, ab4441)) for 2 h at 4° C. with rotation. The blocked antibody bound protein G mix was added to 20-25 µg chromatin in a total volume of 500 µl diluted ChIP lysis buffer and incubated for 2 h at 4° C. with rotation. After magnetic separation the beads were washed once with 1 ml wash buffer 1 (20 mM Tris-HCl (pH 8.0), 150 mM NaCl, 2 mM EDTA, 1% Triton X-100, 0.1% SDS), twice with 1 ml wash buffer 2 (20 mM Tris-HCl (pH 8.0), 500 mM NaCl, 2 mM EDTA, 1% Triton X-100, 0.1% SDS), once with 1 ml LiCl buffer (10 mM Tris-HCl (pH 8.0), 250 mM LiCl, 1 mM ETDA, 0.5% NP-40, 0.5% Na-deoxycholate) and twice with 1 ml TE/NaCl buffer (10 mM Tris-HCl (pH 8.0), 50 mM NaCl, 1 mM EDTA). For each wash the beads were mixed with ice-cold washing buffers for 10 min at 4° C. The immunoprecipitated DNA was eluted two times with 50 µl ChIP elution buffer (100 mM NaHCO$_3$, 1% SDS) for 15 min at RT with shaking. At this step the input control (1% of the starting material) was included in the experimental procedure after first adjusting the final volume to 100 µl with ChIP elution buffer. The eluted DNA was incubated overnight at 55° C. in the presence of 200 mM NaCl, 10 mM EDTA and 50 µg proteinase K. After adding Tris-HCl (pH 6.5) to a final concentration of 20 mM to adjust the pH, the DNA was finally purified using Agencourt® AMPure® (Beckman Coulter) magnetic beads according to the manufacturer's instructions. The DNA was eluted with 50 µl 0.1×TE and analyzed by qRT-PCR or semi-quantitative PCR. Primers are listed in Table 6a.

Bisulfite-Pyrosequencing.

Genomic DNA from the various cell lines and primary lymphoma samples was prepared according to standard protocols. Bisulfite-pyrosequencing of five amplicons covering the regions of transcription start sites of CBFA2T3 isoforms (isoform A: NM_005187.4; isoform B: NM_175931) and of the CSF1R-LTR was performed according to standard protocols with few modifications. Briefly, genomic DNA was bisulfite converted using the EpiTect Bisulfite Conversion Kit (Qiagen). In a following PCR amplification locus-specific primers were used with one primer biotinylated at the 5' end (PCR and sequencing primer sequences are shown in Table 5b) For CBFA2T3 amplification reactions, AccuPrime Taq Polymerase and buffer II (Invitrogen) were used with approximately 75 ng bisulfite converted DNA, and primers in a final volume of 25 µl. For CSF1R-LTR amplification reactions the PyroMark PCR Kit (Qiagen) was used according to standard protocol. After initial denaturation, PCR consisted of 45 cycles of each 95° C. for 30 s, annealing temperature for 30 s, and 68° C. for 30 s followed by a final synthesis at 68° C. for 2 min. Amplification was verified by agarose gel electrophoresis. Using the VacuumPrep Tool (Biotage) single strands were prepared followed by a denaturation step at 85° C. for two min and final sequencing primer hybridization. Pyrosequencing was performed using the Pyrosequencer ID and the DNA methylation analysis software Pyro Q-CpG 1.0.9 (Biotage), which was also used to evaluate the ratio T:C (mC:C) at the CpG sites analyzed. All assays were optimized and validated using commercially available completely methylated DNA (Millipore) and pooled DNA isolated from peripheral blood of 10 healthy male and female controls, respectively.

Interphase Cytogenetics.

For determining copy number of chromosome 16 and estimating ploidy of HRS cells, commercial probes for the centromeric regions of chromosomes 6 (CEP6, Spectrum Aqua), 10 (CEP10, Spectrum Aqua), 16 (CEP16, Spectrum Aqua) and 17 (CEP17, Spectrum Green) were used. For FICTION, immunofluorescence with antibody to CD30 detected with an Alexa-594 conjugated secondary antibody (Molecular Probes) was applied. The median number of HRS cells evaluated for 16q24.3 and CEP16 per case was 26 (10-36). Nuclei of bystander cells served as internal controls.

Oligonucleotide Microarray Analyses.

Reh cells were transfected in duplicate with different combinations of vectors encoding shCBFA2T3 and/or IKKβ(EE) or the respective control plasmids along with pEGFP. 72 hours after transfection, pEGFP$^+$ cells were enriched by flow cytometry. RNA processing and hybridization to Human Genome U133 Plus 2.0 arrays (Affymetrix) were performed according to the manufacturer's recommendation (Affymetrix). All processing of data was done in R (http://www.r-project.org). RMA background correction and quantile normalization were applied to raw data. Processed data were variance-filtered with an interquartile range cutoff of 0.5. Significantly deregulated features were extracted using LIMMA with an adjusted p-value cutoff of 0.05 and a log$_2$-fold change cutoff of 0.5. The microarray data are available from the Gene Expression Omnibus of the National Center for Biotechnology Information (www.ncbi.nlm.nih.gov/geo/) through the GEO accession number GSE20115.

5'RACE of LTR RNAs by TD-PCR Amplification.

Sequence-specific reverse transcription reactions were performed on RNA isolated from four HRS cell lines and three non-Hodgkin B cell lines, using an equimolar mixture of the reverse THE1B consensus primer_1 (5% CATG-GCTGGGGAGGCCTCA-3' (SEQ ID NO 85)) and the reverse CSF1R-LTR primer_1 (5'-CATGGCTGAGAGGC-CTCA-3' (SEQ ID NO 86)) which differ by one base (highlighted in bold). As depicted in FIG. 18c, these primers correspond to a highly conserved region of the LTRs located just upstream of the predicted RNA splice site. The THE1B primer also perfectly matches the THE1A and THE1C LTR consensus sequences (Smit, A. F. *Nucleic Acids Res.* 21, 1863-1872 (1993)). For terminal transferase-dependent PCR (TD-PCR), the cDNAs were subjected to limited ribonucleotide tailing with GTP so as to add approximately three G bases to the 3' termini as previously described (Schmidt, W. M. et al. *Nucleic Acids Res.* 24, 1789-1791 (1996)). A double-stranded DNA linker carrying a complementary 3' overhang was made from the two oligonucleotides SSL2 (5'-AATTCA-GATCTCCCGGGTCACCGC-3' (SEQ ID NO 87)) and SSL41 (5'-GCGGTGACCCGGGAGATCTGAATTCCC-3' (SEQ ID NO 88)) and ligated to the ribonucleotide-tailed cDNAs with T4 DNA ligase. PCR was performed on the ligation products using the primer LP25 (5'-GCGGTGAC-CCGGGAGATCTGAATTC-3' (SEQ ID NO 89)) and the same mixture of reverse primers as used to make the cDNA.

These reactions are predicted to generate products of 105, 109 and 85 bp for the THE1A, THE1B and THE1C consensus sequences respectively. Subsequent nested PCR to amplify either THE1B consensus or CSF1R-like LTRs was performed using the LP25 primer in combination with either the reverse THE1B primer_2 (5'-GGGAGGCCTCACAATCATGG-3' (SEQ ID NO 90)) or the reverse CSF1R-LTR primer_2 (5'-AGGAGGCCTCAGAATCATAG-3' (SEQ ID NO 91)) (bases that differ shown in bold). These primers can also potentially amplify THE1A family LTRs, but are unlikely to amplify THE1C. PCR products were subsequently cloned into the plasmid vector pCR 2.1-TOPO, and individual clones were sequenced in both directions. Sequences were aligned with the hg19 build 37.1 2009 assembly of the human genome sequence.

3'RACE of THE1-Driven LTR Transcripts.

3'RACE for detection of THE1-driven LTR transcripts was performed by use of the ExactSTART™ Eukaryotic mRNA 5'- & 3'-RACE Kit (Epicentre Biotechnologies). In brief, to construct, based on 6 μg mRNA of each cell line, a double-stranded cDNA, alkaline phosphatase treatment, tobacco acid pyrophosphatase treatment, 5'-ligation-tagging, first strand cDNA synthesis and second-strand cDNA synthesis and PCR amplification were performed according to the manufacturer's recommendations. To control, that full-length mRNAs were equally transcribed into double stranded cDNAs in the various cell lines, the 5'-ends and the 3'-ends of ACTB (βετα-αχτιν) were amplified by 5'RACE, using PCR primer_1 (provided by the ExactSTART™ kit; recognizing a 5'tagging sequence) in combination with ACTB reverse primer 5'-AGGTGTGGTGCCAGATTTTC-3' (SEQ ID NO 92) (36 cycles, 60° C.; product size ~400 bp), and by 3'RACE, using PCR primer_2 (provided by the ExactSTART™ kit; recognizing a 3'tagging sequence) in combination with ACTB forward primer 5'-TTTGAATGATGAGCCTTCGTGCCC-3' (SEQ ID NO 93) (36 cycles, 60° C.; product size ~250-300 bp). 3'RACE for the detection of THE1-family driven transcripts was performed by use of forward consensus THE1B primer_2 or forward CSF1R primer_2 (FIG. 18c) in combination with PCR primer_2 (28 cycles, 65° C.). PCR products were subsequently cloned into the plasmid vector pGEM-T easy (Promega), and individual clones were sequenced in both directions. Sequences of 14 clones were aligned with the hg19 build 37.1 2009 assembly of the human genome sequence. 12 of these were THE1-family driven, correctly spliced and polyadenylated mRNA transcripts.

Immunohistochemistry (IHC) and RNA In Situ Hybridization (ISH).

For IHC, the dewaxed four μm sections were subjected to an antigen-demasking procedure of brief, high-temperature heating of the sections immersed in citrate buffer (10 mM, pH 6.0) and heating for two min in a high-pressure cooker. CBFA2T3 antibody[39] was applied at a dilution of 1:500. Bound antibody was visualized using the alkaline phosphatase anti-alkaline phosphatase method and FastRed as chromogen (DAKO). For RNA ISH, paraffin-embedded tissue specimens were dewaxed and treated with proteinase K (DAKO; 1:10 dilution). Hybridization with biotin-labeled CSF1R probes (fragment +720 to +1,325; sense (negative control) and anti-sense orientation) was performed over night at 50° C. in a DAKO hybridizer. The hybridized sections were washed under stringent conditions in order to get rid of unspecifically bound probes. Detection of specifically bound probe was carried out after blocking of endogenous biotin with a streptavidin-AP conjugate employing NBT/BCIP (DAKO) as a substrate.

Bagg, A. (2007). Lineage ambiguity, infidelity, and promiscuity in immunophenotypically complex acute leukemias: genetic and morphologic correlates. Am J Clin Pathol 128, 545-548.

Bonifer, C., and Hume, D. A. (2008). The transcriptional regulation of the Colony-Stimulating Factor 1 Receptor (csf1r) gene during hematopoiesis. Front Biosci 13, 549-560.

Borowitz, M. J., Béné, M. C., Harris, N. L., Porwit, A., and Matutes, E. (2008). Acute leukaemias of ambiguous lineage. In WHO Classification of Tumours of Haematopoietic and Lymphoid Tissues, S. H. Swerdlow, E. Campo, N. L. Harris, E. S. Jaffe, Pileri S. A., H. Stein, J. Thiele, Vardiman, eds. (IARC, Lyon). pp. 149-155.

Borzillo, G. V., Ashmun, R. A., and Sherr, C. J. (1990). Macrophage lineage switching of murine early pre-B lymphoid cells expressing transduced fms genes. Mol Cell Biol 10, 2703-2714.

Burns, C. J., Harte, M. F., Bu, X., Fantino, E., Giarrusso, M., Joffe, M., Kurek, M., Legge, F. S., Razzino, P., Su, S., et al. (2009). Discovery of 2-(alpha-methylbenzylamino) pyrazines as potent Type II inhibitors of FMS. Bioorg Med Chem Lett 19, 1206-1209.

Chyla, B. J., Moreno-Miralles, I., Steapleton, M. A., Thompson, M. A., Bhaskara, S., Engel, M., and Hiebert, S. W. (2008). Deletion of Mtg16, a target of t(16;21), alters hematopoietic progenitor cell proliferation and lineage allocation. Mol Cell Biol 28, 6234-6247.

Cobaleda, C., Jochum, W., and Busslinger, M. (2007). Conversion of mature B cells into T cells by dedifferentiation to uncommitted progenitors. Nature 449, 473-477.

Dai, X. M., Ryan, G. R., Hapel, A. J., Dominguez, M. G., Russell, R. G., Kapp, S., Sylvestre, V., and Stanley, E. R. (2002). Targeted disruption of the mouse colony-stimulating factor 1 receptor gene results in osteopetrosis, mononuclear phagocyte deficiency, increased primitive progenitor cell frequencies, and reproductive defects. Blood 99, 111-120.

Delhase, M., Hayakawa, M., Chen, Y., and Karin, M. (1999). Positive and negative regulation of IkappaB kinase activity through IKKbeta subunit phosphorylation. Science 284, 309-313.

Downing, J. R., Shurtleff, S. A., and Sherr, C. J. (1991). Peptide antisera to human colony-stimulating factor 1 receptor detect ligand-induced conformational changes and a binding site for phosphatidylinositol 3-kinase. Mol Cell Biol 11, 2489-2495.

Druker, R., and Whitelaw, E. (2004). Retrotransposon-derived elements in the mammalian genome: a potential source of disease. J Inherit Metab Dis 27, 319-330.

Eden, A., Gaudet, F., Waghmare, A., and Jaenisch, R. (2003). Chromosomal instability and tumors promoted by DNA hypomethylation. Science 300, 455.

Ehlers, A., Oker, E., Bentink, S., Lenze, D., Stein, H., and Hummel, M. (2008). Histone acetylation and DNA demethylation of B cells result in a Hodgkin-like phenotype. Leukemia 22, 835-841.

Ehrlich, M. (2002). DNA methylation in cancer: too much, but also too little. Oncogene 21, 5400-5413.

Esteller, M. (2002). CpG island hypermethylation and tumor suppressor genes: a booming present, a brighter future. Oncogene 21, 5427-5440.

Fan, T., Schmidtmann, A., Xi, S., Briones, V., Zhu, H., Suh, H. C., Gooya, J., Keller, J. R., Xu, H., Roayaei, J., et al. (2008). DNA hypomethylation caused by Lsh deletion promotes erythroleukemia development. Epigenetics 3, 134-142.

Faulkner, G. J., Kimura, Y., Daub, C. O., Wani, S., Plessy, C., Irvine, K. M., Schroder, K., Cloonan, N., Steptoe, A. L., Lassmann, T., et al. (2009). The regulated retrotransposon transcriptome of mammalian cells. Nat Genet 41, 563-571.

Feldman, A. L., Arber, D. A., Pittaluga, S., Martinez, A., Burke, J. S., Raffeld, M., Camos, M., Warnke, R., and Jaffe, E. S. (2008). Clonally related follicular lymphomas and histiocytic/dendritic cell sarcomas: evidence for transdifferentiation of the follicular lymphoma clone. Blood 111, 5433-5439.

Follows, G. A., Tagoh, H., Lefevre, P., Morgan, G. J., and Bonifer, C. (2003). Differential transcription factor occupancy but evolutionarily conserved chromatin features at the human and mouse M-CSF (CSF-1) receptor loci. Nucleic Acids Res 31, 5805-5816.

Gamou, T., Kitamura, E., Hosoda, F., Shimizu, K., Shinohara, K., Hayashi, Y., Nagase, T., Yokoyama, Y., and Ohki, M. (1998). The partner gene of AML1 in t(16;21) myeloid malignancies is a novel member of the MTG8 (ETO) family. Blood 91, 4028-4037.

Goardon, N., Lambert, J. A., Rodriguez, P., Nissaire, P., Herblot, S., Thibault, P., Dumenil, D., Strouboulis, J., Romeo, P. H., and Hoang, T. (2006). ETO2 coordinates cellular proliferation and differentiation during erythropoiesis. Embo J 25, 357-366.

Hinz, M., Lemke, P., Anagnostopoulos, I., Hacker, C., Krappmann, D., Mathas, S., Darken, B., Zenke, M., Stein, H., and Scheidereit, C. (2002). Nuclear factor kappaB-dependent gene expression profiling of Hodgkin's disease tumor cells, pathogenetic significance, and link to constitutive signal transducer and activator of transcription 5a activity. J Exp Med 196, 605-617.

Höpken, U. E., Foss, H. D., Meyer, D., Hinz, M., Leder, K., Stein, H., and Lipp, M. (2002). Up-regulation of the chemokine receptor CCR7 in classical but not in lymphocyte-predominant Hodgkin disease correlates with distinct dissemination of neoplastic cells in lymphoid organs. Blood 99, 1109-1116.

Howard, G., Eiges, R., Gaudet, F., Jaenisch, R., and Eden, A. (2008). Activation and transposition of endogenous retroviral elements in hypomethylation induced tumors in mice. Oncogene 27, 404-408.

Huang, J., Fan, T., Yan, Q., Zhu, H., Fox, S., Issaq, H. J., Best, L., Gangi, L., Munroe, D., and Muegge, K. (2004). Lsh, an epigenetic guardian of repetitive elements. Nucleic Acids Res 32, 5019-5028.

Hug, B. A., and Lazar, M. A. (2004). ETO interacting proteins. Oncogene 23, 4270-4274.

Ikawa, T., Kawamoto, H., Wright, L. Y., and Murre, C. (2004). Long-term cultured E2A-deficient hematopoietic progenitor cells are pluripotent. Immunity 20, 349-360.

Irvine, K. M., Burns, C. J., Wilks, A. F., Su, S., Hume, D. A., and Sweet, M. J. (2006). A CSF-1 receptor kinase inhibitor targets effector functions and inhibits pro-inflammatory cytokine production from murine macrophage populations. Faseb J 20, 1921-1923.

Janz, M., Dorken, B., and Mathas, S. (2006). Reprogramming of B lymphoid cells in human lymphoma pathogenesis. Cell Cycle 5, 1057-1061.

Jern, P., and Coffin, J. M. (2008). Effects of retroviruses on host genome function. Annu Rev Genet 42, 709-732.

Jones, P. A., and Baylin, S. B. (2002). The fundamental role of epigenetic events in cancer. Nat Rev Genet 3, 415-428.

Joos, S., Menz, C. K., Wrobel, G., Siebert, R., Gesk, S., Ohl, S., Mechtersheimer, G., Trümper, L., Möller, P., Lichter, P., and Barth, T. F. (2002). Classical Hodgkin lymphoma is characterized by recurrent copy number gains of the short arm of chromosome 2. Blood 99, 1381-1387.

Jundt, F., Kley, K., Anagnostopoulos, I., Schulze Pröbsting, K., Greiner, A., Mathas, S., Scheidereit, C., Wirth, T., Stein, H., and Dörken, B. (2002). Loss of PU.1 expression is associated with defective immunoglobulin transcription in Hodgkin and Reed-Sternberg cells of classical Hodgkin disease. Blood 99, 3060-3062.

Kochetkova, M., McKenzie, O. L., Bais, A. J., Martin, J. M., Secker, G. A., Seshadri, R., Powell, J. A., Hinze, S. J., Gardner, A. E., Spendlove, H. E., et al. (2002). CBFA2T3 (MTG16) is a putative breast tumor suppressor gene from the breast cancer loss of heterozygosity region at 16q24.3. Cancer Res 62, 4599-4604.

Kumar, R., Cheney, K. M., McKirdy, R., Neilsen, P. M., Schulz, R. B., Lee, J., Cohen, J., Booker, G. W., and Callen, D. F. (2008). CBFA2T3-ZNF652 corepressor complex regulates transcription of the E-box gene HEB. J Biol Chem 283, 19026-19038.

Küppers, R. (2009). The biology of Hodgkin's lymphoma. Nat Rev Cancer 9, 15-27.

Küppers, R., Klein, U., Schwering, I., Distler, V., Bräuninger, A., Cattoretti, G., Tu, Y., Stolovitzky, G. A., Califano, A., Hansmann, M. L., and Dalla-Favera, R. (2003). Identification of Hodgkin and Reed-Sternberg cell-specific genes by gene expression profiling. J Clin Invest 111, 529-537.

Lee, S. H., Wang, X., and DeJong, J. (2000). Functional interactions between an atypical NF-kappaB site from the rat CYP2B1 promoter and the transcriptional repressor RBP-Jkappa/CBF1. Nucleic Acids Res 28, 2091-2098.

Legrand, O., Perrot, J. Y., Simonin, G., Baudard, M., Cadiou, M., Blanc, C., Ramond, S., Viguie, F., Marie, J. P., and Zittoun, R. (1998). Adult biphenotypic acute leukaemia: an entity with poor prognosis which is related to unfavourable cytogenetics and P-glycoprotein over-expression. Br J Haematol 100, 147-155.

Li, X., Massa, P. E., Hanidu, A., Peet, G. W., Aro, P., Savitt, A., Mische, S., Li, J., and Marcu, K. B. (2002). IKKalpha, IKKbeta, and NEMO/IKKgamma are each required for the NF-kappa B-mediated inflammatory response program. J Biol Chem 277, 45129-45140.

MacLeod, R. A., Spitzer, D., Bar-Am, I., Sylvester, J. E., Kaufmann, M., Wernich, A., and Drexler, H. G. (2000). Karyotypic dissection of Hodgkin's disease cell lines reveals ectopic subtelomeres and ribosomal DNA at sites of multiple jumping translocations and genomic amplification. Leukemia 14, 1803-1814.

Maksakova, I. A., Mager, D. L., and Reiss, D. (2008). Keeping active endogenous retroviral-like elements in check: the epigenetic perspective. Cell Mol Life Sci 65, 3329-3347.

Martin-Subero, J. I., Gesk, S., Harder, L., Sonoki, T., Tucker, P. W., Schlegelberger, B., Grote, W., Novo, F. J., Calasanz, M. J., Hansmann, M. L., et al. (2002). Recurrent involvement of the REL and BCL11A loci in classical Hodgkin lymphoma. Blood 99, 1474-1477.

Mathas, S., Hinz, M., Anagnostopoulos, I., Krappmann, D., Lietz, A., Jundt, F., Bommert, K., Mechta-Grigoriou, F., Stein, H., Dörken, B., et al. (2002). Aberrantly expressed c-Jun and JunB are a hallmark of Hodgkin lymphoma cells, stimulate proliferation and synergize with NF-kappa B. Embo J 21, 4104-4113.

Mathas, S., Janz, M., Hummel, F., Hummel, M., Wollert-Wulf, B., Lusatis, S., Anagnostopoulos, I., Lietz, A., Sigvardsson, M., Jundt, F., et al. (2006). Intrinsic inhibition of transcription factor E2A by HLH proteins ABF-1 and Id2 mediates reprogramming of neoplastic B cells in Hodgkin lymphoma. Nat Immunol 7, 207-215.

Moreau, A., Praloran, V., Berrada, L., Coupey, L., and Gaillard, F. (1992). Immunohistochemical detection of cells positive for colony-stimulating factor 1 in lymph nodes from reactive lymphadenitis, and Hodgkin's disease. Leukemia 6, 126-130.

Nutt, S. L., and Kee, B. L. (2007). The transcriptional regulation of B cell lineage commitment. Immunity 26, 715-725.

Ohshima, K., Haraoka, S., Yoshioka, S., Kawasaki, C., Tutiya, T., Suzumiya, J., and Kikuchi, M. (2001). Chromosome 16q deletion and loss of E-cadherin expression in Hodgkin and Reed-Sternberg cells. Int J Cancer 92, 678-682.

Pixley, F. J., and Stanley, E. R. (2004). CSF-1 regulation of the wandering macrophage: complexity in action. Trends Cell Biol 14, 628-638.

Prindull, G., and Zipori, D. (2004). Environmental guidance of normal and tumor cell plasticity: epithelial mesenchymal transitions as a paradigm. Blood 103, 2892-2899.

Roussel, M. F., Dull, T. J., Rettenmier, C. W., Ralph, P., Ullrich, A., and Sherr, C. J. (1987). Transforming potential of the c-fms proto-oncogene (CSF-1 receptor). Nature 325, 549-552.

Smit, A. F. (1993). Identification of a new, abundant superfamily of mammalian LTR-transposons. Nucleic Acids Res 21, 1863-1872.

Souabni, A., Jochum, W., and Busslinger, M. (2007). Oncogenic role of Pax5 in the T-lymphoid lineage upon ectopic expression from the immunoglobulin heavy-chain locus. Blood 109, 281-289.

Tagoh, H., Ingram, R., Wilson, N., Salvagiotto, G., Warren, A. J., Clarke, D., Busslinger, M., and Bonifer, C. (2006). The mechanism of repression of the myeloid-specific c-fms gene by Pax5 during B lineage restriction. Embo J 25, 1070-1080.

Ushmorov, A., Leithäuser, F., Sakk, O., Weinhausel, A., Popov, S. W., Möller, P., and Wirth, T. (2006). Epigenetic processes play a major role in B-cell-specific gene silencing in classical Hodgkin lymphoma. Blood 107, 2493-2500.

Visvader, J., and Verma, I. M. (1989). Differential transcription of exon 1 of the human c-fms gene in placental trophoblasts and monocytes. Mol Cell Biol 9, 1336-1341.

Walter, K., Bonifer, C., and Tagoh, H. (2008). Stem cell-specific epigenetic priming and B cell-specific transcriptional activation at the mouse Cd19 locus. Blood 112, 1673-1682.

The invention claimed is:

1. A cDNA molecule, derived from an RNA molecule transcribed from a long terminal repeat (LTR) sequence, comprising one of:
   (a) a sequence encoding a CSF1R gene; and
   (b) a sequence that is at least in part found in the LTR; or
   (c) a reverse complementary sequence thereof;
   wherein the sequence is at least 90% identical to one of SEQ ID NO 3 or 4.

2. The cDNA molecule of claim 1, wherein the cDNA molecule is used for at least one of for diagnosing, monitoring, and prognosing cancer in a subject.

3. A method for diagnosing, monitoring, and/or prognosing cancer based on a biological sample, wherein the method comprises detection of the cDNA molecule of claim 1.

4. The method of claim 3, wherein the detection of the molecule is through performing an amplification reaction or using a microarray.

5. The method of claim 4, wherein the amplification reaction is selected from the group consisting of polymerase chain reaction, including a real time polymerase chain reaction; and ligase chain reaction.

6. The method of claim 3, wherein the cancer is malignant hematological disease selected from the group consisting of Hodgkin lymphoma and anaplastic large cell lymphoma.

7. A vector comprising a sequence of claim 1, comprising a sequence of according to SEQ ID NO 3 or 4.

8. The vector of claim 7, in which the sequence according to SEQ ID NO 3 or 4 is operatively linked to an expression control sequence allowing expression in a prokaryotic or a eukaryotic host cell.

9. A prokaryotic host cell genetically engineered with a sequence according to SEQ ID NO 3 or 4, or with the vector of claim 7.

10. The cDNA molecule of claim 1, wherein the sequence that is at least in part found in the LTR is located at a 5' portion of the RNA molecule.

11. The cDNA molecule of claim 1, wherein the LTR sequence comprises a sequence from a THE1 family of LTRs.

* * * * *

UNITED STATES PATENT AND TRADEMARK OFFICE
CERTIFICATE OF CORRECTION

PATENT NO.         : 9,115,404 B2  
APPLICATION NO.    : 13/379084  
DATED              : August 25, 2015  
INVENTOR(S)        : Stephan Mathas et al.

Page 1 of 1

It is certified that error appears in the above-identified patent and that said Letters Patent is hereby corrected as shown below:

In the claims:

COL. 85, line 27, after "at least one of" please delete "for"

COL. 86, line 23, before "according to" please delete "of"

Signed and Sealed this  
Fifth Day of January, 2016

Michelle K. Lee  
*Director of the United States Patent and Trademark Office*